(12) United States Patent
Willert et al.

(10) Patent No.: US 10,766,962 B2
(45) Date of Patent: Sep. 8, 2020

(54) FZD7 SPECIFIC ANTIBODIES AND VACCINES TO TREAT CANCER AND CONTROL STEM CELL FUNCTION

(71) Applicant: THE REGENTS OF THE UNIVERSITY OF CALIFORNIA, Oakland, CA (US)

(72) Inventors: Karl Willert, Del Mar, CA (US); Dennis Carson, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 121 days.

(21) Appl. No.: 15/736,646

(22) PCT Filed: Jun. 16, 2016

(86) PCT No.: PCT/US2016/037919
§ 371 (c)(1),
(2) Date: Dec. 14, 2017

(87) PCT Pub. No.: WO2016/205551
PCT Pub. Date: Dec. 22, 2016

(65) Prior Publication Data
US 2018/0186885 A1    Jul. 5, 2018

Related U.S. Application Data

(60) Provisional application No. 62/180,359, filed on Jun. 16, 2015.

(51) Int. Cl.
*C07K 16/00*    (2006.01)
*C07K 16/28*    (2006.01)
*C07K 16/30*    (2006.01)

(52) U.S. Cl.
CPC .......... *C07K 16/2863* (2013.01); *C07K 16/30* (2013.01); *C07K 2317/24* (2013.01); *C07K 2317/33* (2013.01); *C07K 2317/34* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| 2008/0038272 A1* | 2/2008 | Buehring | C07K 16/28 424/143.1 |
|---|---|---|---|
| 2008/0194457 A1 | 8/2008 | Wands et al. | |
| 2010/0111852 A1 | 5/2010 | Yoshida | |
| 2014/0134159 A1 | 5/2014 | Stagg et al. | |
| 2014/0271629 A1 | 9/2014 | Corbit et al. | |

FOREIGN PATENT DOCUMENTS

WO    WO-2016/205551 A2    12/2016

OTHER PUBLICATIONS

Paul, Fundamental Immunology, 3rd Edition, 1993, pp. 292-295, under the heading Fv Structure and Diversity in Three Dimensions (Year: 1993).*
Rudikoff et al., (Proc. Natl. Acad. Sci. USA 1982 vol. 79: p. 1979 (Year: 1979).*
Casset et al (BBRC 307, 198-205 2003 (Year: 2003).*
Pascalis et al (The Journal of Immunology vol. 169, 3076-3084, 2002 (Year: 2002).*
Anti-FZD7 polyclonal antibodies, Sigma-Aldrich AV41251 (available before Oct. 2014 (Year: 2014).*
Chakrabarti et al (Nature cell Bio 16:1004-1015 and supplemental document-method, published online Set 2014 (Year: 2014).*
Fzd7 Frizzled-7 precursor—Mus musculus (Mouse) Fzd7 gene & protein UniProtKB Q61090 (FZD7_MOUSE), Sep. 29, 2016, 4 pages.
Fzd7 Frizzled-7 precursor—*Homo sapiens* (Human) Fzd7 gene & protein UniProtKB O75084 (FZD7_HUMAN), Sep. 29, 2016, 4 pages.
Asad, et al., "FZD7 drives in vitro aggressiveness in Stem-A subtype of ovarian cancer via regulation of non-canonical Wnt/PCP pathway", Cell Death and Disease (2014) 5, e1346, 12 pages.
Fernandez, et al., "The WNT receptor FZD7 is required for maintenance of the pluripotent state in human embryonic stem cells", Proceedings of the National Academy of Sciences, Jan. 28, 2014, vol. 111, No. 4, pp. 1409-1414.
Gurney, et al., "Wnt pathway inhibition via the targeting of Frizzled receptors results in decreased growth and tumorigenicity of human tumors" Proceedings of the National Academy of Sciences of the United States of America, Jul. 17, 2012, vol. 109, No. 29, pp. 11717-11722.
Nambotin, et al., "Functional consequences of WNT3/Frizzled7-mediated signaling in non-transformed hepatic cells", Oncogenesis (2012) 1, e31, 9 pages.

(Continued)

*Primary Examiner* — Lei Yao
(74) *Attorney, Agent, or Firm* — Foley & Lardner LLP

(57) ABSTRACT

The present invention is directed to antibodies and fragments thereof having binding specificity for FZD7, which preferably do not substantially interact with (bind to) other FZD family members, and methods of making said anti-FZD7 antibodies and binding fragments thereof. Another embodiment relates to antibodies and binding fragments comprising sequences of VH, VL and/or CDR polypeptides described herein. The invention also contemplates conjugates of anti-FZD7 antibodies and binding fragments. The invention further contemplates use of anti-FZD7 antibodies and binding fragments for tissue engineering. This invention also relates to a transgenic mouse expressing the epitope of anti-FZD7 antibodies and binding fragments thereof. Embodiments also pertain to use of anti-FZD7 antibodies and binding fragments (as well as the identified FZD7 epitope) for diagnosis, assessment, prevention and/or treatment of diseases and disorders associated with aberrant FZD7 expression, such as cancer. The invention further provides peptides for use in anticancer vaccines and for producing antibodies.

18 Claims, 17 Drawing Sheets

Specification includes a Sequence Listing.

(56) References Cited

OTHER PUBLICATIONS

Pode-Shakked, et al., "Resistance or sensitivity of Wilms' tumor to anti-FZD7 antibody highlights the Wnt pathway as a possible therapeutic target", Oncogene (2011) 30, pp. 1664-1680.
Reya, et al., "A role for Wnt signalling in self-renewal of haematopoietic stem cells", Nature, vol. 423, May 22, 2003, pp. 409-414.
Simmons, et al., Frizzled 7 Expression Is Positively Regulated by SIRT1 and beta-Catenin in Breast Cancer Cells, PLOS ONE, Jun. 2014, vol. 9, Issue 6, e98861, 10 pages.
Ueno, et al., "Down-regulation of frizzled-7 expression decreases survival, invasion and metastatic capabilities of colon cancer cells", British Journal of Cancer (2009) 101, pp. 1374-1381.
Vincan, et al., "Variable FZD7 Expression in Colorectal Cancers Indicates Regulation by the Tumour Microenvironment", Developmental Dynamics, 2010, 239, pp. 311-317.
Wei, et al., "Soluble Frizzled-7 receptor inhibits Wnt signaling and sensitizes hepatocellular carcinoma cells towards doxorubicin", Molecular Cancer, 2011, 10:16, 12 pages.
Willert, et al., "Wnt proteins are lipid-modified and can act as stem cell growth factors", Nature, vol. 423, May 22, 2003, pp. 448-452.
Yang, et al. "FZD7 has a critical role in cell proliferation in triple negative breast cancer", Oncogene (2011) 30, pp. 4437-4446.

* cited by examiner

FIGURE 1

FZD7-Fab-1791
Light chain
DIVMTQSPKSMSMSVGERVTLRCKASENVLNYVSWYQQKPEQSPKLLIYGASNRYTGV
PDRFTGSGSATDFTLTISSVQAEDLADYHCGQSYRYPTFGAGTKLELKRADAAPTVSI
FPPSSEQLTSGGASVVCFLNNFYPKDINVKWKIDGSERQNGVLNSWTDQDSKDSTYSM
SSTLTL TKDEYERHNSYTCEATHKTSTSPIVKSFNRNESYPYDVPDYAS (SEQ ID
NO:4)

Heavy chain
EVQPVESGGGLVQPKGSLKLSCAASGFTFNTYAMHWVRQAPGKGLEWVA**RIRSKSNNY
AKNYDDSVKDRFTISRDDSQSMLYLQMNNLKTEDTAMYYCVRENYGGRFDY**WGQGTTL
TVSSAKTTPPSVYPLAPGSAAQTNSMVTLGCLVKGYFPEPVTVTWNSGSLSSGVHTFP
AVLQSD LYTLSSSVTVPSSTWPSETVTCNVAHPASSTKVDKKIVPRDSHHHHHHH
(SEQ ID NO:5)

FZD7-Fab-1291
Light chain
DVVMSQSPSSLAVSVGEKVTMSCKSSQSLLYSSNQKNYLAWYQQKPGQSPKLLIY**WAS
TRESGVPDRFTGSGSGTDFTLTISSVKAKDLAVYYCQQYYSYP**TFGGGTKLEIKRADA
APTVSIFPPSSEQLTSGGASVVCFLNNFYPKDINVKWKIDGSERQNGVLNSWTDQDSK
DSTYSM SSTLTLTKDEYERHNSYTCEATHKTSTSPIVKSFNRNESYPYDVPDYAS
(SEQ ID NO:12)

Heavy chain
EVQLVESGGGLVKPGGSLKLSCAASGFTFSSYAMSWVRQTPEKRLEWVA**TISDGGSYT
RYPDKLKGRFTISRDNAKNNLYLQMSHLKSEDTAMYYCARVGGRRDYFDY**WGQGTTLT
VSSAKTTPPSVYPLAPGSAAQTNSMVTLGCLVKGYFPEPVTVTWNSGSLSSGVHTFPA
VLQSDL YTLSSSVTVPSSTWPSETVTCNVAHPASSTKVDKKIVPRDCHHHHHHH
(SEQ ID NO:13)

FIGURE 2 chFZD7-1791
Light chain
MDMRVPAQLLGLLLLWLPGAKCDIVMTQSPKSMSMSVGERVTLRCKASENVLNYVSW
YQQKPEQSPKLLIYGASNRYTGVPDRFTGSGSATDFTLTISSVQAEDLADYHCGQSY
RYPTFGAGTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGEC (SEQ ID NO:20)

Heavy chain
MDMRVPAQLLGLLLLWLPGAKCEVQPVESGGGLVQPKGSLKLSCAASGFTFNTYAMHW
VRQAPGKGLEWVARIRSKSNNYAKNYDDSVKDRFTISRDDSQSMLYLQMNNLKTEDTA
MYYCVRENYGGRFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPS
NTKVDKKV
EPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK
(SEQ ID NO:21)

chFZD7-1291
Light chain
MDMRVPAQLLGLLLLWLPGAKCDVVMSQSPSSLAVSVGEKVTMSCKSSQSLLYSSNQKN
YLAWYQQKPGQSPKLLIYWASTRESGVPDRFTGSGSGTDFTLTISSVKAKDLAVYYCQQ
YYSYPTFGGGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSF
NRGEC (SEQ ID NO:22)

Heavy chain
MDMRVPAQLLGLLLLWLPGAKCEVQLVESGGGLVKPGGSLKLSCAASGFTFSSYAMS
WVRQTPEKRLEWVATISDGGSYTRYPDKLKGRFTISRDNAKNNLYLQMSHLKSEDTA
MYYCARVGGRRDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKKVE
PKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLS
PGK (SEQ ID NO:23)

FIG. 3

```
Majority       MRXPGXAAXXSXLGLCALVLALLGALXXXXXAQPYHGEKGISVPDHGFCQPISIPLCTDIAYNQT
                       10        20        30        40        50        60

Human  FZD7.pro MRDPGAAAPLSSLGLCALVLALLGALSAGAGAQPYHGEKGISVPDHGFCQPISIPLCTDIAYNQT
mouse  Fzd7.pro MRGPGTAASHSPLGLCALVLALLGALPTDTRAQPYHGEKGISVPDHGFCQPISIPLCTDIAYNQT Majority       LEVHQFYPLVKVQCSPELRFFLCSMYAPVCTVLDQAIPPCRSLCERARQGCEALMNKFGFQWPER
                       90       100       110       120       130       140

Human  FZD7.pro LEVHQFYPLVKVQCSPELRFFLCSMYAPVCTVLDQAIPPCRSLCERARQGCEALMNKFGFQWPER
mouse  Fzd7.pro LEVHQFYPLVKVQCSPELRFFLCSMYAPVCTVLDQAIPPCRSLCERARQGCEALMNKFGFQWPER Majority       VGQNTSDGSGGXGGXPTAYPTAPYLPDXPFTAXXPXXSDGRGRXXFPFSCPRQLKVPPYLGYRFL
                      170       180       190       200       210       220

Human  FZD7.pro VGQNTSDGSGGPGGGPTAYPTAPYLPDLPFTALPPGASDGRGRPAFPFSCPRQLKVPPYLGYRFL
mouse  Fzd7.pro VGQNTSDGSGGAGGSPTAYPTAPYLPDPPFTAMSP--SDGRGRLSFPFSCPRQLKVPPYLGYRFL Majority       GLMYFKEEERRFARLWVGVWSVLCCASTLFTVLTYLVDMRRFSYPERPIIFLSGCYFMVAVAHVA
                      250       260       270       280       290       300

Human  FZD7.pro GLMYFKEEERRFARLWVGVWSVLCCASTLFTVLTYLVDMRRFSYPERPIIFLSGCYFMVAVAHVA
mouse  Fzd7.pro GLMYFKEEERRFARLWVGVWSVLCCASTLFTVLTYLVDMRRFSYPERPIIFLSGCYFMVAVAHVA Majority       DDGYRTVAQGTKKEGCTILFMVLYFFGMASSIWWVILSLTWFLAAGMKWGHEAIEANSQYFHLAA
                      330       340       350       360       370       380

Human  FZD7.pro DDGYRTVAQGTKKEGCTILFMVLYFFGMASSIWWVILSLTWFLAAGMKWGHEAIEANSQYFHLAA
mouse  Fzd7.pro DDGYRTVAQGTKKEGCTILFMVLYFFGMASSIWWVILSLTWFLAAGMKWGHEAIEANSQYFHLAA Majority       QVDGDLLSGVCYVGLSSVDALRGFVLAPLFVYLFIGTSFLLAGFVSLFRIRTIMKHDGTKTEKLE
                      410       420       430       440       450       460

Human  FZD7.pro QVDGDLLSGVCYVGLSSVDALRGFVLAPLFVYLFIGTSFLLAGFVSLFRIRTIMKHDGTKTEKLE
mouse  Fzd7.pro QVDGDLLSGVCYVGLSSVDALRGFVLAPLFVYLFIGTSFLLAGFVSLFRIRTIMKHDGTKTEKLE Majority       PATIVLACYFYEQAFREHWERTWLLQTCKSYAVPCPPGHFXPMSPDFTVFMIKYLMTMIVGITTG
                      490       500       510       520       530       540

Human  FZD7.pro PATIVLACYFYEQAFREHWERTWLLQTCKSYAVPCPPGHFPPMSPDFTVFMIKYLMTMIVGITTG
mouse  Fzd7.pro PATIVLACYFYEQAFREHWERTWLLQTCKSYAVPCPPGHFSPMSPDFTVFMIKYLMTMIVGITTG Majority       YHRLSHSSKGETAV
                      570

Human  FZD7.pro YHRLSHSSKGETAV
mouse  Fzd7.pro YHRLSHSSKGETAV
```

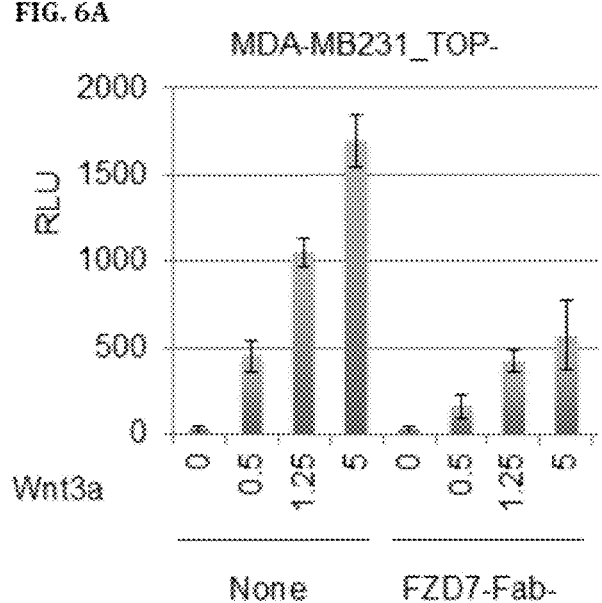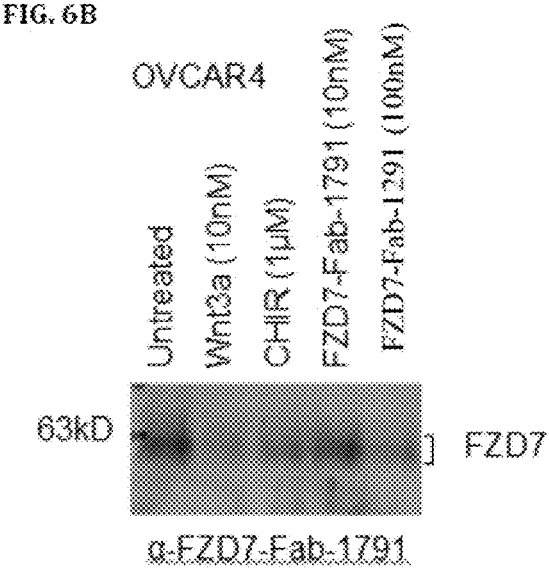

FIGURE 10
FIG. 10A
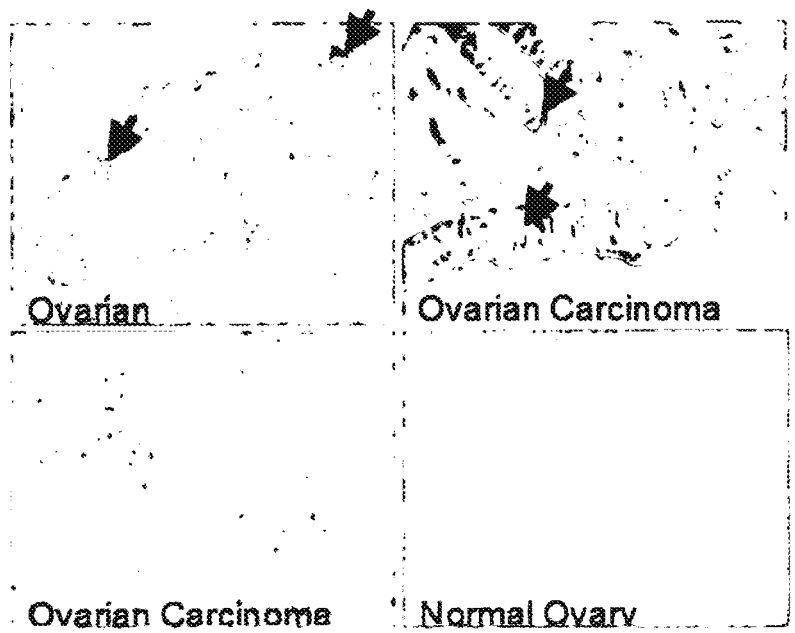
FIG. 10B
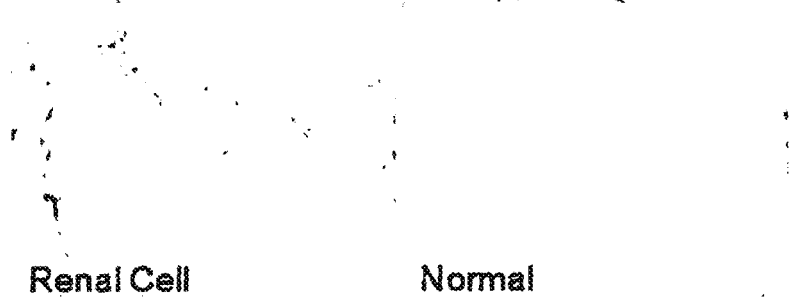

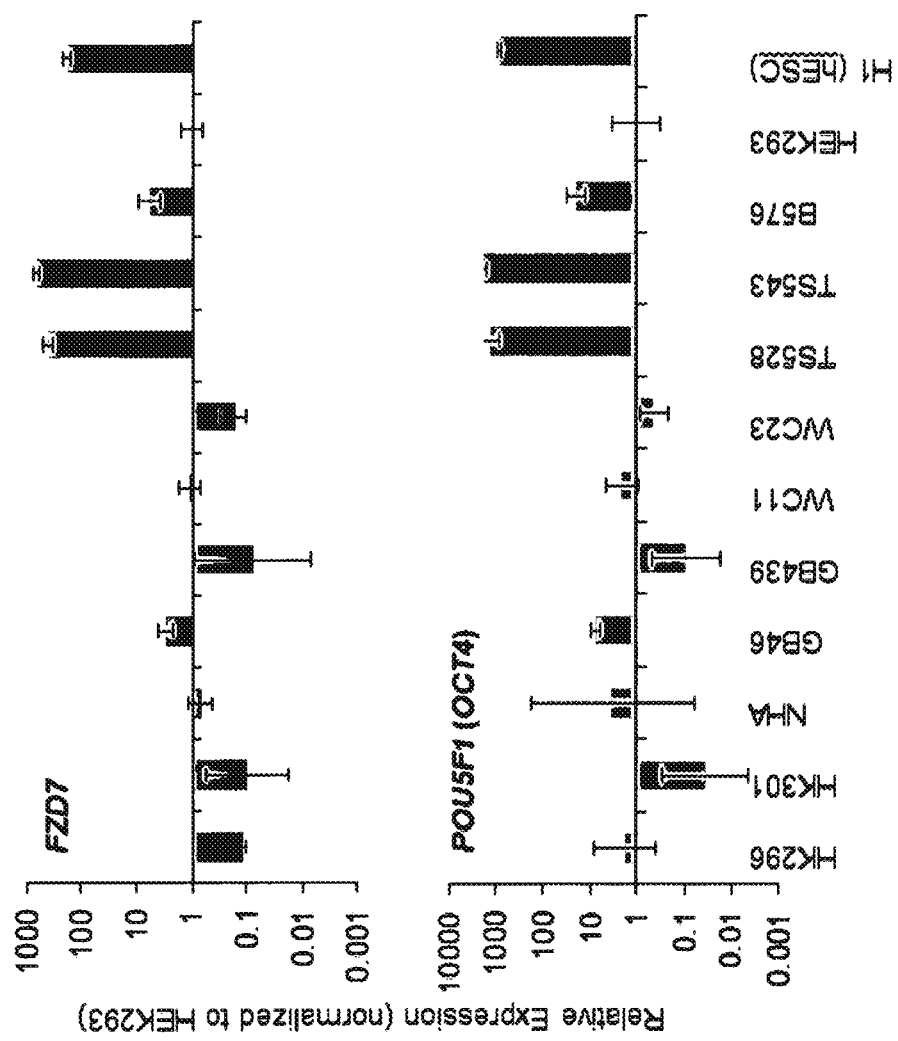

FIG. 13A   GBM cells: TS528

FIG. 14

FIG. 14A  GST-L188
GST—GSGGPGGGPTAYPTAPYLPDLPFTALPPGASDGRGRPAFPF   SEQ ID NO: 35

FIG. 14B  GST-P188
GST—GSGGPGGGPTAYPTAPYLPDPPFTALPPGASDGRGRPAFPF   SEQ ID NO: 36

α-FZD7$^{clg1791}$   α-GST

SEQUENCE LISTING

<160> NUMBER OF SEQ ID NOS: 44

<210> SEQ ID NO 1
<211> LENGTH: 469
<212> TYPE: PRT
<213> ORGANISM: Homo sapiens

<400> SEQUENCE: 1

-continued

```
Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Gly Ala
            20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
            50                  55                  60

Thr Leu Glu Val His Gln Phe Tyr Pro Leu Val Lys Val Gln Cys Ser
65                  70                  75                  80

Pro Glu Leu Arg Phe Phe Leu Cys Ser Met Tyr Ala Pro Val Cys Thr
                85                  90                  95

Val Leu Asp Gln Ala Ile Pro Pro Cys Arg Ser Leu Cys Glu Arg Ala
            100                 105                 110

Arg Gln Gly Cys Glu Ala Leu Met Asn Lys Phe Gly Phe Gln Trp Pro
            115                 120                 125

Glu Arg Val Gly Gln Asn Thr Ser Asp Gly Ser Gly Gly Pro Gly Gly
            130                 135                 140

Gly Pro Thr Ala Tyr Pro Thr Ala Pro Tyr Leu Pro Asp Leu Pro Phe
145                 150                 155                 160

Thr Ala Leu Pro Pro Gly Ala Ser Asp Gly Arg Gly Arg Pro Ala Phe
                165                 170                 175

Pro Phe Ser Cys Pro Arg Gln Leu Lys Val Pro Pro Tyr Leu Gly Tyr
            180                 185                 190

Arg Phe Leu Gly Leu Met Tyr Phe Lys Glu Glu Arg Phe Ala
            195                 200                 205

Arg Leu Trp Val Gly Val Trp Ser Val Leu Cys Cys Ala Ser Thr Leu
            210                 215                 220

Phe Thr Val Leu Thr Tyr Leu Val Asp Met Arg Arg Phe Ser Tyr Pro
225                 230                 235                 240

Glu Arg Pro Ile Ile Phe Leu Ser Gly Cys Tyr Phe Met Val Ala Val
                245                 250                 255

Ala His Val Ala Asp Asp Gly Tyr Arg Thr Val Ala Gln Gly Thr Lys
            260                 265                 270

Lys Glu Gly Cys Thr Ile Leu Phe Met Val Leu Tyr Phe Phe Gly Met
            275                 280                 285

Ala Ser Ser Ile Trp Trp Val Ile Leu Ser Leu Thr Trp Phe Leu Ala
            290                 295                 300

Ala Gly Met Lys Trp Gly His Glu Ala Ile Glu Ala Asn Ser Gln Tyr
305                 310                 315                 320

Phe His Leu Ala Ala Gln Val Asp Gly Asp Leu Leu Ser Gly Val Cys
                325                 330                 335

Tyr Val Gly Leu Ser Ser Val Asp Ala Leu Arg Gly Phe Val Leu Ala
            340                 345                 350

Pro Leu Phe Val Tyr Leu Phe Ile Gly Thr Ser Phe Leu Leu Ala Gly
            355                 360                 365

Phe Val Ser Leu Phe Arg Ile Arg Thr Ile Met Lys His Asp Gly Thr
            370                 375                 380

Lys Thr Glu Lys Leu Glu Pro Ala Thr Ile Val Leu Ala Cys Tyr Phe
385                 390                 395                 400

Tyr Glu Gln Ala Phe Arg Glu His Trp Glu Arg Thr Trp Leu Leu Gln
                405                 410                 415
```

```
Thr Cys Lys Ser Tyr Ala Val Pro Cys Pro Gly His Phe Pro Pro
                420                 425                 430

Met Ser Pro Asp Phe Thr Val Phe Met Ile Lys Tyr Leu Met Thr Met
            435                 440                 445

Ile Val Gly Ile Thr Thr Gly Tyr His Arg Leu Ser His Ser Ser Lys
        450                 455                 460

Gly Glu Thr Ala Val
465

<210> SEQ ID NO 2
<211> LENGTH: 467
<212> TYPE: PRT
<213> ORGANISM: Mus musculus

<400> SEQUENCE: 2

Met Arg Gly Pro Gly Thr Ala Ala Ser His Ser Pro Leu Gly Leu Cys
1               5                   10                  15

Ala Leu Val Leu Ala Leu Leu Gly Ala Leu Pro Thr Asp Thr Arg Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Leu Glu Val His Gln Phe Tyr Pro Leu Val Lys Val Gln Cys Ser
65                  70                  75                  80

Pro Glu Leu Arg Phe Phe Leu Cys Ser Met Tyr Ala Pro Val Cys Thr
                85                  90                  95

Val Leu Asp Gln Ala Ile Pro Pro Cys Arg Ser Leu Cys Glu Arg Ala
            100                 105                 110

Arg Gln Gly Cys Glu Ala Leu Met Asn Lys Phe Gly Phe Gln Trp Pro
        115                 120                 125

Glu Arg Val Gly Gln Asn Thr Ser Asp Gly Ser Gly Ala Gly Gly
    130                 135                 140

Ser Pro Thr Ala Tyr Pro Thr Ala Pro Tyr Leu Pro Asp Pro Pro Phe
145                 150                 155                 160

Thr Ala Met Ser Pro Ser Asp Gly Arg Gly Arg Leu Ser Phe Pro Phe
                165                 170                 175

Ser Cys Pro Arg Gln Leu Lys Val Pro Pro Tyr Leu Gly Tyr Arg Phe
            180                 185                 190

Leu Gly Leu Met Tyr Phe Lys Glu Glu Glu Arg Arg Phe Ala Arg Leu
        195                 200                 205

Trp Val Gly Val Trp Ser Val Leu Cys Cys Ala Ser Thr Leu Phe Thr
    210                 215                 220

Val Leu Thr Tyr Leu Val Asp Met Arg Arg Phe Ser Tyr Pro Glu Arg
225                 230                 235                 240

Pro Ile Ile Phe Leu Ser Gly Cys Tyr Phe Met Val Ala Val Ala His
                245                 250                 255

Val Ala Asp Asp Gly Tyr Arg Thr Val Ala Gln Gly Thr Lys Lys Glu
            260                 265                 270

Gly Cys Thr Ile Leu Phe Met Val Leu Tyr Phe Phe Gly Met Ala Ser
        275                 280                 285

Ser Ile Trp Trp Val Ile Leu Ser Leu Thr Trp Phe Leu Ala Ala Gly
    290                 295                 300

Met Lys Trp Gly His Glu Ala Ile Glu Ala Asn Ser Gln Tyr Phe His
305                 310                 315                 320
```

```
Leu Ala Ala Gln Val Asp Gly Asp Leu Leu Ser Gly Val Cys Tyr Val
                325                 330                 335

Gly Leu Ser Ser Val Asp Ala Leu Arg Gly Phe Val Leu Ala Pro Leu
            340                 345                 350

Phe Val Tyr Leu Phe Ile Gly Thr Ser Phe Leu Leu Ala Gly Phe Val
        355                 360                 365

Ser Leu Phe Arg Ile Arg Thr Ile Met Lys His Asp Gly Thr Lys Thr
    370                 375                 380

Glu Lys Leu Glu Pro Ala Thr Ile Val Leu Ala Cys Tyr Phe Tyr Glu
385                 390                 395                 400

Gln Ala Phe Arg Glu His Trp Glu Arg Thr Trp Leu Leu Gln Thr Cys
                405                 410                 415

Lys Ser Tyr Ala Val Pro Cys Pro Pro Gly His Phe Ser Pro Met Ser
            420                 425                 430

Pro Asp Phe Thr Val Phe Met Ile Lys Tyr Leu Met Thr Met Ile Val
        435                 440                 445

Gly Ile Thr Thr Gly Tyr His Arg Leu Ser His Ser Ser Lys Gly Glu
    450                 455                 460

Thr Ala Val
465

<210> SEQ ID NO 3
<211> LENGTH: 469
<212> TYPE: PRT
<213> ORGANISM: Artificial Sequence
<220> FEATURE:
<223> OTHER INFORMATION: Consensus of Human FZD7 and Mouse Fzd7
<220> FEATURE:
<221> NAME/KEY: MISC_FEATURE
<222> LOCATION: (3)..(3)
<223> OTHER INFORMATION: Xaa may be Asp or Gly
<220> FEATURE:
<221> NAME/KEY: MISC_FEATURE
<222> LOCATION: (6)..(6)
<223> OTHER INFORMATION: Xaa may be Ala or Thr
<220> FEATURE:
<221> NAME/KEY: MISC_FEATURE
<222> LOCATION: (9)..(9)
<223> OTHER INFORMATION: Xaa may be Pro or Ser
<220> FEATURE:
<221> NAME/KEY: MISC_FEATURE
<222> LOCATION: (10)..(10)
<223> OTHER INFORMATION: Xaa may be Leu or His
<220> FEATURE:
<221> NAME/KEY: MISC_FEATURE
<222> LOCATION: (12)..(12)
<223> OTHER INFORMATION: Xaa may be Ser or Pro
<220> FEATURE:
<221> NAME/KEY: MISC_FEATURE
<222> LOCATION: (27)..(27)
<223> OTHER INFORMATION: Xaa may be Ser or Pro
<220> FEATURE:
<221> NAME/KEY: MISC_FEATURE
<222> LOCATION: (28)..(28)
<223> OTHER INFORMATION: Xaa may be Ala or Thr
<220> FEATURE:
<221> NAME/KEY: MISC_FEATURE
<222> LOCATION: (29)..(29)
<223> OTHER INFORMATION: Xaa may be Gly or Asp
<220> FEATURE:
<221> NAME/KEY: MISC_FEATURE
<222> LOCATION: (30)..(30)
<223> OTHER INFORMATION: Xaa may be Ala or Thr
<220> FEATURE:
<221> NAME/KEY: MISC_FEATURE
<222> LOCATION: (31)..(31)
<223> OTHER INFORMATION: Xaa may be Gly or Arg
<220> FEATURE:
```

```
<221> NAME/KEY: MISC_FEATURE
<222> LOCATION: (142)..(142)
<223> OTHER INFORMATION: Xaa may be Pro or Ala
<220> FEATURE:
<221> NAME/KEY: MISC_FEATURE
<222> LOCATION: (145)..(145)
<223> OTHER INFORMATION: Xaa may be Gly or Ser
<220> FEATURE:
<221> NAME/KEY: MISC_FEATURE
<222> LOCATION: (158)..(158)
<223> OTHER INFORMATION: Xaa may be Leu or Pro
<220> FEATURE:
<221> NAME/KEY: MISC_FEATURE
<222> LOCATION: (163)..(163)
<223> OTHER INFORMATION: Xaa may be Leu or Met
<220> FEATURE:
<221> NAME/KEY: MISC_FEATURE
<222> LOCATION: (164)..(164)
<223> OTHER INFORMATION: Xaa may be Pro or Ser
<220> FEATURE:
<221> NAME/KEY: MISC_FEATURE
<222> LOCATION: (166)..(166)
<223> OTHER INFORMATION: Xaa may be Gly or absent
<220> FEATURE:
<221> NAME/KEY: MISC_FEATURE
<222> LOCATION: (167)..(167)
<223> OTHER INFORMATION: Xaa may be Ala or absent
<220> FEATURE:
<221> NAME/KEY: MISC_FEATURE
<222> LOCATION: (174)..(174)
<223> OTHER INFORMATION: Xaa may be Pro or Leu
<220> FEATURE:
<221> NAME/KEY: MISC_FEATURE
<222> LOCATION: (175)..(175)
<223> OTHER INFORMATION: Xaa may be Ala or Ser
<220> FEATURE:
<221> NAME/KEY: MISC_FEATURE
<222> LOCATION: (431)..(431)
<223> OTHER INFORMATION: Xaa may be Pro Ser

<400> SEQUENCE: 3

Met Arg Xaa Pro Gly Xaa Ala Ala Xaa Xaa Ser Xaa Leu Gly Leu Cys
 1               5                  10                  15

Ala Leu Val Leu Ala Leu Leu Gly Ala Leu Xaa Xaa Xaa Xaa Xaa Ala
             20                  25                  30

Gln Pro Tyr His Gly Glu Lys Gly Ile Ser Val Pro Asp His Gly Phe
         35                  40                  45

Cys Gln Pro Ile Ser Ile Pro Leu Cys Thr Asp Ile Ala Tyr Asn Gln
     50                  55                  60

Thr Leu Glu Val His Gln Phe Tyr Pro Leu Val Lys Val Gln Cys Ser
 65                  70                  75                  80

Pro Glu Leu Arg Phe Phe Leu Cys Ser Met Tyr Cys Ala Pro Val Cys
                 85                  90                  95

Thr Val Leu Asp Gln Ala Ile Pro Pro Cys Arg Ser Leu Cys Glu Arg
            100                 105                 110

Ala Arg Gln Gly Cys Glu Ala Leu Met Asn Lys Phe Gly Phe Gln Trp
        115                 120                 125

Pro Glu Arg Val Gly Gln Asn Thr Ser Asp Ser Gly Xaa Gly Gly
    130                 135                 140

Xaa Pro Thr Ala Tyr Pro Thr Ala Pro Tyr Leu Pro Asp Xaa Pro Phe
145                 150                 155                 160

Thr Ala Xaa Xaa Pro Xaa Xaa Ser Asp Gly Arg Gly Arg Xaa Xaa Phe
                165                 170                 175

Pro Phe Ser Cys Pro Arg Gln Leu Lys Val Pro Pro Tyr Leu Gly Tyr
            180                 185                 190

Arg Phe Leu Gly Leu Met Tyr Phe Lys Glu Glu Arg Arg Phe Ala
```

```
                195                 200                 205
Arg Leu Trp Val Gly Val Trp Ser Val Leu Cys Cys Ala Ser Thr Leu
210                 215                 220

Phe Thr Val Leu Thr Tyr Leu Val Asp Met Arg Arg Phe Ser Tyr Pro
225                 230                 235                 240

Glu Arg Pro Ile Ile Phe Leu Ser Gly Cys Tyr Phe Met Val Ala Val
                245                 250                 255

Ala His Val Ala Asp Asp Gly Tyr Arg Thr Val Ala Gln Gly Thr Lys
                260                 265                 270

Lys Glu Gly Cys Thr Ile Leu Phe Met Val Leu Tyr Phe Phe Gly Met
275                 280                 285

Ala Ser Ser Ile Trp Trp Val Ile Leu Ser Leu Thr Trp Phe Leu Ala
290                 295                 300

Ala Gly Met Lys Trp Gly His Glu Ala Ile Glu Ala Asn Ser Gln Tyr
305                 310                 315                 320

Phe His Leu Ala Ala Gln Val Asp Gly Asp Leu Leu Ser Gly Val Cys
                325                 330                 335

Tyr Val Gly Leu Ser Ser Val Asp Ala Leu Arg Gly Phe Val Leu Ala
                340                 345                 350

Pro Leu Phe Val Tyr Leu Phe Ile Gly Thr Ser Phe Leu Leu Ala Gly
                355                 360                 365

Phe Val Ser Leu Phe Arg Ile Arg Thr Ile Met Lys His Asp Gly Thr
370                 375                 380

Lys Thr Glu Lys Leu Glu Pro Ala Thr Ile Val Leu Ala Cys Tyr Phe
385                 390                 395                 400

Tyr Glu Gln Ala Phe Arg Glu His Trp Glu Arg Thr Trp Leu Leu Gln
                405                 410                 415

Thr Cys Lys Ser Tyr Ala Val Pro Cys Pro Gly His Phe Xaa Pro
                420                 425                 430

Met Ser Pro Asp Phe Thr Val Phe Met Ile Lys Tyr Leu Met Thr Met
                435                 440                 445

Ile Val Gly Ile Thr Thr Gly Tyr His Arg Leu Ser His Ser Ser Lys
450                 455                 460

Gly Glu Thr Ala Val
465

<210> SEQ ID NO 4
<211> LENGTH: 223
<212> TYPE: PRT
<213> ORGANISM: Artificial Sequence
<220> FEATURE:
<223> OTHER INFORMATION: FZD7-Fab-1791 Light chain

<400> SEQUENCE: 4

Asp Ile Val Met Thr Gln Ser Pro Lys Ser Met Ser Met Ser Val Gly
1               5                   10                  15

Glu Arg Val Thr Leu Arg Cys Lys Ala Ser Glu Asn Val Leu Asn Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Arg Tyr Pro Thr
```

```
                    85                  90                  95
Phe Gly Ala Gly Thr Lys Leu Glu Leu Lys Arg Ala Asp Ala Ala Pro
                100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
            195                 200                 205

Asn Arg Asn Glu Ser Tyr Pro Tyr Asp Val Pro Asp Tyr Ala Ser
        210                 215                 220

<210> SEQ ID NO 5
<211> LENGTH: 229
<212> TYPE: PRT
<213> ORGANISM: Artificial Sequence
<220> FEATURE:
<223> OTHER INFORMATION: FZD7-Fab-1791 Heavy chain

<400> SEQUENCE: 5

Glu Val Gln Pro Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Asn Asn Tyr Ala Lys Asn Tyr Asp Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Glu Asn Tyr Gly Gly Arg Phe Asp Tyr Trp Gly Gln
                100                 105                 110

Gly Thr Thr Leu Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Ser His His
        210                 215                 220

His His His His His
```

<210> SEQ ID NO 6
<211> LENGTH: 11
<212> TYPE: PRT
<213> ORGANISM: Artificial Sequence
<220> FEATURE:
<223> OTHER INFORMATION: CDR1 of FZD7-Fab-1791 Light chain

<400> SEQUENCE: 6

Lys Ala Ser Glu Asn Val Leu Asn Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR2 of FZD7-Fab-1791 Light chain

<400> SEQUENCE: 7

Gly Ala Ser Asn Arg Tyr Thr
1               5

<210> SEQ ID NO 8
<211> LENGTH: 7
<212> TYPE: PRT
<213> ORGANISM: Artificial Sequence
<220> FEATURE:
<223> OTHER INFORMATION: CDR3 of FZD7-Fab-1791 Light chain

<400> SEQUENCE: 8

Gly Gln Ser Tyr Arg Tyr Pro
1               5

<210> SEQ ID NO 9
<211> LENGTH: 5
<212> TYPE: PRT
<213> ORGANISM: Artificial Sequence
<220> FEATURE:
<223> OTHER INFORMATION: CDR1 of FZD7-Fab-1791 Heavy chain

<400> SEQUENCE: 9

Thr Tyr Ala Met His
1               5

<210> SEQ ID NO 10
<211> LENGTH: 19
<212> TYPE: PRT
<213> ORGANISM: Artificial Sequence
<220> FEATURE:
<223> OTHER INFORMATION: CDR2 of FZD7-Fab-1791 Heavy chain

<400> SEQUENCE: 10

Arg Ile Arg Ser Lys Ser Asn Asn Tyr Ala Lys Asn Tyr Asp Asp Ser
1               5                   10                  15

Val Lys Asp

<210> SEQ ID NO 11
<211> LENGTH: 9
<212> TYPE: PRT
<213> ORGANISM: Artificial Sequence
<220> FEATURE:
<223> OTHER INFORMATION: CDR3 of FZD7-Fab-1791 Heavy chain

<400> SEQUENCE: 11

```
Glu Asn Tyr Gly Gly Arg Phe Asp Tyr
1               5
```

<210> SEQ ID NO 12
<211> LENGTH: 229
<212> TYPE: PRT
<213> ORGANISM: Artificial Sequence
<220> FEATURE:
<223> OTHER INFORMATION: FZD7-Fab-1291 Light chain

<400> SEQUENCE: 12

```
Asp Val Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Lys Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Ser Tyr Pro Tyr Asp Val
    210                 215                 220

Pro Asp Tyr Ala Ser
225
```

<210> SEQ ID NO 13
<211> LENGTH: 228
<212> TYPE: PRT
<213> ORGANISM: Artificial Sequence
<220> FEATURE:
<223> OTHER INFORMATION: FZD7-Fab-1291 Heavy chain

<400> SEQUENCE: 13

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Tyr Thr Arg Tyr Pro Asp Lys Leu
    50                  55                  60
```

```
Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Met Tyr Tyr Cys
                 85                  90                  95

Ala Arg Val Gly Gly Arg Arg Asp Tyr Phe Asp Tyr Trp Gly Gln Gly
            100                 105                 110

Thr Thr Leu Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys His His His
    210                 215                 220

His His His His
225

<210> SEQ ID NO 14
<211> LENGTH: 18
<212> TYPE: PRT
<213> ORGANISM: Artificial Sequence
<220> FEATURE:
<223> OTHER INFORMATION: CDR1 of FZD7-Fab-1291 Light chain

<400> SEQUENCE: 14

Lys Ser Ser Gln Ser Leu Leu Tyr Ser Ser Asn Gln Lys Asn Tyr Leu
1               5                   10                  15

Ala Trp

<210> SEQ ID NO 15
<211> LENGTH: 7
<212> TYPE: PRT
<213> ORGANISM: Artificial Sequence
<220> FEATURE:
<223> OTHER INFORMATION: CDR2 of FZD7-Fab-1291 Light chain

<400> SEQUENCE: 15

Trp Ala Ser Thr Arg Glu Ser
1               5

<210> SEQ ID NO 16
<211> LENGTH: 7
<212> TYPE: PRT
<213> ORGANISM: Artificial Sequence
<220> FEATURE:
<223> OTHER INFORMATION: CDR3 of FZD7-Fab-1291 Light chain

<400> SEQUENCE: 16

Gln Gln Tyr Tyr Ser Tyr Pro
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: CDR1 of FZD7-Fab-1291 Heavy chain

<400> SEQUENCE: 17

Ser Tyr Ala Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: CDR2 of FZD7-Fab-1291 Heavy chain

<400> SEQUENCE: 18

Thr Ile Ser Asp Gly Gly Ser Tyr Thr Arg Tyr Pro Asp Lys Leu Lys
1               5                   10                  15

Gly

<210> SEQ ID NO 19
<211> LENGTH: 10
<212> TYPE: PRT
<213> ORGANISM: Artificial Sequence
<220> FEATURE:
<223> OTHER INFORMATION: CDR3 of FZD7-Fab-1291 Heavy chain

<400> SEQUENCE: 19

Val Gly Gly Arg Arg Asp Tyr Phe Asp Tyr
1               5                   10

<210> SEQ ID NO 20
<211> LENGTH: 235
<212> TYPE: PRT
<213> ORGANISM: Artificial Sequence
<220> FEATURE:
<223> OTHER INFORMATION: chFZD7-1791 Light chain

<400> SEQUENCE: 20

Met Asp Met Arg Val Pro Ala Gln Leu Leu Gly Leu Leu Leu Leu Trp
1               5                   10                  15

Leu Pro Gly Ala Lys Cys Asp Ile Val Met Thr Gln Ser Pro Lys Ser
                20                  25                  30

Met Ser Met Ser Val Gly Glu Arg Val Thr Leu Arg Cys Lys Ala Ser
            35                  40                  45

Glu Asn Val Leu Asn Tyr Val Ser Trp Tyr Gln Gln Lys Pro Glu Gln
        50                  55                  60

Ser Pro Lys Leu Leu Ile Tyr Gly Ala Ser Asn Arg Tyr Thr Gly Val
65                  70                  75                  80

Pro Asp Arg Phe Thr Gly Ser Gly Ser Ala Thr Asp Phe Thr Leu Thr
                85                  90                  95

Ile Ser Ser Val Gln Ala Glu Asp Leu Ala Asp Tyr His Cys Gly Gln
            100                 105                 110

Ser Tyr Arg Tyr Pro Thr Phe Gly Ala Gly Thr Lys Leu Glu Leu Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Cys Leu Leu Asn Asn Phe
145                 150                 155                 160

Tyr Pro Arg Glu Ala Lys Val Gln Trp Lys Val Asp Asn Ala Leu Gln
                165                 170                 175
```

```
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 21
<211> LENGTH: 472
<212> TYPE: PRT
<213> ORGANISM: Artificial Sequence
<220> FEATURE:
<223> OTHER INFORMATION: chFZD7-1791 Heavy chain

<400> SEQUENCE: 21

Met Asp Met Arg Val Pro Ala Gln Leu Leu Gly Leu Leu Leu Leu Trp
1               5                  10                  15

Leu Pro Gly Ala Lys Cys Glu Val Gln Pro Val Glu Ser Gly Gly Gly
            20                  25                  30

Leu Val Gln Pro Lys Gly Ser Leu Lys Leu Ser Cys Ala Ala Ser Gly
        35                  40                  45

Phe Thr Phe Asn Thr Tyr Ala Met His Trp Val Arg Gln Ala Pro Gly
    50                  55                  60

Lys Gly Leu Glu Trp Val Ala Arg Ile Arg Ser Lys Ser Asn Asn Tyr
65                  70                  75                  80

Ala Lys Asn Tyr Asp Asp Ser Val Lys Asp Arg Phe Thr Ile Ser Arg
                85                  90                  95

Asp Asp Ser Gln Ser Met Leu Tyr Leu Gln Met Asn Asn Leu Lys Thr
            100                 105                 110

Glu Asp Thr Ala Met Tyr Tyr Cys Val Arg Glu Asn Tyr Gly Gly Arg
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300
```

```
Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 22
<211> LENGTH: 241
<212> TYPE: PRT
<213> ORGANISM: Artificial Sequence
<220> FEATURE:
<223> OTHER INFORMATION: chFZD7-1291 Light chain

<400> SEQUENCE: 22

Met Asp Met Arg Val Pro Ala Gln Leu Leu Gly Leu Leu Leu Leu Trp
1               5                   10                  15

Leu Pro Gly Ala Lys Cys Asp Val Val Met Ser Gln Ser Pro Ser Ser
            20                  25                  30

Leu Ala Val Ser Val Gly Glu Lys Val Thr Met Ser Cys Lys Ser Ser
        35                  40                  45

Gln Ser Leu Leu Tyr Ser Ser Asn Gln Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Lys Ala Lys Asp Leu Ala
            100                 105                 110

Val Tyr Tyr Cys Gln Gln Tyr Tyr Ser Tyr Pro Thr Phe Gly Gly Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190
```

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 23
<211> LENGTH: 471
<212> TYPE: PRT
<213> ORGANISM: Artificial Sequence
<220> FEATURE:
<223> OTHER INFORMATION: chFZD7-1291 Heavy chain

<400> SEQUENCE: 23

Met Asp Met Arg Val Pro Ala Gln Leu Leu Gly Leu Leu Leu Leu Trp
1               5                   10                  15

Leu Pro Gly Ala Lys Cys Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Thr Phe Ser Ser Tyr Ala Met Ser Trp Val Arg Gln Thr Pro Glu
    50                  55                  60

Lys Arg Leu Glu Trp Val Ala Thr Ile Ser Asp Gly Gly Ser Tyr Thr
65                  70                  75                  80

Arg Tyr Pro Asp Lys Leu Lys Gly Arg Phe Thr Ile Ser Arg Asp Asn
                85                  90                  95

Ala Lys Asn Asn Leu Tyr Leu Gln Met Ser His Leu Lys Ser Glu Asp
            100                 105                 110

Thr Ala Met Tyr Tyr Cys Ala Arg Val Gly Gly Arg Arg Asp Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
        340                 345                 350

Pro Ala Pro Ile Glu Lys Thr Ile Ser Lys Ala Lys Gly Gln Pro Arg
    355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
    435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 24
<211> LENGTH: 36
<212> TYPE: PRT
<213> ORGANISM: Artificial Sequence
<220> FEATURE:
<223> OTHER INFORMATION: hFZD7

<400> SEQUENCE: 24

Gly Pro Gly Gly Gly Pro Thr Ala Tyr Pro Thr Ala Pro Tyr Leu Pro
1               5                   10                  15

Asp Leu Pro Phe Thr Ala Leu Pro Pro Gly Ala Ser Asp Gly Arg Gly
            20                  25                  30

Arg Pro Ala Phe
        35

<210> SEQ ID NO 25
<211> LENGTH: 34
<212> TYPE: PRT
<213> ORGANISM: Artificial Sequence
<220> FEATURE:
<223> OTHER INFORMATION: mFzd7

<400> SEQUENCE: 25

Gly Ala Gly Gly Ser Pro Thr Ala Tyr Pro Thr Ala Pro Tyr Leu Pro
1               5                   10                  15

Asp Pro Pro Phe Thr Ala Met Ser Pro Ser Asp Gly Arg Gly Arg Leu
            20                  25                  30

Ser Phe

<210> SEQ ID NO 26
<211> LENGTH: 36
<212> TYPE: PRT
<213> ORGANISM: Artificial Sequence
<220> FEATURE:
<223> OTHER INFORMATION: humanized mFzd7

<400> SEQUENCE: 26

Gly Pro Gly Gly Gly Pro Thr Ala Tyr Pro Thr Ala Pro Tyr Leu Pro
1               5                   10                  15

Asp Leu Pro Phe Thr Ala Leu Pro Pro Gly Ala Ser Asp Gly Arg Gly
            20                  25                  30

Arg Pro Ala Phe
        35

<210> SEQ ID NO 27
<211> LENGTH: 36
<212> TYPE: PRT
<213> ORGANISM: Artificial Sequence
<220> FEATURE:
<223> OTHER INFORMATION: hFZD7-3P

<400> SEQUENCE: 27

Gly Ala Gly Gly Gly Pro Thr Ala Tyr Pro Thr Ala Pro Tyr Leu Pro
1               5                   10                  15

Asp Leu Pro Phe Thr Ala Leu Ser Pro Gly Ala Ser Asp Gly Arg Gly
            20                  25                  30

Arg Leu Ala Phe
        35

<210> SEQ ID NO 28
<211> LENGTH: 36
<212> TYPE: PRT
<213> ORGANISM: Artificial Sequence
<220> FEATURE:
<223> OTHER INFORMATION: mFzd7-GA

<400> SEQUENCE: 28

Gly Ala Gly Gly Ser Pro Thr Ala Tyr Pro Thr Ala Pro Tyr Leu Pro
1               5                   10                  15

Asp Pro Pro Phe Thr Ala Met Ser Pro Gly Ala Ser Asp Gly Arg Gly
            20                  25                  30

Arg Leu Ser Phe
        35

<210> SEQ ID NO 29
<211> LENGTH: 36
<212> TYPE: PRT
<213> ORGANISM: Artificial Sequence
<220> FEATURE:
<223> OTHER INFORMATION: hFZD7-LP to MS

<400> SEQUENCE: 29

Gly Pro Gly Gly Gly Pro Thr Ala Tyr Pro Thr Ala Pro Tyr Leu Pro
1               5                   10                  15

Asp Leu Pro Phe Thr Ala Met Ser Pro Gly Ala Ser Asp Gly Arg Gly
            20                  25                  30

Arg Pro Ala Phe
        35

<210> SEQ ID NO 30
<211> LENGTH: 34
<212> TYPE: PRT
<213> ORGANISM: Artificial Sequence
<220> FEATURE:
<223> OTHER INFORMATION: hFZD7-LPPGA to MSP

<400> SEQUENCE: 30

Gly Pro Gly Gly Gly Pro Thr Ala Tyr Pro Thr Ala Pro Tyr Leu Pro
1               5                   10                  15

```
Asp Leu Pro Phe Thr Ala Met Ser Pro Ser Asp Gly Arg Gly Arg Pro
            20                  25                  30

Ala Phe

<210> SEQ ID NO 31
<211> LENGTH: 36
<212> TYPE: PRT
<213> ORGANISM: Artificial Sequence
<220> FEATURE:
<223> OTHER INFORMATION: hFZD7-PA to LS

<400> SEQUENCE: 31

Gly Pro Gly Gly Gly Pro Thr Ala Tyr Pro Thr Ala Pro Tyr Leu Pro
1               5                   10                  15

Asp Leu Pro Phe Thr Ala Leu Pro Pro Gly Ala Ser Asp Gly Arg Gly
            20                  25                  30

Arg Leu Ser Phe
        35

<210> SEQ ID NO 32
<211> LENGTH: 36
<212> TYPE: PRT
<213> ORGANISM: Artificial Sequence
<220> FEATURE:
<223> OTHER INFORMATION: hFZD7-PGGG to AGGS

<400> SEQUENCE: 32

Gly Ala Gly Gly Ser Pro Thr Ala Tyr Pro Thr Ala Pro Tyr Leu Pro
1               5                   10                  15

Asp Leu Pro Phe Thr Ala Leu Pro Pro Gly Ala Ser Asp Gly Arg Gly
            20                  25                  30

Arg Pro Ala Phe
        35

<210> SEQ ID NO 33
<211> LENGTH: 36
<212> TYPE: PRT
<213> ORGANISM: Artificial Sequence
<220> FEATURE:
<223> OTHER INFORMATION: hFZD7-L188P

<400> SEQUENCE: 33

Gly Ala Gly Gly Ser Pro Thr Ala Tyr Pro Thr Ala Pro Tyr Leu Pro
1               5                   10                  15

Asp Pro Pro Phe Thr Ala Leu Pro Pro Gly Ala Ser Asp Gly Arg Gly
            20                  25                  30

Arg Pro Ala Phe
        35

<210> SEQ ID NO 34
<211> LENGTH: 34
<212> TYPE: PRT
<213> ORGANISM: Artificial Sequence
<220> FEATURE:
<223> OTHER INFORMATION: mFzd7-P188L

<400> SEQUENCE: 34

Gly Ala Gly Gly Ser Pro Thr Ala Tyr Pro Thr Ala Pro Tyr Leu Pro
1               5                   10                  15

Asp Leu Pro Phe Thr Ala Met Ser Pro Ser Asp Gly Arg Gly Arg Leu
            20                  25                  30
```

```
<210> SEQ ID NO 35
<211> LENGTH: 41
<212> TYPE: PRT
<213> ORGANISM: Artificial Sequence
<220> FEATURE:
<223> OTHER INFORMATION: FZD7 wildtype fragment

<400> SEQUENCE: 35

Gly Ser Gly Gly Pro Gly Gly Gly Pro Thr Ala Tyr Pro Thr Ala Pro
1               5                   10                  15

Tyr Leu Pro Asp Leu Pro Phe Thr Ala Leu Pro Pro Gly Ala Ser Asp
                20                  25                  30

Gly Arg Gly Arg Pro Ala Phe Pro Phe
            35                  40

<210> SEQ ID NO 36
<211> LENGTH: 41
<212> TYPE: PRT
<213> ORGANISM: Artificial Sequence
<220> FEATURE:
<223> OTHER INFORMATION: FZD7 mutant fragment

<400> SEQUENCE: 36

Gly Ser Gly Gly Pro Gly Gly Gly Pro Thr Ala Tyr Pro Thr Ala Pro
1               5                   10                  15

Tyr Leu Pro Asp Pro Pro Phe Thr Ala Leu Pro Pro Gly Ala Ser Asp
                20                  25                  30

Gly Arg Gly Arg Pro Ala Phe Pro Phe
            35                  40

<210> SEQ ID NO 37
<211> LENGTH: 132
<212> TYPE: DNA
<213> ORGANISM: Artificial Sequence
<220> FEATURE:
<223> OTHER INFORMATION: CRISPR/Cas9 Repair Oligo

<400> SEQUENCE: 37
gacggctccg ggggcgcggg cggcagtccc accgcctacc ctactgctcc ctacctgcca      60
gatctacctt tcactgcgat gtccccctca gatggcagag gccgcttgtc tttcccttc     120 tcgtgtccgc gc                                                        132

<210> SEQ ID NO 38
<211> LENGTH: 18
<212> TYPE: DNA
<213> ORGANISM: Artificial Sequence
<220> FEATURE:
<223> OTHER INFORMATION: PCR Primer (Forward)

<400> SEQUENCE: 38
tggggcagaa cacgtccg                                                   18

<210> SEQ ID NO 39
<211> LENGTH: 20
<212> TYPE: DNA
<213> ORGANISM: Artificial Sequence
<220> FEATURE:
<223> OTHER INFORMATION: PCR Primer (Reverse)

<400> SEQUENCE: 39
gaagagcgtc gaggcgcagc                                                 20
```

Ser Phe (at top, continuation of prior sequence)

<210> SEQ ID NO 40
<211> LENGTH: 20
<212> TYPE: DNA
<213> ORGANISM: Artificial Sequence
<220> FEATURE:
<223> OTHER INFORMATION: Sequencing Primer

<400> SEQUENCE: 40
gctcacctag gaagcggtag                                               20

<210> SEQ ID NO 41
<211> LENGTH: 138
<212> TYPE: DNA
<213> ORGANISM: Artificial Sequence
<220> FEATURE:
<223> OTHER INFORMATION: Oligo sequence to generate peptide with L188

<400> SEQUENCE: 41
gaattccggc tccgggggcc caggcggcgg ccccactgcc taccctaccg cgccctacct   60
gccggacctg cccttcaccg cgctgccccc gggggcctca gatggcaggg ggcgtcccgc  120
cttccccttc tcctcgag                                                138

<210> SEQ ID NO 42
<211> LENGTH: 138
<212> TYPE: DNA
<213> ORGANISM: Artificial Sequence
<220> FEATURE:
<223> OTHER INFORMATION: Oligo sequence to generate peptide with P188

<400> SEQUENCE: 42
gaattccggc tccgggggcc caggcggcgg ccccactgcc taccctaccg cgccctacct   60
gccggacccg cccttcaccg cgctgccccc gggggcctca gatggcaggg ggcgtcccgc  120
cttccccttc tcctcgag                                                138

<210> SEQ ID NO 43
<211> LENGTH: 542
<212> TYPE: PRT
<213> ORGANISM: Homo sapiens

<400> SEQUENCE: 43

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
                20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
                100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly Gly Pro Gly Gly Gly Pro
    130                 135                 140

Thr Ala Tyr Pro Thr Ala Pro Tyr Leu Pro Asp Leu Pro Phe Thr Ala
145                 150                 155                 160

Leu Pro Pro Gly Ala Ser Asp Gly Arg Gly Arg Pro Ala Phe Pro Phe
            165                 170                 175

Ser Cys Pro Arg Gln Leu Lys Val Pro Pro Tyr Leu Gly Tyr Arg Phe
            180                 185                 190

Leu Gly Glu Arg Asp Cys Gly Ala Pro Cys Glu Pro Gly Arg Ala Asn
            195                 200                 205

Gly Leu Met Tyr Phe Lys Glu Glu Arg Arg Phe Ala Arg Leu Trp
        210                 215                 220

Val Gly Val Trp Ser Val Leu Cys Cys Ala Ser Thr Leu Phe Thr Val
225                 230                 235                 240

Leu Thr Tyr Leu Val Asp Met Arg Arg Phe Ser Tyr Pro Glu Arg Pro
                245                 250                 255

Ile Ile Phe Leu Ser Gly Cys Tyr Phe Met Val Ala Val Ala His Val
                260                 265                 270

Ala Gly Phe Leu Leu Glu Asp Arg Ala Val Cys Val Glu Arg Phe Ser
            275                 280                 285

Asp Asp Gly Tyr Arg Thr Val Ala Gln Gly Thr Lys Lys Glu Gly Cys
290                 295                 300

Thr Ile Leu Phe Met Val Leu Tyr Phe Phe Gly Met Ala Ser Ser Ile
305                 310                 315                 320

Trp Trp Val Ile Leu Ser Leu Thr Trp Phe Leu Ala Ala Gly Met Lys
                325                 330                 335

Trp Gly His Glu Ala Ile Glu Ala Asn Ser Gln Tyr Phe His Leu Ala
            340                 345                 350

Ala Trp Ala Val Pro Ala Val Lys Thr Ile Thr Ile Leu Ala Met Gly
            355                 360                 365

Gln Val Asp Gly Asp Leu Leu Ser Gly Val Cys Tyr Val Gly Leu Ser
370                 375                 380

Ser Val Asp Ala Leu Arg Gly Phe Val Leu Ala Pro Leu Phe Val Tyr
385                 390                 395                 400

Leu Phe Ile Gly Thr Ser Phe Leu Leu Ala Gly Phe Val Ser Leu Phe
                405                 410                 415

Arg Ile Arg Thr Ile Met Lys His Asp Gly Thr Lys Thr Glu Lys Leu
                420                 425                 430

Glu Lys Leu Met Val Arg Ile Gly Val Phe Ser Val Leu Tyr Thr Val
            435                 440                 445

Pro Ala Thr Ile Val Leu Ala Cys Tyr Phe Tyr Glu Gln Ala Phe Arg
            450                 455                 460

Glu His Trp Glu Arg Thr Trp Leu Leu Gln Thr Cys Lys Ser Tyr Ala
465                 470                 475                 480

Val Pro Cys Pro Pro Gly His Phe Pro Pro Met Ser Pro Asp Phe Thr
            485                 490                 495

Val Phe Met Ile Lys Tyr Leu Met Thr Met Ile Val Gly Ile Thr Thr
                500                 505                 510

Gly Phe Trp Ile Trp Ser Gly Lys Thr Leu Gln Ser Trp Arg Arg Phe
            515                 520                 525

Tyr His Arg Leu Ser His Ser Ser Lys Gly Glu Thr Ala Val
            530                 535                 540

<210> SEQ ID NO 44
<211> LENGTH: 540

<212> TYPE: PRT
<213> ORGANISM: Mus musculus

<400> SEQUENCE: 44

```
Gln Pro Tyr His Gly Glu Lys Gly Ile Ser Val Pro Asp His Gly Phe
1               5                   10                  15
Cys Gln Pro Ile Ser Ile Pro Leu Cys Thr Asp Ile Ala Tyr Asn Gln
            20                  25                  30
Thr Ile Leu Pro Asn Leu Leu Gly His Thr Asn Gln Glu Asp Ala Gly
        35                  40                  45
Leu Glu Val His Gln Phe Tyr Pro Leu Val Lys Val Gln Cys Ser Pro
    50                  55                  60
Glu Leu Arg Phe Phe Leu Cys Ser Met Tyr Ala Pro Val Cys Thr Val
65                  70                  75                  80
Leu Asp Gln Ala Ile Pro Pro Cys Arg Ser Leu Cys Glu Arg Ala Arg
                85                  90                  95
Gln Gly Cys Glu Ala Leu Met Asn Lys Phe Gly Phe Gln Trp Pro Glu
            100                 105                 110
Arg Leu Arg Cys Glu Asn Phe Pro Val His Gly Ala Gly Glu Ile Cys
        115                 120                 125
Val Gly Gln Asn Thr Ser Asp Gly Ser Gly Ala Gly Gly Ser Pro
    130                 135                 140
Thr Ala Tyr Pro Thr Ala Pro Tyr Leu Pro Asp Pro Pro Phe Thr Ala
145                 150                 155                 160
Met Ser Pro Ser Asp Gly Arg Gly Arg Leu Ser Phe Pro Phe Ser Cys
                165                 170                 175
Pro Arg Gln Leu Lys Val Pro Pro Tyr Leu Gly Tyr Arg Phe Leu Gly
            180                 185                 190
Glu Arg Asp Cys Gly Ala Pro Cys Glu Pro Gly Arg Ala Asn Gly Leu
        195                 200                 205
Met Tyr Phe Lys Glu Glu Glu Arg Arg Phe Ala Arg Leu Trp Val Gly
    210                 215                 220
Val Trp Ser Val Leu Cys Cys Ala Ser Thr Leu Phe Thr Val Leu Thr
225                 230                 235                 240
Tyr Leu Val Asp Met Arg Arg Phe Ser Tyr Pro Glu Arg Pro Ile Ile
                245                 250                 255
Phe Leu Ser Gly Cys Tyr Phe Met Val Ala Val Ala His Val Ala Gly
            260                 265                 270
Phe Leu Leu Glu Asp Arg Ala Val Cys Val Glu Arg Phe Ser Asp Asp
        275                 280                 285
Gly Tyr Arg Thr Val Ala Gln Gly Thr Lys Lys Glu Gly Cys Thr Ile
    290                 295                 300
Leu Phe Met Val Leu Tyr Phe Gly Met Ala Ser Ser Ile Trp Trp
305                 310                 315                 320
Val Ile Leu Ser Leu Thr Trp Phe Leu Ala Ala Gly Met Lys Trp Gly
                325                 330                 335
His Glu Ala Ile Glu Ala Asn Ser Gln Tyr Phe His Leu Ala Ala Trp
            340                 345                 350
Ala Val Pro Ala Val Lys Thr Ile Thr Ile Leu Ala Met Gly Gln Val
        355                 360                 365
Asp Gly Asp Leu Leu Ser Gly Val Cys Tyr Val Gly Leu Ser Ser Val
    370                 375                 380
Asp Ala Leu Arg Gly Phe Val Leu Ala Pro Leu Phe Val Tyr Leu Phe
385                 390                 395                 400
```

-continued

```
Ile Gly Thr Ser Phe Leu Leu Ala Gly Phe Val Ser Leu Phe Arg Ile
            405                 410                 415

Arg Thr Ile Met Lys His Asp Gly Thr Lys Thr Glu Lys Leu Glu Lys
            420                 425                 430

Leu Met Val Arg Ile Gly Val Phe Ser Val Leu Tyr Thr Val Pro Ala
        435                 440                 445

Thr Ile Val Leu Ala Cys Tyr Phe Tyr Glu Gln Ala Phe Arg Glu His
        450                 455                 460

Trp Glu Arg Thr Trp Leu Leu Gln Thr Cys Lys Ser Tyr Ala Val Pro
465                 470                 475                 480

Cys Pro Pro Gly His Phe Ser Pro Met Ser Pro Asp Phe Thr Val Phe
                485                 490                 495

Met Ile Lys Tyr Leu Met Thr Met Ile Val Gly Ile Thr Thr Gly Phe
                500                 505                 510

Trp Ile Trp Ser Gly Lys Thr Leu Gln Ser Trp Arg Arg Phe Tyr His
            515                 520                 525

Arg Leu Ser His Ser Ser Lys Gly Glu Thr Ala Val
530                 535                 540
```

FZD7 SPECIFIC ANTIBODIES AND VACCINES TO TREAT CANCER AND CONTROL STEM CELL FUNCTION

CROSS-REFERENCE TO RELATED APPLICATIONS

This application is a 371 U.S. National Phase application of International Application No. PCT/US2016/037919 filed Jun. 16, 2016, which in turn claims the benefit of U.S. Provisional Application Ser. No. 62/180,359, filed Jun. 16, 2015, each of which are hereby incorporated by reference in their entirety.

SEQUENCE DISCLOSURE

This application includes, as part of its disclosure, an electronic biological sequence listing text file having the name "41112o2202.txt" which has the size 54,099 bytes and which was created on Dec. 14, 2017, which is hereby incorporated by reference in its entirety.

FIELD OF THE INVENTION

The present application generally relates to antibodies and antibody fragments that specifically bind to human frizzled receptor(s) ("FZD"), e.g., FZD7, and block or inhibit Wnt signaling, as well as compositions containing these anti-FZD7 antibodies and anti-FZD7 antibody fragments. Preferably, such anti-FZD7 antibodies or antibody fragments antagonize, inhibit, neutralize or block at least one biological effect associated with human FZD7, as discussed infra. Moreover, such anti-FZD7 antibodies and antibody fragments preferably will not substantially interact with (bind to) other FZD family members. In addition, the invention relates to nucleic acids encoding said anti-FZD7 antibodies and anti-FZD7 antibody fragments. Further, the invention pertains to the use of said nucleic acids to express said anti-FZD7 antibodies and antibody fragments in desired host cells. Also, the invention pertains to anti-idiotypic antibodies produced against any of the disclosed anti-FZD7 antibodies and antibody fragments.

The invention further relates to therapeutic and diagnostic uses of anti-FZD7 antibodies and anti-FZD7 antibody fragments, preferably anti-FZD7 antibodies and anti-FZD7 antibody fragments that do not substantially interact with (bind to) other FZD family members, in the treatment or prophylaxis of diseases, such as cancer.

The invention also encompasses the use of anti-FZD7 antibodies and anti-FZD7 antibody fragments, preferably anti-FZD7 antibodies and anti-FZD7 antibody fragments that do not substantially interact with (bind to) other FZD family members, for tissue engineering.

Still further the present invention pertains to novel peptides, compositions containing and their use in vaccines.

BACKGROUND

WNT genes encode secreted lipid modified growth factors (Takada et al., 2006; Willert et al., 2003) that exert potent effects on stem cells (Nusse, 2008; Reya and Clevers, 2005; Reya et al., 2003; Willert et al., 2003). Binding of WNT proteins to their cognate receptors encoded by the Frizzled (FZD) gene family initiates various intracellular signaling cascades, most prominently the WNT/β-catenin pathway (also known as "canonical" WNT signaling). β-catenin is a key mediator of WNT signaling by acting as transcription factor to activate expression of WNT target genes. This WNT signaling pathway is a major regulator of many developmental processes, including axis specification, tissue patterning and organogenesis, and its deregulation during embryogenesis often has catastrophic consequences for the developing organism. In the adult, WNT signaling is critical for homeostasis of multiple tissues, including blood, intestine, skin and liver to name a few (reviewed in (Nusse, 2008). Inappropriate activation of WNT signaling has been observed in multiple cancers. A comprehensive analysis of human colorectal cancers found that over 90% of cancers harbor mutations in genes associated with WNT signaling (Cancer Genome Atlas, 2012). Deregulated WNT signaling has also been observed in cancers of the skin, liver, brain, breast and ovary.

The WNT signaling pathway was first elucidated in the *Drosophila* developmental mutant wingless (wg) and from the murine proto-oncogene int-1, now Wnt1 (Nusse & Varmus, 1982, Cell 31:99-109; Van Ooyen & Nusse, 1984, Cell 39:233-40; Cabrera et al., 1987, Cell 50:659-63; Rijsewijk et al., 1987, Cell 50:649-57). Wnt genes encode secreted lipid-modified glycoproteins of which 19 have been identified in mammals. These secreted ligands activate a receptor complex consisting of a Frizzled ("FZD") receptor family member and low-density lipoprotein ("LDL") receptor-related protein 5 or 6 ("LPR5/6"). The FZD receptors are seven transmembrane domain proteins with similarities to the G-protein coupled receptor ("GPCR") superfamily and contain a large extracellular N-terminal ligand binding domain with 10 conserved cysteines, known as a cysteine-rich domain ("CRD") or Fri domain. There are ten human FZD receptors: FZD1-10. Different FZD CRDs have different binding affinities for specific WNTs (Wu & Nusse, 2002, J. Biol. Chem. 277:41762-9), and FZD receptors have been grouped into those that activate the canonical β-catenin pathway and those that activate non-canonical pathways, all of which are described below (Miller et al., 1999, Oncogene 18:7860-72). To form the receptor complex that binds the FZD ligands, FZD receptors interact with LRP5/6, single pass transmembrane proteins with four extracellular EGF-like domains separated by six YWTD amino acid repeats (Johnson et al., 2004, J. Bone Mineral Res. 19:1749).

Three WNT signaling pathways have been characterized: (1) the canonical Wnt pathway; (2) the non-canonical planar cell polarity pathway; and (3) the non-canonical WNT/calcium pathway.

The canonical WNT signaling pathway activated upon receptor binding is mediated by the cytoplasmic protein Dishevelled ("DSH") interacting directly with the FZD receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli ("APC") and Axin. These proteins function as critical scaffolds to allow glycogen synthase kinase ("GSK")-3β to bind and phosphorylate β-catenin, marking it for degradation via the ubiquitin/proteasome pathway. Accumulated cytoplasmic β-catenin is then transported into the nucleus where it interacts with the DNA-binding proteins of the Tcf/Lef family to activate transcription.

In addition to the canonical signaling pathway, WNT ligands also activate β-catenin-independent pathways (Veeman et al., 2003, Dev. Cell 5:367-77). Non-canonical WNT signaling has been implicated in numerous processes, including gastrulation movements via a mechanism similar to the *Drosophila* planar cell polarity ("PCP") pathway. Other potential mechanisms of non-canonical WNT signaling include calcium flux, JNK, and both small and heterotrimeric G-proteins. Antagonism is often observed between the canonical and non-canonical pathways, and some evidence indicates that non-canonical signaling can suppress cancer formation (Olson & Gibo, 1998, Exp. Cell Res. 241:134; Topol et al., 2003, J. Cell Biol. 162:899-908).

The canonical WNT signaling pathway also plays a central role in the maintenance of stem cell populations in the small intestine and colon, and the inappropriate activation of this pathway plays a prominent role in colorectal cancers (Reya & Clevers, 2005, Nature 434:843). Stem cells reside in the crypts of the absorptive epithelium of the intestines and slowly divide to produce rapidly proliferating cells that give rise to all the differentiated cell populations that move up out of the crypts to occupy the intestinal villi. The WNT signaling cascade plays a dominant role in controlling cell fates along the crypt-villi axis and is essential for the maintenance of the stem cell population. Disruption of WNT signaling, e.g., genetic loss of Tcf7/2 by homologous recombination (Korinek et al., 1998, Nat. Genet. 19:379) or overexpression of Dickkopf-1 (Dkk1), a potent secreted Wnt antagonist (Pinto et al., 2003, Genes Dev. 17:1709-13; Kuhnert et al., 2004, Proc. Nat'l. Acad. Sci. 101:266-71), results in depletion of intestinal stem cell populations.

All three pathways are activated by the binding of a WNT-protein ligand to a FZD. FZD7 is one of ten identified human WNT receptors.

FZD7 is expressed in the epiblast of the developing mouse embryo (Kemp C R, et al. Expression of Frizzled5, Frizzled7, and Frizzled10 during early mouse development and interactions with canonical Wnt signaling. Dev Dyn. 2007; 236(7):2011-2019) and that the human homolog FZD7 is elevated in undifferentiated human embryonic stem cells ("hESCs") (Melchior K, et al. The WNT receptor FZD7 contributes to self-renewal signaling of human embryonic stem cells. Biol Chem. 2008; 389(7):897-903; and Sperger J M, et al. Gene expression patterns in human embryonic stem cells and human pluripotent germ cell tumors. Proc Natl Acad Sci USA. 2003; 100(23):13350-13355).

Indeed, FZD7 is specifically expressed in human pluripotent stem cells ("hPSCs") (Fernandez et al., 2014, PNAS, 111(4):1409-14). The inventors previously demonstrated that FZD7 is abundantly expressed in hPSCs and, in fact, based on RNA-seq analysis, FZD7 is the most highly expressed FZD gene in hPSCs. Additionally, the inventors discovered that FZD7 expression declines upon differentiation, and knockdown of FZD7 expression using shRNAs disrupts the pluripotent state of hPSCs. Therefore, FZD7 is a stem cell specific WNT receptor. In addition, FZD7, along with FZD1, 5 and 8, is also expressed in mouse crypt epithelial preparations, which harbor intestinal stem cells (Hughes et al., 2011).

FZD7 expression has also been detected in several cancer cell lines and tumors, including breast cancer (Chakrabarti et al., 2014; Simmons et al., 2014; Yang et al., 2011), ovarian cancer (Asad et al., 2014), hepatocellular carcinoma (Merle et al., 2005; Nambotin et al., 2011; Nambotin et al., 2012; Song et al., 2014; Wei et al., 2011), Wilms' tumor (Pode-Shakked et al., 2011), gastric cancers (Kirikoshi et al., 2001) and colon cancer (Ueno et al., 2009; Vincan et al., 2010). Moreover, in view of the central role for FZD7 in stem cells (discovered by the inventors) and its limited expression in adult tissues, FZD7 may represent a unique cancer stem cell marker that can be targeted with minimal adverse side effects.

However, there are currently no methods to block signaling by specific FZD receptors. Several methods exist that block or inhibit WNT signaling, however, none of these methods block signaling through specific FZD receptors. For example, the following methods have been used to block WNT signaling: (1) extracellular proteins that bind WNT proteins, for example, recombinant SFRP and FZD-CRD-Fc fusions have been used to bind WNT and thereby block its ability to bind receptors; (2) extracellular proteins that block WNT/beta-catenin signaling, for example, recombinant proteins, such as Dkk1; (3) antibodies that bind to multiple FZD receptors, for example, Vantictumab (OMP-18R5, OncoMed Pharmaceuticals, Inc.), which is currently in clinical trial for the treatment of pancreatic cancer (ClinicalTrials.gov Identifier: NCT02005315), metastatic breast cancer (NCT01973309), and solid tumors (NCT01957007), binds to the extracellular domain of FZD7 and cross-reacts with 5 other FZD proteins, i.e., FZD1, 2, 5, 7 and 8 (Gurney et al. 2012); and (4) small molecule inhibitors.

However, none of these WNT inhibitors block the action of individual WNT ligands or FZD receptors. Therefore, although capable of blocking WNT-FZD7 signaling, these compounds interfere with other WNT signaling pathways as well, which may be essential for tissue and organ homeostasis. Given the large number of WNTs (19 human genes) and multiple FZD receptors (10 human genes), it is critical to disrupt signaling by specific WNT-FZD interactions without interfering with other WNT signaling pathways, which may be essential for tissue and organ homeostasis.

The present invention addresses the need for inhibitors that are specific to an individual WNT signaling pathway and provides novel antibodies and antibody fragments, e.g., Fabs, that specifically bind to human FZD7 without substantially interacting with (binding to) other FZD family members.

BRIEF SUMMARY OF THE INVENTION

The invention generally relates to anti-human FZD7 antibodies or antibody fragments that specifically bind to human FZD7, but which do not appreciably bind to other human FZD polypeptides and methods for the production and use thereof in therapy, especially treatment or prevention of cancer, wherein said human FZD7 antibodies or antibody fragments optionally comprise SEQ ID NO: 1, SEQ ID NO: 2, SEQ ID NO: 43, SEQ ID NO: 44, or a variant thereof.

In particular, in exemplary embodiments, such anti-human FZD7 antibodies or antibody fragments will not appreciably bind to any of FZD1, FZD2, FZD3, FZD4, FZD5, FZD6, FZD8, FZD9 and FZD10.

In other exemplary embodiments, such anti-human FZD7 antibody or antibody fragment will be a human, humanized or chimeric antibody (or antigen-binding fragments thereof).

In another exemplary embodiment, such anti-human FZD7 antibodies or antibody fragments will have a binding affinity for FZD7 that is at least 10, 100 or 1000-fold greater than its binding affinity to any other human FZD polypeptide.

In another exemplary embodiment, such anti-human FZD7 antibodies or antibody fragments will not detectably bind to any other human FZD polypeptide.

In another exemplary embodiment, such anti-human FZD7 antibodies or antibody fragments will not comprise (or consist of) FZD7-Fab-1791 or FZD7-Fab-1291.

In another exemplary embodiment, such anti-human FZD7 antibodies or antibody fragments will not contain the identical CDRs as FZD7-Fab-1791 or FZD7-Fab-1291.

More specifically, the invention generally relates to human, humanized or chimeric anti-human FZD7 antibodies or antibody fragments thereof. In one embodiment, the human, humanized or chimeric anti-human FZD7 antibodies or antibody fragments thereof specifically bind to a linear or conformational epitope(s) and/or compete for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291, preferably FZD7-Fab-1791 or chFZD7-1791. The human FZD7 epitope bound by the antibodies or fragments thereof can be identified using mutational analysis, i.e., systematically replacing murine FZD7 amino acid residues with the corresponding human FZD7 amino acid residues and/or making point mutations in the human FZD7 amino acid sequence.

The anti-human FZD7 antibody or antibody fragment thereof may be selected from the group consisting of scFvs, camelbodies, nanobodies, IgNAR, Fab fragments, Fab' fragments, MetMab like antibodies, monovalent antibody fragments, and F(ab')$_2$ fragments. Additionally, the anti-human FZD7 antibody or antibody fragment may comprise a human constant domain, e.g., an IgG1, IgG2, IgG3 or IgG4 isotype. Preferably, the anti-human FZD7 antibody or antibody fragment thereof is a humanized antibody or antibody fragment.

The anti-human FZD7 antibody or antibody fragment may be directly or indirectly attached to a detectable label or therapeutic agent. In one embodiment, the anti-human FZD7 antibody or antibody fragment is attached to at least one effector moiety, which optionally comprises a chemical linker and a cytotoxic agent or payload. In another embodiment, the anti-human FZD7 antibody or antibody fragment thereof is attached to one or more detectable moieties, e.g., comprising a fluorescent dye, enzyme, substrate, bioluminescent material, radioactive material, chemiluminescent moiety, or mixtures thereof. In yet another embodiment, the anti-human FZD7 antibody or fragment thereof is attached to a detectable moiety.

The human, humanized or chimeric anti-human FZD7 antibodies or antibody fragments thereof, when administered to a human subject, may inhibit or neutralize at least one biological effect elicited by FZD7, e.g., FZD7 signaling via Wnt3a and/or FZD7-mediated cell migration and/or FZD7-mediated stem cell replication, self-renewal, and proliferation.

Preferably, the anti-human FZD7 antibodies or antibody fragments does not substantially interact with (bind to) other FZD family members. In one embodiment, the anti-human FZD7 antibody or antibody fragment has higher affinity for FZD7 as compared to other FZD family members (FZD1, FZD2, FZD3, FZD4, FZD5, FZD6, FZD8, FZD9 and FZD10) and/or does not bind to other FZD family members (FZD1, FZD2, FZD3, FZD4, FZD5, FZD6, FZD8, FZD9 and FZD10).

In one embodiment, the human, humanized or chimeric anti-human FZD7 antibody or antibody fragment contains at least 2, at least 3, at least 4, at least 5 or all 6 complementarity determining regions (CDRs) of an anti-human FZD7 antibody selected from chFZD7-1791 or chFZD7-1291.

In another embodiment, the human, humanized or chimeric anti-human FZD7 antibody or antibody fragment comprises: (a) a variable light chain comprising a CDR1 sequence consisting of SEQ ID NO:6; a CDR2 sequence consisting of SEQ ID NO:7; and a CDR3 sequence consisting of SEQ ID NO:8; and/or (b) a variable heavy chain comprising a CDR1 sequence consisting of SEQ ID NO:9; a CDR2 sequence consisting of SEQ ID NO:10; and a CDR3 sequence consisting of SEQ ID NO:11. Alternatively, the anti-human FZD7 antibody or antibody fragment may comprise: (a) a light chain comprising an amino acid sequence with at least 80, 85, 90, 95, 96, 97, 98, or 99% sequence identity to SEQ ID NO: 4 and/or (b) a heavy chain comprising an amino acid sequence with at least 80, 85, 90, 95, 96, 97, 98, or 99% sequence identity to SEQ ID NO:5. Preferably, the anti-human FZD7 antibody or antibody fragment comprises: (a) a light chain having the amino acid sequence of SEQ ID NO:4, and/or (b) a heavy chain having the amino acid sequence of SEQ ID NO:5.

In another embodiment, the human, humanized or chimeric anti-human FZD7 antibody or antibody fragment comprises: (a) a variable light chain comprising a CDR1 sequence consisting of SEQ ID NO:14; a CDR2 sequence consisting of SEQ ID NO:15; and a CDR3 sequence consisting of SEQ ID NO:16; and/or (b) a variable heavy chain comprising a CDR1 sequence consisting of SEQ ID NO:17; a CDR2 sequence consisting of SEQ ID NO:18; and a CDR3 sequence consisting of SEQ ID NO:19. Alternatively, the anti-human FZD7 antibody or antibody fragment may comprise: (a) a light chain comprising an amino acid sequence with at least 80, 85, 90, 95, 96, 97, 98, or 99% sequence identity to SEQ ID NO: 12 and/or (b) a heavy chain comprising an amino acid sequence with at least 80, 85, 90, 95, 96, 97, 98, or 99% sequence identity to SEQ ID NO:13. Preferably, the anti-human FZD7 antibody or antibody fragment comprises: (a) a light chain having the amino acid sequence of SEQ ID NO:12, and/or (b) a heavy chain having the amino acid sequence of SEQ ID NO:13.

In a further embodiment, the human, humanized or chimeric anti-human FZD7 antibody or antibody fragment comprises: a light chain comprising an amino acid sequence with at least 80, 85, 90, 95, 96, 97, 98, or 99% sequence identity to SEQ ID NO: 20 and/or (b) a heavy chain comprising an amino acid sequence with at least 80, 85, 90, 95, 96, 97, 98, or 99% sequence identity to SEQ ID NO:21. Preferably, the anti-human FZD7 antibody or antibody fragment comprises: (a) a light chain having the amino acid sequence of SEQ ID NO:20, and/or (b) a heavy chain having the amino acid sequence of SEQ ID NO:21.

In yet another embodiment, the human, humanized or chimeric anti-human FZD7 antibody or antibody fragment comprises: (a) a light chain comprising an amino acid sequence with at least 80, 85, 90, 95, 96, 97, 98, or 99% sequence identity to SEQ ID NO: 22 and/or (b) a heavy chain comprising an amino acid sequence with at least 80, 85, 90, 95, 96, 97, 98, or 99% sequence identity to SEQ ID NO:23. Preferably, the anti-human FZD7 antibody or antibody fragment comprises: (a) a light chain having the amino acid sequence of SEQ ID NO:22, and/or (b) a heavy chain having the amino acid sequence of SEQ ID NO:23.

The invention also provides an anti-idiotypic antibody produced against an anti-human FZD7 antibody or antibody fragment, e.g., a human, humanized or chimeric anti-human FZD7 antibodies or antibody fragments thereof specifically bind to a linear or conformational epitope(s) and/or compete for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291, preferably FZD7-Fab-1791 or chFZD7-1791. Also encompassed by the disclosure is a method of using the anti-idiotypic antibody or another antibody that specifically binds said anti-human FZD7 antibody to monitor the in vivo levels of said anti-FZD7 antibody or antibody fragment in a subject or to neutralize said anti-FZD7 antibody in a subject being administered said anti-FZD7 antibody or antibody fragment.

The invention further provides a composition suitable for therapeutic, prophylactic, or a diagnostic use comprising a therapeutically, prophylactically or diagnostically effective amount of at least one anti-human FZD7 antibody or antibody fragment or anti-idiotypic antibody. The composition may be suitable for subcutaneous administration or intravenous administration and, optionally, may further comprise a pharmaceutically acceptable diluent, carrier, solubilizer, emulsifier, preservative, or mixture thereof. The composition may be lyophilized, stabilized and/or formulated for administration by injection.

The composition may further comprise another active agent, e.g., an immune modulator, an anti-metastatic, a chemotherapeutic, a hormone or growth factor antagonist, an alkylating agent, a TLR agonist or a cytokine or cytokine antagonist. Preferably, the other agent is selected from the group consisting of alkylating agents (including, without limitation, nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revirnmune™); ifosfamide (Mitoxana®); melphalan (Alkeran®); Chlorambucil (Leukeran®); pipobroman (Amedel®, Vercyte®); tricthylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., TN-alpha (Alferon®, Roferon-A®, Intron®-A) or IFN-gamma (Actimmune®)); interleukins: IL-1, IL-2 (Prolcukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis[(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar®) and its derivatives (e.g., as disclosed generically and specifically in U.S. Pat. No. 5,260,291) and Mitozolomide; insulin tyrosine kinase inhibitors which include without limitation hydroxyl-2-naphthalenyl-methylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9Cl), Bisindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase II elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Also encompassed by the disclosure are isolated nucleic acid sequences encoding the anti-human FZD7 antibodies or antibody fragments or anti-idiotypic antibodies provided, vectors containing the isolated nucleic acid sequence(s), and host cells comprising the isolated nucleic acid sequence(s). The host cell may be a mammalian, bacterial, fungal, yeast, avian or insect cell. Methods of expressing an anti-human FZD7 antibody or antibody fragment comprising culturing the host cell under conditions that provide for expression of said antibody or antibody fragment are also provided.

Other embodiments encompassed by the disclosure include an isolated T cell and/or an isolated NK cell expressing a chimeric antigen receptor (CAR) comprising the anti-human FZD7 antibody or antibody fragment, e.g., ScFv, as well as a transgenic mouse, a cell or tissue isolated therefrom expressing a humanized Fzd7 gene comprising SEQ ID NO: 2 with a P188L mutation.

The invention further relates to the therapeutic and diagnostic uses of anti-human FZD7 antibodies and fragments thereof. In one embodiment, the invention provides a method of blocking, inhibiting or neutralizing FZD7 signaling and/or treating or preventing a condition associated with aberrant FZD7 expression in a subject comprising administering to a subject in need an effective amount of an anti-human FZD7 antibody or antibody fragment that specifically binds to FZD7 but which does not appreciably bind to other human FZD polypeptides, e.g., does not appreciably bind to any of FZD1, FZD2, FZD3, FZD4, FZD5, FZD6, FZD8, FZD9 and FZD10. In one aspect, the antibody employed in the method is not FZD7-Fab-1791 or FZD7-Fab-1291 and/or does not contain the identical CDRs as FZD7-Fab-1791 or FZD7-Fab-1291. The antibody or antibody fragment may have a binding affinity for FZD7 which is at least 10, 100 or 1000-fold greater than its binding affinity to other human FZD polypeptides. The subject treated according to the method may have or previously have had a cancer condition. The treatment may inhibit one or more of tumor invasion, metastasis, tumor growth or cancer re-occurrence.

In an exemplary embodiment, the invention provides a method of blocking, inhibiting or neutralizing FZD7 signaling (e.g., via Wnt3a) comprising administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291.

The invention further provides a method for treating or preventing a condition associated with aberrant FZD7 expression in a subject comprising administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291. In one aspect, the condition is cancer, preferably, a solid tumor, more preferably, a cancer is selected from ovarian cancer, breast cancer, renal cancer or glioblastoma.

The invention also provides a method for blocking, inhibiting or neutralizing FZD7-mediated cell migration and/or FZD7-mediated stem cell replication, self-renewal, and proliferation in a subject comprising administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291.

Moreover, the invention encompasses a method for generating a specific cell population from human pluripotent stem cells, comprising applying an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291 to human pluripotent stem cells; and isolating specific cell populations of interest.

In these methods, the human, humanized or chimeric anti-human FZD7 antibody or antibody fragment preferably does not substantially interact with (bind to) other FZD family members (FZD1, FZD2, FZD3, FZD4, FZD5, FZD6, FZD8, FZD9 and FZD10).

In exemplary embodiment, the anti-human FZD7 antibody or antibody fragment specifically binds to the same linear or conformational epitope(s) and/or competes for binding to the same linear or conformational epitope(s) on human FZD7 as FZD7-Fab-1791 or chFZD7-1791; specifically binds to the same linear or conformational epitope(s) on human FZD7 as an anti-human FZD7 antibody selected from the group consisting of FZD7-Fab-1791, FZD7-Fab-1291, chFZD7-1791, and chFZD7-1291; and/or specifically binds to the same linear or conformational epitope(s) on human FZD7 as FZD7-Fab-1791 or chFZD7-1791. The FZD7 epitope may be identified using mutational analysis.

In one embodiment, the human, humanized or chimeric anti-human FZD7 antibody or antibody fragment contains at least 2, at least 3, at least 4, at least 5 or all 6 complementarity determining regions (CDRs) of an anti-human FZD7 antibody selected from chFZD7-1791 or chFZD7-1291.

In a specific exemplary embodiment, the human, humanized or chimeric anti-human FZD7 antibody or antibody fragment comprises: (a) a variable light chain comprising a CDR1 sequence consisting of SEQ ID NO:6; a CDR2 sequence consisting of SEQ ID NO:7; and a CDR3 sequence consisting of SEQ ID NO:8; and/or (b) a variable heavy chain comprising a CDR1 sequence consisting of SEQ ID NO:9; a CDR2 sequence consisting of SEQ ID NO:10; and a CDR3 sequence consisting of SEQ ID NO:11. In another specific exemplary embodiment, the anti-human FZD7 antibody or antibody fragment comprises: (a) a light chain comprising an amino acid sequence with at least 80, 85, 90, 95, 96, 97, 98, or 99% sequence identity to SEQ ID NO: 4 and/or (b) a heavy chain comprising an amino acid sequence with at least 80, 85, 90, 95, 96, 97, 98, or 99% sequence identity to SEQ ID NO:5. Preferably, the anti-human FZD7 antibody or antibody fragment comprises: (a) a light chain having the amino acid sequence of SEQ ID NO:4, and/or (b) a heavy chain having the amino acid sequence of SEQ ID NO:5.

In a specific exemplary embodiment, the human, humanized or chimeric anti-human FZD7 antibody or antibody fragment comprises: (a) a variable light chain comprising a CDR1 sequence consisting of SEQ ID NO:14; a CDR2 sequence consisting of SEQ ID NO:15; and a CDR3 sequence consisting of SEQ ID NO:16; and/or (b) a variable heavy chain comprising a CDR1 sequence consisting of SEQ ID NO:17; a CDR2 sequence consisting of SEQ ID NO:18; and a CDR3 sequence consisting of SEQ ID NO:19. In another specific exemplary embodiment, the anti-human FZD7 antibody or antibody fragment comprises: (a) a light chain comprising an amino acid sequence with at least 80, 85, 90, 95, 96, 97, 98, or 99% sequence identity to SEQ ID NO: 12 and/or (b) a heavy chain comprising an amino acid sequence with at least 80, 85, 90, 95, 96, 97, 98, or 99% sequence identity to SEQ ID NO:13. Preferably, the anti-human FZD7 antibody or antibody fragment comprises: (a) a light chain having the amino acid sequence of SEQ ID NO:12, and/or (b) a heavy chain having the amino acid sequence of SEQ ID NO:13.

In a specific exemplary embodiment, the human, humanized or chimeric anti-human FZD7 antibody or antibody fragment comprises: (a) a light chain comprising an amino acid sequence with at least 80, 85, 90, 95, 96, 97, 98, or 99% sequence identity to SEQ ID NO: 20 and/or (b) a heavy chain comprising an amino acid sequence with at least 80, 85, 90, 95, 96, 97, 98, or 99% sequence identity to SEQ ID NO:21. Preferably, the anti-human FZD7 antibody or antibody fragment comprises: (a) a light chain having the amino acid sequence of SEQ ID NO:20, and/or (b) a heavy chain having the amino acid sequence of SEQ ID NO:21.

In a specific exemplary embodiment, the human, humanized or chimeric anti-human FZD7 antibody or antibody fragment comprises: (a) a light chain comprising an amino acid sequence with at least 80, 85, 90, 95, 96, 97, 98, or 99% sequence identity to SEQ ID NO: 22 and/or (b) a heavy chain comprising an amino acid sequence with at least 80, 85, 90, 95, 96, 97, 98, or 99% sequence identity to SEQ ID NO:23. Preferably, the anti-human FZD7 antibody or antibody fragment comprises: (a) a light chain having the amino acid sequence of SEQ ID NO:22, and/or (b) a heavy chain having the amino acid sequence of SEQ ID NO:23.

In these methods, the anti-human FZD7 antibody or antibody fragment may be selected from the group consisting of scFvs, camelbodies, nanobodies, IgNAR, Fab fragments, Fab' fragments, MetMab like antibodies, monovalent antibody fragments, and F(ab')$_2$ fragments.

In other embodiments, the antibody or antibody fragment used in these methods comprises a human constant domain, e.g., an IgG1, IgG2, IgG3, or IgG4 antibody. Preferably, the antibody or antibody fragment is a humanized antibody or antibody fragment. The antibody may also be an anti-idiotypic antibody produced against an anti-human FZD7 antibody or antibody fragment.

In yet further embodiments, in these methods, the antibody or antibody fragment may be directly or indirectly attached to a detectable label (e.g., a fluorescent dye, enzyme, substrate, bioluminescent material, radioactive material, chemiluminescent moiety, or mixtures thereof) or therapeutic agent, at least one effector moiety (which optionally comprises a chemical linker), or one or more functional moieties.

In one embodiment, the therapeutic methods further comprise administering separately or co-administering another agent, e.g., comprise another active agent, e.g., an immune modulator, an anti-metastatic, a chemotherapeutic, a hormone or growth factor antagonist, an alkylating agent, a TLR agonist or a cytokine or cytokine antagonist. Preferably, the other agent is selected from the group consisting of alkylating agents (including, without limitation, nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafururacil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-2 (Proleukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis [(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9Cl), Bis-indolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase II elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™). The anti-human FZD7 antibody or antibody fragment and the at least one other agent may be administered concurrently or, alternatively, the anti-human FZD7 antibody or antibody fragment may be administered before or after the at least one other agent.

Another aspect of the invention generally relates to a polyclonal or monoclonal anti-human FZD7 antibody or antibody fragment which may bind to an epitope of human FZD7 including the leucine residue at position 188. Yet another embodiment of the invention encompasses a polyclonal or monoclonal anti-human FZD7 antibody or antibody fragment which may not bind to a human FZD7 polypeptide containing a mutation that consists of the substitution of the leucine residue at position 188 with a proline residue. Another aspect of the invention generally pertains to a polyclonal or monoclonal anti-human FZD7 antibody or antibody fragment which may bind to an epitope of mouse Fzd7 containing a mutation that consists of the substitution of the proline at position 188 with a leucine residue. Another embodiment of the invention generally relates to a polyclonal or monoclonal anti-human FZD7 antibody or antibody fragment which may block single cell spheroid formation of cancer cells, e.g., glioblastoma cells or a glioblastoma cell line.

Another aspect of the invention generally relates to a human cell that may be engineered to express at least one antibody or antibody fragment, e.g., wherein said human cell may comprise an immune cell, e.g., a B cell, T cell, macrophage, dendritic cell, leukocyte, lymphocyte, or an NK cell.

Yet another embodiment of the invention generally relates to a composition suitable for therapeutic, prophylactic, or a diagnostic use that may comprise a therapeutically, prophylactically or diagnostically effective amount of at least one anti-human FZD7 antibody or antibody fragment or anti-idiotypic antibody or a human cell, e.g., a CAR-T cell. Said composition may further comprise a pharmaceutically acceptable diluent, carrier, solubilizer, emulsifier, preservative, immune adjuvant or mixture thereof. Another aspect of the invention generally pertains to a composition which may further include an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, or TIM-3.

Another embodiment of the invention generally pertains to a method of using a transgenic mouse, a cell or tissue isolated therefrom that may express a humanized Fzd7 gene comprising SEQ ID NO: 2 with a P188L mutation or SEQ ID NO: 44 with a P188L mutation to assess the safety and/or efficacy of anti-FZD7 antibodies or antibody fragments. Also, yet another embodiment of the invention generally relates to a method of blocking, inhibiting or neutralizing FZD7 signaling and/or treating or preventing a condition associated with aberrant FZD7 expression in a subject that may comprise administering to a subject in need an effective amount of an anti-human FZD7 antibody or antibody fragment that specifically binds to human FZD7 but which does not appreciably bind to other human FZD polypeptides or a human cell engineered to express said antibody or antibody fragment such as a T cell or NK cell. Also, said method may inhibit or block migration of, or the aggregation or single cell spheroid aggregation of cancer cells, e.g., glioblastoma, ovarian cancer, breast cancer, lung cancer, sarcoma, melanoma, lymphoma, or renal cancer cells. Another embodiment of the invention generally relates to a method of blocking, inhibiting or neutralizing FZD7 signaling that may comprise administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291 or a human cell engineered to express said antibody or antibody fragment such as a T cell or NK cell. Said method may inhibit or block migration of, or the aggregation or single cell spheroid aggregation of cancer cells, e.g., glioblastoma, ovarian cancer, breast cancer, lung cancer, sarcoma, melanoma, lymphoma, or renal cancer cells.

Yet another aspect of the invention generally pertains to a method for treating or preventing a condition associated with aberrant FZD7 expression in a subject that may comprise administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291 or a human cell engineered to express said antibody or antibody fragment such as a T cell or NK cell. Said method may inhibit or block migration of, or the aggregation or single cell spheroid aggregation of cancer cells, e.g., glioblastoma, ovarian cancer, breast cancer, lung cancer, sarcoma, melanoma, lymphoma, or renal cancer cells. Another aspect of the invention generally relates to a method for blocking, inhibiting or neutralizing FZD7-mediated cell migration in a subject that may comprise administering to a subject in need an effective amount of a human, humanized or chimeric anti-human FZD7 antibody or antibody fragment that specifically binds to a linear or conformational epitope(s) and/or competes for binding to the same linear or conformational epitope(s) on human FZD7 as an anti-human FZD7 antibody selected from the group consisting of FZD7-Fab-1791, FZD7-Fab-1291, chFZD7-1791, and chFZD7-1291 or a human cell engineered to express said antibody or antibody fragment such as a T cell or NK cell.

Another aspect of the invention generally relates to any of the methods disclosed herein wherein any of said methods may include the administration of an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3. Another aspect of the invention generally relates to a peptide that may comprise or may consist of the following peptide or a multimer thereof: GSGGPGGGPTAYPTAPY-LPDLPFTALPPGASDGRGRPAFPF (SEQ ID NO: 35). Another aspect of the invention generally relates to a peptide that may comprise or may consist of a fragment of the following peptide or a multimer thereof: GSGG-PGGGPTAYPTAPYLPDLPFTALPPGASDGRGRPAFPF (SEQ ID NO: 35), with the proviso that said fragment comprises the leucine contained in SEQ ID NO: 35 corresponding to the leucine at position 188 of human FZD7, and wherein said peptide specifically binds to FZD7-Fab1791 or FZD7-Fab1291 or an antibody containing the identical CDRs as FZD7-Fab-1791 or FZD7-Fab-1291. Said peptide may comprise at least 3 residues including the leucine contained in SEQ ID NO: 35 which corresponds to the leucine at position 188 of human FZD7. Also, said peptide may comprise at least 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, or 40 residues of the peptide of SEQ ID NO: 35 including the leucine contained in SEQ ID NO: 35 which corresponds to the leucine at position 188 of human FZD7. Another aspect of the invention generally relates to a peptide as discussed herein which may attached to a polypeptide or another moiety which is not an amino terminal or carboxy terminal fragment of human FZD7, and/or which may be attached to an immunogen or to a detectable label or to a moiety which improves in vivo half-life or in vivo stability, e.g., wherein the label may be GST, GFP or FLAG.

Another aspect of the invention generally pertains to a recombinant cell that may express a peptide as discussed herein, e.g., a human immune cell such as a T or NK cell. Another aspect of the invention generally relates to a polyclonal or monoclonal antibody that specifically binds to the peptide or cell as discussed herein. Another aspect of the invention generally relates to a method of producing antibodies specific to human FZD7 that may comprise immunizing a host or immune cells (in vitro immunization) with at least one peptide as discussed herein. Another aspect of the invention generally relates to a therapeutic or prophylactic cancer vaccine that may contain at least one peptide or cell as discussed herein and at least one pharmaceutically acceptable carrier. Said vaccine may comprise at least one adjuvant, and further wherein said adjuvant may comprise one or more of ALUM, saponin, squalene, a dsRNA, a ssDNA, an unmethylated CPG, a TLR agonist, and a cytokine. Another aspect of the invention generally pertains to a vaccine as discussed herein which may further include an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, or TIM-3.

Yet another aspect of the invention generally relates to a method of eliciting protective or therapeutic anti-cancer immunity that may comprise administering a prophylactically or therapeutically effective amount of a peptide, cell or vaccine as discussed herein, e.g., wherein said cancer may be selected from ovarian cancer, breast cancer, lung cancer, sarcoma, melanoma, lymphoma, renal cancer or glioblastoma. Said method may further include an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, or TIM-3.

BRIEF DESCRIPTION OF THE SEVERAL VIEWS OF THE DRAWING

FIG. 1 provides (i) amino acid sequences corresponding to the light chain region (SEQ ID NO:4) and the heavy chain region (SEQ ID NO:5) of FZD7-Fab-1791, (ii) and amino acid sequences corresponding to the light chain region (SEQ ID NO:12) and the heavy chain region of FZD7-Fab-1291 (SEQ ID NO:13). The light chain CDRs (SEQ ID NOs: 6-8 and SEQ ID NOs:14-16) and heavy chain CDRs (SEQ ID NOs:9-11 and SEQ ID NOs:17-19) are designated in bold.

FIG. 2 provides (i) amino acid sequences corresponding to the light chain region (SEQ ID NO:20) and the heavy chain region (SEQ ID NO:21) of a chimeric antibody, chFZD7-1791, (ii) and amino acid sequences corresponding to the light chain region (SEQ ID NO:22) and the heavy chain region (SEQ ID NO:23) of a chimeric antibody, chFZD7-1291. The light chain and heavy chain CDRs are designated in bold.

FIG. 3 provides an alignment of the partial human FZD7 amino acid sequence (SEQ ID NO: 1) and the partial mouse FZD7 amino acid sequence (SEQ ID NO: 2) as well as a consensus sequence ("majority") (SEQ ID NO: 3). The amino acid residues that differ between the human FZD7 amino acid sequence and the mouse FZD7 amino acid sequence are highlighted and designated as "X" in the consensus sequence.

FIG. 4A: FZD7-Fab-1791 reacts with human FZD7, but not with mouse FZD7 (right panel), whereas a control antibody reacts with both human and mouse FZD7 (left panel). FIG. 4B Schematic of the predicted FZD7 protein topology showing the region of greatest divergence between the mouse and human FZD7 amino acid sequences (green rectangle) and the C-terminal V5 tag (orange rectangle). Mutational analysis of FZD7, in which mouse FZD7 amino acid residues were substituted with the corresponding human FZD7 amino acid residues (SEQ ID NOs:24-34), identified the FZD7-Fabs' epitope (see FIG. 4C and FIG. 4D, in which + indicates FZD7 reactivity with the Fab, whereas—indicates a lack of reactivity between FZD7 and the Fab).

FIGS. 6A and 6B show FZD7 signaling in cancel cell lines. FIG. 6A: The breast cancer cell line, MDA-MB-231, was stably transduced with the Wnt reporter, TOP-Flash. Cells were treated with an increasing dose of Wnt3a (0-5 nM) in the presence of absence of FZD7-Fab-1791. The addition of FZD7-Fab-1791 (200 nM) reduced reporter activity in the cells by about 3-fold. FIG. 6B: OVCAR4 cells were treated with Wnt3a, CHIR, FZD7-Fab-1791, or FZD7-Fab-1291 for 24 hours before cell lysate was prepared and immunoblotted for FZD7 protein. Certain treatments resulted in a decrease in FZD7 protein levels.

FIG. 7A: OVCAR4 cells were analyzed by flow cytometry for surface expression of FZD7 using FZD7-Fab-1791, and sorted into cell populations with high FZD7 expression (FZD7$^{Hi}$) and low FZD7 expression)(FZD7$^{Lo}$. FIG. 7B: FZD7$^{Hi}$ cells are enriched for FZD7 mRNA relative to FZD7$^{Lo}$ cells.

FIG. 8A: FZD7-Fab-1791 blocks migration of a breast cancer cell line. A confluent layer MDA-MB231, a breast cancer cell line, was "wounded", i.e., a pipette tip was used to create a scratch in the confluent layer. After 24 hours, the width of the wound was measured. The amount of wound closure, i.e., cell migration, was significantly less in the presence of FZD7-Fab-1791 as compared to control (no FZD7-Fab-1791). The presence of Wnt3a had no effect on migration. FIG. 8B: FZD7-Fab-1791 blocks migration of an ovarian cancer cell line. OVCAR4 cells were seeded on the upper chamber of a transwell chamber, and FZD7-Fab-1791 (500 nM) was added to both the upper and lower chambers. FZD7-Fab-1791 significantly reduced migration of cells through the membrane as measured by fixing and staining the lower surface.

FIGS. 10A and 10B show detection of FZD7 protein in primary cancer samples using FZD7-Fab-1791. Arrowheads indicate staining consistent with membrane localization, as expected for FZD7. FIG. 10A: Two out of three (66%) ovarian carcinoma samples analyzed by immunohistochemistry using FZD7-Fab-1791 exhibited elevated FZD7 protein levels, compared to normal ovary tissue. FIG. 10B: 21 of 73 (29%) renal cell carcinoma samples analyzed by immunohistochemistry using FZD7-Fab-1791 exhibited elevated FZD7 protein levels, compared to normal kidney tissue.

FIG. 11A: Relative expression of FZD7 (black) and GAPDH (gray) were analyzed in 82 PDX samples. FZD7 expression varied between individual samples. The blue dotted line indicates an expression value of 9. FIG. 11B: Relative expression analysis of FZD7 across different cancer types showed that 50% (n=8) of the breast cancer samples express high levels of FZD7.

FIG. 12 shows the expression of FZD7 in glioblastoma. RNA was isolated from the indicated cell types, labeled on the X axis, and expression of FZD7 and POU5F1 was determined by RT-qPCR. HEK293 and H1 cells served as negative and positive controls, respectively, for FZD7 and POU5F1 expression. NHA=normal human astrocytes.

FIG. 13B shows a bar graph that provides quantitation on the number of colonies per well of a 24-well plate.

FIG. 14A-D shows FZD7 antibody specificity. GST fusions with 42 amino acids of FZD7 surrounding amino acid 188, named GST-L188 (FIG. 14A, SEQ ID NO: 35) and GST-P188 (FIG. 14B, SEQ ID NO: 36) were expressed and immunoblotted either with the FZD7-specific antibody or with a GST-specific antibody. L188 represents the wildtype sequence recognized by the FZD7-specific antibody (FIG. 14C). P188 represents the mutant sequence that is not recognized by the antibody (FIG. 14C). αGST served as a control (FIG. 14D).

DETAILED DESCRIPTION

Figure 4:
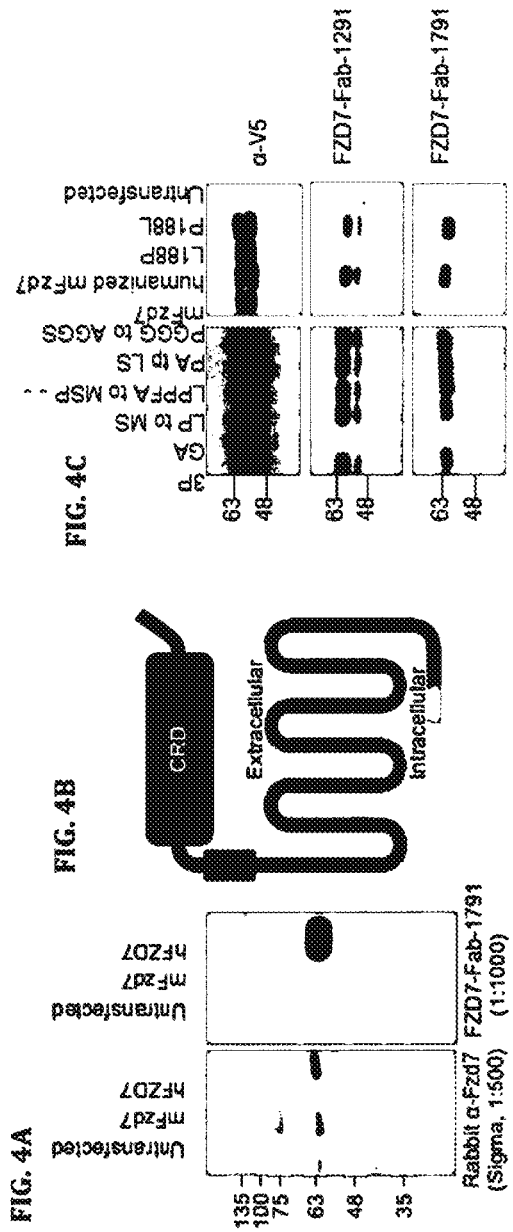
FIG. 4A-D provides epitope mapping data for FZD7-Fab-1791 and FZD7-Fab-1291.

The present invention provides antibodies and antibody fragments, e.g., Fabs that specifically bind to FZD7 and block or inhibit WNT signaling through this particular FZD receptor, as well as compositions containing these anti-FZD7 antibodies and anti-FZD7 antibody fragments. In addition, the invention relates to nucleic acids encoding said anti-FZD7 antibodies and anti-FZD7 antibody fragments and the use of said nucleic acids to express said anti-FZD7 antibodies and antibody fragments in desired host cells, including anti-idiotypic antibodies produced against any of the disclosed anti-FZD7 antibodies and antibody fragments. Additionally, the invention provides methods for using the disclosed anti-FZD7 antibodies and anti-FZD7 antibody fragments which do not substantially interact with (bind to) other FZD family members in the diagnosis, treatment or prophylaxis of diseases, such as cancer, as well as the use of the anti-FZD7 antibodies and antibody fragments for tissue engineering.

Prior to disclosing the invention in detail, the following definitions are provided. Unless defined otherwise, all technical and scientific terms used herein have the same meaning as commonly understood to one of ordinary skill in the art to which this invention belongs.

The term "FZD7" refers to "frizzled class receptor 7", which is a protein encoded by the FZD7 gene. "FZD7" is intended to encompass the human protein (NP_003498) (SEQ ID NO:1) as well as its orthologs, e.g., murine Fzd7 (also known as Fz7) (NP_032083) (SEQ ID NO:2) as well as chimpanzee, cow, rat, etc. encoded by the corresponding gene in the respective species. In a preferred embodiment, "FZD7" refers to human FZD7. "FZD7" includes all precursor, mature, and variant forms thereof. Amino acids 1-32 of FZD7 SEQ ID NO: 1 and SEQ ID NO: 2 represent a signal sequence, and it is to be understood that FZD7 additionally includes any signal sequence that can be used in place of amino acids 1-32.

The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518): 168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragments" or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187

(1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the "footprint" of the specifically antigen binding peptide). The term epitope herein includes both types of amino acid binding sites in any particular region of FZD7 that specifically binds to an anti-FZD7 antibody or anti-FZD7 antibody fragment. FZD7 may comprise a number of different epitopes, which may include, without limitation, (1) linear peptide antigenic determinants, (2) conformational antigenic determinants which consist of one or more non-contiguous amino acids located near each other in a mature FZD7 conformation; and (3) post-translational antigenic determinants which consist, either in whole or part, of molecular structures covalently attached to a FZD7 protein such as carbohydrate groups.

The phrase that an antibody (e.g., first antibody) binds "substantially" or "at least partially" the same epitope as another antibody (e.g., second antibody) means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody.

The phrase "binds to the same or overlapping epitope or determinant as" an antibody of interest means that an antibody "competes" with said antibody of interest for at least one, (e.g., at least 2, at least 3, at least 4, at least 5) or all residues on FZD7 to which said antibody of interest specifically binds. The identification of one or more antibodies that bind(s) to substantially or essentially the same epitope as the monoclonal antibodies described herein can be readily determined using alanine scanning. Additionally, any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

For example, where the test antibodies to be examined are obtained from different source animals, or are even of a different Ig isotype, a simple competition assay may be employed in which the control antibody is mixed with the test antibody and then applied to a sample containing FZD7. Protocols based upon ELISAs, radioimmunoassays, Western blotting, and the use of BIAcore® analysis are suitable for use in such simple competition studies.

In certain embodiments, the control anti-FZD7 antibody is pre-mixed with varying amounts of the test antibody (e.g., in ratios of about 1:1, 1:2, 1:10 or about 1:100) for a period of time prior to applying to the FZD7 antigen sample. In other embodiments, the control and varying amounts of test antibody can simply be added separately and admixed during exposure to the FZD7 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labeling the control antibody with a detectable label) it can be determined if the test antibody reduces the binding of the control antibody to the FZD7, indicating that the test antibody recognizes substantially the same epitope as the control anti-FZD7 antibody. The binding of the (labeled) control antibody in the presence of a completely irrelevant antibody (that does not bind FZD7) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of the control antibody to FZD7 by at least about 50%, such as at least about 60%, or more preferably at least about 70% (e.g., about 65-100%), at any ratio of test antibody between about 1:1 or 1:10 and about 1:100 is considered to be an antibody that binds to substantially the same or overlapping epitope or determinant as the control antibody.

Preferably, such test antibody will reduce the binding of the control antibody to FZD7 antigen preferably at least about 50%, at least about 60%, at least about 80% or at least about 90% (e.g., about 95%) of the binding of the control antibody observed in the absence of the test antibody.

A simple competition assay in which a test antibody is applied at saturating concentration to a surface onto which FZD7 is immobilized also may be advantageously employed. The surface in the simple competition assay is preferably a BIAcore® chip (or other media suitable for surface plasmon resonance analysis). The binding of a control antibody that binds FZD7 to the FZD7-coated surface is measured. This binding to the FZD7-containing surface of the control antibody alone is compared with the binding of the control antibody in the presence of a test antibody. A significant reduction in binding to the FZD7-containing surface by the control antibody in the presence of a test antibody indicates that the test antibody recognizes substantially the same epitope as the control antibody such that the test antibody "competes" with the control antibody. Any test antibody that reduces the binding of control antibody by at least about 20% or more, at least about 40%, at least about 50%, at least about 70%, or more, can be considered to be an antibody that binds to substantially the same epitope or determinant as the control antibody. Preferably, such test antibody will reduce the binding of the control antibody to FZD7 by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Alternatively, the antibody having greater affinity for FZD7 antigen is bound to the FZD7-containing surface first, as it will be expected that the decrease in binding seen for the second antibody (assuming the antibodies are competing) will be of greater magnitude. Further examples of such assays are provided in e.g., Saunal and Regenmortel, *J. Immunol. Methods* 183: 33-41 (1995), the disclosure of which is incorporated herein by reference.

In addition, whether an antibody binds the same or overlapping epitope(s) on FZD7 as another antibody or the epitope bound by a test antibody may in particular be determined using a western-blot based assay. In this assay a library of peptides corresponding to the antigen bound by the antibody, the FZD7 protein, is made, that comprise overlapping portions of the protein, typically 10-25, 10-20 or 10-15 amino acids long. These different overlapping amino acid peptides encompassing the FZD7 sequence are synthesized and covalently bound to a nitrocellulose membrane. Blots are then prepared and probed according to the manufacturer's recommendations.

Essentially, the immunoblot assay then detects by fluorometric means what peptides in the library bind to the test antibody and thereby can identify what residues on the antigen, i.e., FZD7, interact with the test antibody. (See U.S. Pat. No. 7,935,340, incorporated by reference herein).

Various epitope mapping techniques are known in the art. By way of example, X-ray co-crystallography of the antigen and antibody; NMR; surface plasmon resonance (e.g., at 25° or 37° C.); array-based oligo-peptide scanning; site-directed mutagenesis (e.g., alanine scanning); mutagenesis mapping; hydrogen-deuterium exchange; phage display; and limited proteolysis are all epitope mapping techniques that are well known in the art. See, e.g., Epitope Mapping Protocols: Second Edition, Methods in Molecular Biology (Springer Protocols), ed. Mike Schutkowski and Ulrich Reineke and Epitope Mapping Protocols, ed. Glenn Morris (Humana Press), both of which are herein incorporated by referenced in their entirety.

The identification of one or more antibodies that bind(s) to substantially or essentially the same epitope as the monoclonal antibodies described herein, e.g., FZD7-Fab-1791, FZD7-Fab-1271, chFZD7-1791 or chFZD7-1291, can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is incorporated herein by reference). It will be understood that determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (one of FZD7-Fab-1791. FZD7-Fab-1291, chFZD7-1791 or chFZD7-1291, for example) is mixed with the test antibody and then applied to a sample containing FZD7, each of which is known to be bound by FZD7-Fab-1791, FZD7-Fab-1291, chFZD7-1791 or chFZD7-1291. Protocols based upon ELISAs, radioimmunoassays, Western blotting, and BIACORE analysis (as described in the Examples section herein) are suitable for use in such simple competition studies.

In certain embodiments, the method comprises pre-mixing the control antibody with varying amounts of the test antibody (e.g., in ratios of about 1:1, 1:2, 1:10 or about 1:100) for a period of time prior to applying to the FZD7 antigen sample. In other embodiments, the control and varying amounts of test antibody can be added separately and admixed during exposure to the FZD7 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labelling the control antibody with a detectable label), the method can be used to determine that the test antibody reduces the binding of the control antibody to the FZD7 antigen, indicating that the test antibody recognizes substantially the same epitope as the control antibody (e.g., FZD7-Fab-1791, FZD7-Fab-1291, chFZD7-1791 or chFZD7-1291). The binding of the (labeled) control antibody in the presence of a completely irrelevant antibody (that does not bind FZD7) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of FZD7-Fab-1791, FZD7-Fab-1291, chFZD7-1791 or chFZD7-1291 to FZD7 antigens by at least about 50%, such as at least about 60%, or more preferably at least about 70% (e.g., about 65-100%), at any ratio of control FZD7-Fab-1791, FZD7-Fab-1271, chFZD7-1791 or chFZD7-1291:test antibody between about 1:1 or 1:10 and about 1:100 is considered to be an antibody that binds to substantially the same epitope or determinant as FZD7-Fab-1791, FZD7-Fab-1271, chFZD7-1791 or chFZD7-1291, respectively. Preferably, such test antibody will reduce the binding of FZD7-Fab-1791, FZD7-Fab-1271, chFZD7-1791 or chFZD7-1291 to FZD7 antigen at least about 50%, at least about 60%, at least about 80% or at least about 90% (e.g., about 95%) of the binding of FZD7-Fab-1791, FZD7-Fab-1271, chFZD7-1791 or chFZD7-1291 observed in the absence of the test antibody. These methods can be adapted to identify and/or evaluate antibodies that compete with other control antibodies.

A simple competition assay in which a test antibody is applied at saturating concentration to a surface onto which FZD7 is immobilized also may be advantageously employed. The surface in the simple competition assay is preferably of a media suitable for Octet and/or ProteOn. The binding of a control antibody (e.g., FZD7-Fab-1791, FZD7-Fab-1271, chFZD7-1791 or chFZD7-1291) to the FZD7-coated surface is measured. This binding to the FZD7-containing surface of the control antibody alone is compared with the binding of the control antibody in the presence of a test antibody. A significant reduction in binding to the FZD7-containing surface by the control antibody in the presence of a test antibody indicates that the test antibody recognizes substantially the same epitope as the control antibody such that the test antibody "competes" with the control antibody. Any test antibody that reduces the binding of control antibody (such as FZD7-Fab-1791, FZD7-Fab-1271, chFZD7-1791 or chFZD7-1291) to FZD7 by at least about 20% or more, at least about 40%, at least about 50%, at least about 70%, or more, can be considered to be an antibody that binds to substantially the same epitope or determinant as the control antibody (e.g., FZD7-Fab-1791, FZD7-Fab-1271, chFZD7-1791 or chFZD7-1291). Preferably, such test antibody will reduce the binding of the control antibody (e.g., FZD7-Fab-1791, FZD7-Fab-1271, chFZD7-1791 or chFZD7-1291) to the FZD7 antigen by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for FZD7 is bound to the FZD7-containing surface first, as it will be expected that the decrease in binding seen for the second antibody (assuming the antibodies are competing) will be of greater magnitude. Further examples of such assays are provided in, e.g., Saunal and Regenmortel, J. Immunol. Methods 183: 33-41 (1989), the disclosure of which is incorporated herein by reference.

Determination of whether an antibody, antibody fragment, or antibody derivative binds within one of the epitope regions defined above can be carried out in ways known to the person skilled in the art. In another example of such mapping/characterization methods, an epitope region for an anti-FZD7 antibody may be determined by epitope "foot-printing" using chemical modification of the exposed amines/carboxyls in the FZD7 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, *Analytical Biochemistry,* 267(2): 252-259 (1999) and Engen, J. R. and Smith, D. L., *Anal. Chem.* 73, 256A-265A (2001). Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. (44): 149-67 (1989); Huang et al, *Journal of Molecular Biology* 281(1):61-67 (1998); and Saito and Patterson, *Methods* 9(3):516-24 (1996).

Epitope mapping/characterization also can be performed using mass spectrometry methods. See, e.g., Downward, *J Mass Spectrom.* 35(4):493-503 (2000) and Kiselar and Downard, *Anal Chem.* 71(9): 1792-801 (1999).

Protease digestion techniques also can be useful in the context of epitope mapping and identification. Antigenic determinant-relevant regions/sequences can be determined by protease digestion, e.g. by using trypsin in a ratio of about 1:50 to FZD7 overnight (o/n) digestion at 37° C. and pH 7-8, followed by mass spectrometry ("MS") analysis for peptide identification. The peptides protected from trypsin cleavage by the anti-FZD7 antibody can subsequently be identified by comparison of samples subjected to trypsin digestion and samples incubated with antibody and then subjected to digestion by e.g. trypsin (thereby revealing a footprint for the antibody). Other enzymes like chymotrypsin or pepsin can be used in similar epitope characterization methods. Moreover, enzymatic digestion can provide a quick method for analyzing whether a potential antigenic determinant sequence is within a region of FZD7 in the context of a FZD7-binding polypeptide. If the polypeptide is not surface exposed, it is most likely not relevant in terms of immunogenicity/antigenicity. See, e.g., Manca, *Ann 1st Super Sanita.* 27(1):15-9 (1991) for a discussion of similar techniques.

Site-directed mutagenesis is another technique useful for elucidation of a binding epitope. For example, in "alanine-scanning", each residue within a protein segment is replaced with an alanine residue (or another residue such as valine where alanine is present in the wild-type sequence), and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, *Science* 267:383-386 (1995); and Wells, *Proc Natl Acad Sci USA* 93:1-6 (1996). Alternatively, mutational analysis can be performed by substituting residues in the murine FZD7 receptor with corresponding residues from the human FZD7 receptor.

Electron microscopy can also be used for epitope "foot-printing". For example, Wang et al., *Nature* 355:275-278 (1992) used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance ("SPR", BIACORE) and reflectometric interference spectroscopy ("RifS"). See, e.g., Fagerstam et al., *Journal Of Molecular Recognition* 3:208-14 (1990); Nice et al., *J. Chromatogr.* 646:159-168 (1993); Leipert et al., *Angew. Chem. Int. Ed.* 37:3308-3311 (1998); Kroger et al., *Biosensors and Bioelectronics* 17:937-944 (2002).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

Anti-FZD7 Antibodies and Binding Fragments Thereof that Specifically Bind Human FZD7

FZD7 is a member of the 'frizzled' gene family of 7-transmembrane domain proteins that are receptors for WNT signaling proteins. It is one of ten known human FZD receptors. FZD7 expression is significantly elevated in undifferentiated cells relative to differentiated cells.

FZD7 plays an important role in stem cell growth and, moreover, is aberrantly expressed in various human cancers, in particular solid tumors such as, but not limited to, ovarian cancer, breast cancer, renal cancer and glioblastoma.

The present invention provides exemplary antibodies or antibody fragments that bind to FZD7, in particular human FZD7, and do not substantially interact with (bind to) other FZD family members. Other antibodies or antibody fragments that bind to FZD7, including those having different CDRs and epitopic specificity may be obtained using the disclosure of the present specification and that which is generally known in the art. Such antibodies and antibody fragments specifically block or inhibit WNT-FZD7 signaling and, therefore, are useful in treating or preventing diseases or conditions associated with FZD7 overexpression and/or FZD7 signaling, including, for example, cancer. Also, the disclosed FZD7-specific antibodies and antibody fragments are useful for tissue engineering.

In some embodiments, the antibody or antibody fragment according to the invention comprises one or more complementarity determining regions ("CDRs"), a variable light ("$V_L$") chain and/or variable heavy ("$V_H$") chain of the anti-FZD7 antibodies and antibody fragments described herein.

In some embodiments, an anti-FZD7 antibody or antibody fragment according to the invention will interfere with, block, reduce or modulate the interaction between FZD7 and Wnt3a.

In some embodiments, the anti-FZD7 antibody or antibody fragment according to the invention are chimeric, humanized or human antibodies or antigen-binding fragments thereof. Optionally, the antibody is a monoclonal antibody or antigen-binding fragment thereof, chimeric antibody or antigen-binding fragment thereof, humanized antibody or antigen-binding fragment thereof, single-chain antibody or antibody that competitively inhibits the binding of an antibody disclosed herein to its respective antigenic epitope.

In some embodiments, the anti-FZD7 antibody or antibody fragment according to the invention is comprised in an antibody-drug conjugate ("ADC"). For example, the antibodies or antibody fragments, e.g., scFv, may be conjugated to an anti-cancer drug (a payload), e.g., a cell toxin or a cytotoxin, that specifically targets a certain tumor marker. Antibodies of the present invention may optionally be conjugated to a growth inhibitory agent or cytotoxic agent including, for example, a maytansinoid (such as DM1), calicheamicin, dolastatin 10, monomethyl auristatin E, an antibiotic, a radioactive isotope, a nucleolytic enzyme or the like.

The chemical linker used in an ADC should function as a highly stable bridge (as compared to a conditionally stable linker) between the antibody and release drug (i.e., "payload"), e.g., cytotoxin, that allows efficient drug release upon delivery inside malignant cells. Exemplary linkers include cleavable peptides in combination with self-immolative groups that undergo intracellular enzymatic degradation, e.g, hydrazone, peptide, disulfide, thioester, and hydrophilic.

In some embodiments, the anti-FZD7 antibody or antibody fragment according to the invention is comprised in a bispecific antibody.

In some embodiments, the anti-FZD7 antibody or antibody fragment, e.g., scFv, is comprised in a chimeric antigen receptor (CAR) that is then expressed in a T cell and/or an NK cell, e.g., a T cell and/or an NK cell removed from a patient and engineered to express the anti-FZD7 antibody or antibody fragment. The engineered CAR T cells and/or NK cells may have a modular design that includes the FZD7-targeting antibody or antibody fragments herein, and a costimulatory signaling domain, e.g., to amplify the activation of the cells, giving them a stronger signal to multiply and kill cancer cells, and/or other mechanisms to amplify or dampen (in the case of adverse reactions) T cell and/or NK cell activation, e.g., "armored CAR" technology, dual costimulatory domain (e.g., "GoCAR-Ts"). Such engineered CAR T cells can be reintroduced into the patient from whom it was isolated (or other patients) to recognize and kill cancer cells.

As mentioned, the anti-FZD7 antibodies or antibody fragments according to the invention have a variety of uses. For example, the subject antibodies and fragments can be useful in therapeutic applications, e.g., cancer treatment, as well as diagnostic applications, e.g., screening patient samples for FZD7 expression levels.

The subject anti-FZD7 antibodies or antibody fragments may be used alone or in association with other active agents or drugs, i.e., as a monotherapy or in combination therapy, respectively.

The peptide epitope for the FZD7-specific antibodies can be used to make cancer vaccines using methods well known in the art.

Additionally, as discussed above, the subject anti-FZD7 antibodies or antibody fragments can also be used to generate specific cell populations from human pluripotent stem cells, including both human embryonic stem cells ("hESCs") and induced pluripotent stem cells ("hiPSCs").

Exemplary anti-FZD7 antibodies and antibody fragments according to the invention, and the specific CDRs thereof are identified in this section. For convenience, each exemplified antibody or fragment, and corresponding sequences are separately identified by a specific nomenclature, i.e., FZD7-Fab-1791, FZD7-Fab-1291, chFZD7-1791 or chFZD7-1291.

FZD7-Fab-1791

In one embodiment, the invention includes antibodies and antibody fragments having binding specificity to FZD7 that possess a light chain sequence comprising the sequence set forth below:

(SEQ ID NO: 4)
DIVMTQSPKSMSMSVGERVTLRCKASENVLNYVSWYQQKPEQSPKLLIYG

ASNRYTGVPDRFTGSGSATDFTLTISSVQAEDLADYHCGQSYRYPTFGAG

TKLELKRADAAPTVSIFPPSSEQLTSGGASVVCFLNNFYPKDINVKWKID

GSERQNGVLNSWTDQDSKDSTYSMSSTLTL TKDEYERHNSYTCEATHKT

STSPIVKSFNRNESYPYDVPDYAS

In another embodiment, the invention includes antibodies and antibody fragments having binding specificity to FZD7 that possess a heavy chain sequence comprising the sequence set forth below:

(SEQ ID NO: 5)
EVQPVESGGGLVQPKGSLKLSCAASGFTFNTYAMHWVRQAPGKGLEWVAR

IRSKSNNYAKNYDDSVKDRFTISRDDSQSMLYLQMNNLKTEDTAMYYCVR

ENYGGRFDYWGQGTTLTVSSAKTTPPSVYPLAPGSAAQTNSMVTLGCLVK

GYFPEPVTVTWNSGSLSSGVHTFPAVLQSDLYTLSSSVTVPSSTWPSETV

TCNVAHPASSTKVDKKIVPRDSHHHHHH

In yet another embodiment, the invention includes antibodies and antibody fragments having binding specificity to FZD7 that possess the same epitopic specificity as FZD7-Fab-1791, i.e., which contains a light chain sequence of SEQ ID NO:4 and a heavy chain sequence of SEQ ID NO:5.

In another embodiment, the invention includes antibodies and antibody fragments having binding specificity to FZD7 that contain one, two, or three of the polypeptide sequences of SEQ ID NO:6 (KASENVLNYVS); SEQ ID NO:7 (GAS-NRYT); and SEQ ID NO:8 (GQSYRYP), which correspond to CDR1, CDR2 and CDR3, respectively, of the light chain sequence of SEQ ID NO: 4, and/or which further contain one, two, or three of the polypeptide sequences of SEQ ID NO:9 (TYAMH); SEQ ID NO:10 (RIRSKSNNYAKNYDD-SVKD); and SEQ ID NO:11 (ENYGGRFDY), which correspond to CDR1, CDR2 and CDR3, respectively, of the heavy chain sequence of SEQ ID NO:5, or antibodies or fragments containing combinations of sequences which are at least 80%, 85%, 90%, 95%, 96%, 97%, 98% or 99% identical thereto.

In yet another embodiment, the invention includes antibodies and antibody fragments having binding specificity to FZD7 that possess the same epitopic specificity as an antibody comprising one, two, three, four, five or six CDRs of FZD7-Fab-1791, i.e., SEQ ID NOs:6-11.

In another embodiment of the invention, the antibodies of the invention or fragments thereof comprise, or alternatively consist of, combinations of one or more of the exemplified light chain and heavy chain sequences set forth above, or sequences that are at least 90% or 95% identical thereto. Methods for determining homology between amino acid sequences are well known to those of ordinary skill in the art.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

In an additional embodiment, the invention is further directed to polynucleotides encoding antibody polypeptides having binding specificity to FZD7, including the light and/or heavy chains of FZD7-Fab-1791 as well as fragments, variants, combinations of one or more of the FRs, CDRs, the variable heavy chain and variable light chain sequences, and the heavy chain and light chain sequences set forth above, including all of them or sequences which are at least 90% or 95% identical thereto.

FZD7-Fab-1291

In one embodiment, the invention includes antibodies and antibody fragments having binding specificity to FZD7 that possess a light chain sequence comprising the sequence set forth below:

```
                                                    (SEQ ID NO: 12)
DVVMSQSPSSLAVSVGEKVTMSCKSSQSLLYSSNQKNYLAWYQQKPGQSP

KLLIYWASTRESGVPDRFTGSGSGTDFTLTISSVKAKDLAVYYCQQYYSY

PTFGGGTKLEIKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNESYPYDVPDYAS
```

In another embodiment, the invention includes antibodies and antibody fragments having binding specificity to FZD7 that possess a heavy chain sequence comprising the sequence set forth below:

```
                                                    (SEQ ID NO: 13)
EVQLVESGGGLVKPGGSLKLSCAASGFTFSSYAMSWVRQTPEKRLEWVAT

ISDGGSYTRYPDKLKGRFTISRDNAKNNLYLQMSHLKSEDTAMYYCARVG

GRRDYFDYWGQGTTLTVSSAKTTPPSVYPLAPGSAAQTNSMVTLGCLVKG

YFPEPVTVTWNSGSLSSGVHTFPAVLQSDLYTLSSSVTVPSSTWPSETVT

CNVAHPASSTKVDKKIVPRDCHHHHHH
```

In yet another embodiment, the invention includes antibodies and antibody fragments having binding specificity to FZD7 that possess the same epitopic specificity as FZD7-Fab-1291, i.e., which contains a light chain sequence of SEQ ID NO:12 and a heavy chain sequence of SEQ ID NO:13.

In another embodiment, the invention includes antibodies and antibody fragments having binding specificity to FZD7 that contain one, two, or three of the polypeptide sequences of SEQ ID NO:14 (KSSQSLLYSSNQKNYLAW); SEQ ID NO:15 (WASTRES); and SEQ ID NO:16 (QQYYSYP), which correspond to CDR1, CDR2 and CDR3, respectively, of the light chain sequence of SEQ ID NO: 12, and/or which further contain one, two, or three of the polypeptide sequences of SEQ ID NO:17 (SYAMS); SEQ ID NO:18 (TISDGGSYTRYPDKLKG); and SEQ ID NO:19 (VG-GRRDYFDY), which correspond to CDR1, CDR2 and CDR3, respectively, of the heavy chain sequence of SEQ ID NO:13, or antibodies or fragments containing combinations of sequences which are at least 80%, 85%, 90%, 95%, 96%, 97%, 98% or 99% identical thereto.

In yet another embodiment, the invention includes antibodies and antibody fragments having binding specificity to FZD7 that possess the same epitopic specificity as an antibody comprising one, two, three, four, five or six CDRs of FZD7-Fab-1291, i.e., SEQ ID NOs:14-19.

In another embodiment of the invention, the antibodies of the invention or fragments thereof comprise, or alternatively consist of, combinations of one or more of the exemplified heavy chain and light chain sequences set forth above, or sequences that are at least 90% or 95% identical thereto. Methods for determining homology between amino acid sequences are well known to those of ordinary skill in the art.

In an additional embodiment, the invention is further directed to polynucleotides encoding antibody polypeptides having binding specificity to FZD7, including the heavy and/or light chains of FZD7-Fab-1291 as well as fragments, variants, combinations of one or more of the FRs, CDRs, the variable heavy chain and variable light chain sequences, and the heavy chain and light chain sequences set forth above, including all of them or sequences which are at least 90% or 95% identical thereto.

chFZD7-1791

In one embodiment, the invention includes antibodies and antibody fragments having binding specificity to FZD7 that possess a light chain sequence comprising the sequence set forth below:

```
                                                    (SEQ ID NO: 20)
MDMRVPAQLLGLLLLWLPGAKCDIVMTQSPKSMSMSVGERVTLRCKASEN

VLNYVSWYQQKPEQSPKLLIYGASNRYTGVPDRFTGSGSATDFTLTISSV

QAEDLADYHCGQSYRYPTFGAGTKLELKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC
```

In another embodiment, the invention includes antibodies and antibody fragments having binding specificity to FZD7 that possess a heavy chain sequence comprising the sequence set forth below:

```
                                                    (SEQ ID NO: 21)
MDMRVPAQLLGLLLLWLPGAKCEVQPVESGGGLVQPKGSLKLSCAASGFT

FNTYAMHWVRQAPGKGLEWVARIRSKSNNYAKNYDDSVKDRFTISRDDSQ

SMLYLQMNNLKTEDTAMYYCVRENYGGRFDYWGQGTLVTVSSASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK
```

In yet another embodiment, the invention includes antibodies and antibody fragments having binding specificity to FZD7 that possess the same epitopic specificity as chFZD7-1791, i.e., which contains a light chain sequence of SEQ ID NO:20 and a heavy chain sequence of SEQ ID NO:21.

In another embodiment, the invention includes antibodies and antibody fragments having binding specificity to FZD7 that contain one, two, or three of the CDRs of the light chain sequence of SEQ ID NO: 20 (i.e., CDR1, CDR2 and CDR3 correspond to SEQ ID NOs:6-8), and/or which further contain one, two, or three of the CDRs of the heavy chain sequence of SEQ ID NO: 21 (i.e., CDR1, CDR2 and CDR3 correspond to SEQ ID NOs:9-11), or antibodies or fragments containing combinations of sequences which are at least 80%, 85%, 90%, 95%, 96%, 97%, 98% or 99% identical thereto.

In another embodiment of the invention, the antibodies of the invention or fragments thereof comprise, or alternatively consist of, combinations of one or more of the exemplified heavy chain and light chain sequences set forth above, or sequences that are at least 90% or 95% identical thereto.

In an additional embodiment, the invention is further directed to polynucleotides encoding antibody polypeptides having binding specificity to FZD7, including the heavy and/or light chains of chFZD7-1791 as well as fragments, variants, combinations of one or more of the FRs, CDRs, the variable heavy chain and variable light chain sequences, and the heavy chain and light chain sequences set forth above, including all of them or sequences which are at least 90% or 95% identical thereto. Methods for determining homology between amino acid sequences are well known to those of ordinary skill in the art.

In a further particularly preferred embodiment of the invention, antibody fragments comprise, or alternatively consist of, Fab (fragment antigen binding) fragments having binding specificity for FZD7. With respect to antibody chFZD7-1791, the Fab fragment preferably includes the variable region within the light chain sequence of SEQ ID NO: 18 and the variable region within the heavy chain sequence of SEQ ID NO: 19 or sequences that are at least 90%, 95%, 96%, 97%, 98% or 99% identical thereto. This embodiment of the invention further includes Fabs containing additions, deletions, and variants of SEQ ID NO: 20 and/or SEQ ID NO: 21 that retain the binding specificity for FZD7.

In one embodiment of the invention described herein, Fab fragments may be produced by enzymatic digestion (e.g., papain) of chFZD7-1791.

chFZD7-1291

In one embodiment, the invention includes antibodies and antibody fragments having binding specificity to FZD7 that possess a light chain sequence comprising the sequence set forth below:

(SEQ ID NO: 22)
MDMRVPAQLLGLLLLWLPGAKCDVVMSQSPSSLAVSVGEKVTMSCKSSQS

LLYSSNQKNYLAWYQQKPGQSPKLLIYWASTRESGVPDRFTGSGSGTDFT

LTISSVKAKDLAVYYCQQYYSYPTFGGGTKLEIKRTVAAPSVFIFPPSDE

QLKSGTASVVCLLNNFYPREAKVQWKVDNALQSGNSQESVTEQDSKDSTY

SISSTLTLSKADYEKHKVYACEVTHQGLSSPVTKSFNRGEC

In another embodiment, the invention includes antibodies and antibody fragments having binding specificity to FZD7 that possess a heavy chain sequence comprising the sequence set forth below:

(SEQ ID NO: 23)
MDMRVPAQLLGLLLLWLPGAKCEVQLVESGGGLVKPGGSLKLSCAASGFT

FSSYAMSWVRQTPEKRLEWVATISDGGSYTRYPDKLKGRFTISRDNAKNN

LYLQMSHLKSEDTAMYYCARVGGRRDYFDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK

In yet another embodiment, the invention includes antibodies and antibody fragments having binding specificity to FZD7 that possess the same epitopic specificity as chFZD7-1291, i.e., which contains a light chain sequence of SEQ ID NO:22 and a heavy chain sequence of SEQ ID NO:23.

In another embodiment, the invention includes antibodies and antibody fragments having binding specificity to FZD7 that contain one, two, or three of the CDRs of the light chain sequence of SEQ ID NO: 22 (i.e., CDR1, CDR2 and CDR3 correspond to SEQ ID NOs:14-16), and/or which further contain one, two, or three of the CDRs of the heavy chain sequence of SEQ ID NO: 23 (i.e., CDR1, CDR2 and CDR3 correspond to SEQ ID NOs:17-19), or antibodies or fragments containing combinations of sequences which are at least 80%, 85%, 90%, 95%, 96%, 97%, 98% or 99% identical thereto.

In another embodiment of the invention, the antibodies of the invention or fragments thereof comprise, or alternatively consist of, combinations of one or more of the exemplified heavy chain and light chain sequences set forth above, or sequences that are at least 90% or 95% identical thereto.

In an additional embodiment, the invention is further directed to polynucleotides encoding antibody polypeptides having binding specificity to FZD7, including the heavy and/or light chains of chFZD7-1291 as well as fragments, variants, combinations of one or more of the FRs, CDRs, the variable heavy chain and variable light chain sequences, and the heavy chain and light chain sequences set forth above, including all of them or sequences which are at least 90% or 95% identical thereto. Methods for determining homology between amino acid sequences are well known to those of ordinary skill in the art.

In a further particularly preferred embodiment of the invention, antibody fragments comprise, or alternatively consist of, Fab (fragment antigen binding) fragments having binding specificity for FZD7. With respect to antibody chFZD7-1291, the Fab fragment preferably includes the variable region within the light chain sequence of SEQ ID NO: 22 and the variable region within the heavy chain sequence of SEQ ID NO: 23 or sequences that are at least 90%, 95%, 96%, 97%, 98% or 99% identical thereto. This embodiment of the invention further includes Fabs containing additions, deletions, and variants of SEQ ID NO: 22 and/or SEQ ID NO: 23 that retain the binding specificity for FZD7.

In one embodiment of the invention described herein, Fab fragments may be produced by enzymatic digestion (e.g., papain) of chFZD7-1291.

In another embodiment, the invention contemplates an isolated anti-FZD7 antibody comprising a light chain polypeptide sequence selected from: SEQ ID NO:4, SEQ ID NO:12, SEQ ID NO:20, SEQ ID NO:22, or a variant thereof; and further comprising a heavy chain polypeptide sequence selected from: SEQ ID NO:5, SEQ ID NO:13, SEQ ID NO:21, SEQ ID NO:23, or a variant thereof, wherein one or more of the framework residues (FR residues) and/or CDR residues in said light or heavy chain polypeptides has been substituted with another amino acid residue resulting in an anti-FZD7 antibody that retains the ability to specifically bind FZD7 without substantially interacting with (binding to) other FZD family members.

In some aspects, the invention provides an isolated antibody or antibody fragment that competes for binding to FZD7 with an antibody or antibody fragment disclosed herein.

In other aspects, the invention provides an antibody or antibody fragment that selectively binds to FZD7, wherein the antibody or antibody fragment binds to FZD7 with a $K_D$ of less than or equal to $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, or $10^{-13}$ M; preferably, with a $K_D$ of less than or equal to $5 \times 10^{-10}$ M, $10^{-10}$ M, $5 \times 10^{-11}$ M, $10^{-11}$ M, $5 \times 10^{-12}$ M, or $10^{-12}$ M. Preferably, the anti-FZD7 antibody or antibody fragment has no cross-reactivity or minimal cross-reactivity with other FZD family members.

The inventive antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies or fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and fragments thereof may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh inure, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

There are a number of attachment methods available to those skilled in the art, See e.g., EP 0 401 384, herein incorporated by reference (coupling PEG to G-CSF); and Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof). Alternatively, albumin may be used.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodaniine, fluorescein, fluorescein isothiocyanate, umbelliferone, dichlorotriazinylamine, phycoerythrin, and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Methods are known in the art for conjugating an antibody or binding fragment thereof to a detectable moiety and the like, such as for example those methods described by Hunter et al., *Nature* 144:945 (1962); David et al., *Biochemistry* 13:1014 (1974); Pain et al., *J. Immunol. Meth.* 40:219 (1981); and Nygren, *J., Histochem. and Cytochem.* 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention further contemplates the generation and use of antibodies that bind any of the foregoing sequences, including, but not limited to, anti-idiotypic antibodies. In an exemplary embodiment, such an anti-idiotypic antibody could be administered to a subject who has received an anti-FZD7 antibody to modulate, reduce, or neutralize, the effect of the anti-FZD7 antibody. Such antibodies could also be useful for treatment of an autoimmune disease characterized by the presence of anti-FZD7 antibodies. A further exemplary use of such antibodies, e.g., anti-idiotypic antibodies, is for detection of the anti-FZD7 antibodies of the present invention, for example to monitor the levels of the anti-FZD7 antibodies present in a subject's blood or other bodily fluids. For example, in one embodiment, the invention provides a method of using the anti-idiotypic antibody to monitor the in vivo levels of said anti-FZD7 antibody or antibody fragment in a subject or to neutralize said anti-FZD7 antibody in a subject being administered said anti-FZD7 antibody or antibody fragment.

Methods of Producing Anti-FZD7 Antibodies and Binding Fragments Thereof that Specifically Bind Human FZD7

The invention also includes human, humanized and chimeric forms of these antibodies. Methods of producing such antibodies are well known to those of ordinary skill in the art. The antibodies may optionally be produced in mammalian cells (such as CHO cells), bacterial cells, yeast cells, or other cells or using cell-free methods as known in the art.

For example, methods of producing chimeric antibodies are now well known in the art (See, for example, U.S. Pat. No. 4,816,567 to Cabilly et al.; Morrison et al., *P.N.A.S. USA*, 81:8651-55 (1984); Neuberger et al., *Nature* 314:268-270 (1985); Boulianne, G. L. et al., *Nature* 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al., *Nature* 321:522-525 (1986); Reichmann, L. et al., *Nature* 332:323-327 (1988); Verhoeyen M et al., *Science* 239:1534-36 (1988), the disclosures of each of which are herein incorporated by reference in their entireties).

Antibody polypeptides of the invention having FZD7 binding specificity may also be produced by constructing, using conventional techniques well known to those of ordinary skill in the art, an expression vector containing a promoter (optionally as a component of a eukaryotic or prokaryotic operon) and a DNA sequence encoding an antibody heavy chain in which the DNA sequence encoding the CDRs required for antibody specificity is derived from a non-human cell source, while the DNA sequence encoding the remaining parts of the antibody chain is derived from a human cell source.

A second expression vector is produced using the same conventional means well known to those of ordinary skill in the art, said expression vector containing a promoter (optionally as a component of a eukaryotic or prokaryotic operon) and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding a promoter (optionally as a component of a eukaryotic or prokaryotic operon) and a light chain-derived polypeptide and the second vector containing DNA encoding a promoter (optionally as a component of a eukaryotic or prokaryotic operon) and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be a bacterial cell, such as *E. coli*, or a eukaryotic cell, such as a mammalian cell of a well-defined type for this purpose, such as, e.g., a myeloma cell, a Chinese hamster ovary (CHO) cell line, a NSO cell line, or a HEK293 cell line may be used.

The antibodies may optionally be produced in mammalian cells (such as CHO cells), bacterial cells, yeast cells, or other cells or using cell-free methods as known in the art.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al., *Science* 253: 792-795 (1991), the contents of which is herein incorporated by reference in its entirety.

The chimeric and humanized antibodies may include an Fc derived from IgG1, IgG2, IgG3, or IgG4 constant regions.

The invention is further directed to polynucleotides encoding antibodies and antibody fragments having binding specificity to FZD7.

Host cells and vectors comprising said polynucleotides are also contemplated.

In some aspects, the invention provides a vector comprising a nucleic acid molecule encoding an anti-FZD7 antibody or fragment thereof as disclosed herein. In some embodiments, the invention provides a host cell comprising a nucleic acid molecule encoding an anti-FZD7 antibody or fragment thereof as disclosed herein.

Diagnostic Uses of Anti-FZD7 Antibodies and Binding Fragments Thereof that Specifically Bind Human FZD7

This disclosure also provides methods of detecting a cancer cell that expresses FZD7. Detecting the expression of FZD7 may be used for diagnosis and staging of cancers (e.g., in immunohistochemistry). For example, the level or extent of expression of FZD7 may indicate the stage of cancer, may be correlated with patient outcome, or may be predictive of the outcome of different treatment options.

The antibody-epitope complex may be detected by Western blot, radioimmunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay.

The sample may be sample is a tissue biopsy, lymph, urine, cerebrospinal fluid, amniotic fluid, inflammatory exudate, blood, serum, stool, or liquid collected from the colorectal tract. Numerous well known tissue or fluid collection methods can be utilized to collect the biological sample from the subject in order to determine the level of DNA, RNA and/or polypeptide of the marker of interest in the subject. Examples of tissue or fluid collection methods include, but are not limited to, fine needle biopsy, needle biopsy, core needle biopsy and surgical biopsy (e.g., brain biopsy), and lavage. Regardless of the procedure employed, once a biopsy/sample is obtained the level of the marker may be determined and a diagnosis can thus be made.

The antibodies and antibody fragments that selectively bind an FZD7 antigen may be used in diagnostic methods for detecting the presence or absence of an FZD7 antigen, wherein the presence of the antigen is indicative of cancer including but not limited to skin, liver, blood, brain, breast and ovary. The diagnostic methods may be used with patients at risk of cancer or patients without symptoms.

Each marker of the present invention may be used alone or in combination, for various uses, including but not limited to, prognosis, prediction, screening, early diagnosis, determination of progression, therapy selection and treatment monitoring of a cancer (e.g., ovarian, breast, renal or glioblastoma).

The cancers that may be detected using the methods described herein include but are not limited to non-solid and solid tumors, cancer of the ovary, breast, kidney or brain, and wherein the cancer may be invasive or metastatic.

The FZD7 antigen may be used as a cancer biomarker, i.e., if the marker concentration is above or below the threshold level (depending upon the marker and/or the diagnostic test being performed), the marker concentration correlates with the disease or condition. Typically the level of FZD7 in a biological sample obtained from the subject is different (i.e., increased or decreased) from the level of FZD7 in a similar sample obtained from a healthy individual (examples of biological samples are described herein).

Determining the level of the same marker in normal tissues of the same origin may be effected along-side to detect an elevated expression and/or amplification and/or a decreased expression, of the marker as opposed to the normal tissues.

Detection of the FZD7 antigen in a biological sample, such as a subject's serum or biopsied neoplastic cells, may be performed by means of the anti-FZD7 antigen antibody or antigen-binding fragment thereof. For example, a biological sample (e.g., tissue or serum) is obtained from a subject, then FZD7 antigen is measured (e.g., by ELISA or PCR), and compared with corresponding samples from normal subjects. Measuring methods include any method of nucleic acid detection, for example in situ hybridization using antisense DNA or cRNA oligonucleotide probes, ultra-high throughput sequencing, nanostring technology, microarrays, rolling circle amplification, proximity-mediated ligation, PCR, qRT-PCR ChIP, ChIP-qPCR, or FZD7 antigen-binding antibodies or fragments thereof. Comparatively high levels of FZD7 indicate the presence and/or severity of cancer, e.g., skin, liver, blood, brain, breast and ovary, and may indicate metastasis or poor cancer prognosis.

Currently, depending on the stage of the cancer, cancer treatment involves one or a combination of the following therapies: surgery to remove the cancerous tissue, radiation therapy, and chemotherapy. Detection of cancer cells using an antibody to FZD7 can be used in conjunction with one or more therapies. FZD7 expression is highly restricted, with limited expression in adult tissues. Therefore, therapy may be targeted to the cancer cells thereby promoting effective treatment and/or reducing the effect on normal non-cancerous tissue. The therapeutic course (e.g., regimen and dosages of radiotherapy, surgical plan, or course of cryotherapy) that are therapeutically effective will depend on the particular cancer being treated, the extent of the disease and other factors familiar to the physician of skill in the art and can be determined by the physician.

Expression of FZD7 may be evaluated using an in vivo diagnostic assay, e.g., by administering an antibody that specifically binds to FZD7 and is tagged with a detectable label (e.g., a radioactive isotope or a fluorescent label) and externally scanning the patient for localization of the label. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody. Aside from the above assays, various in vivo and in vitro assays for detecting the presence of a cancer-associated antigen are available to the skilled practitioner.

The antibodies may also be used for purification or immunoprecipitation of FZD7 from cells or other samples, for detection and quantitation of cancer-associated antigen in vitro, e.g., in an ELISA or a Western blot, to kill and eliminate cancer-associated antigen-expressing cells from a population of mixed cells, e.g., as a step in the purification of other cells.

In another aspect, the invention provides a diagnostic kit comprising an FZD7 specific antibody or antibody fragment, such as FZD7-Fab-1791, FZD7-Fab-1291, chFZD7-1791, or chFZD7-1291. In one embodiment, the antibody or antibody fragment may be directly or indirectly fixed to a solid phase support, such as a bead, plate, matrix, polymer, test tube, sheet, culture dish, or test strip. In another embodiment, the solid support may be an array.

In yet another embodiment, the invention concerns an article of manufacture comprising a container and a composition of matter contained within the container, wherein the composition of matter comprises an anti-FZD7 antibody or antibody fragment as described herein (such as FZD7-Fab-1791, FZD7-Fab-1291, chFZD7-1791, or chFZD7-1291). The article may further optionally comprise a label affixed to the container, or a package insert included with the container, that refers to the use of the composition of matter for the diagnostic detection of a tumor, preferably a solid tumor, more preferably a tumor associated with ovarian cancer, breast cancer, renal cancer or glioblastoma.

Therapeutic Uses of Anti-FZD7 Antibodies and Binding Fragments Thereof that Specifically Bind Human FZD7

This disclosure further provides therapeutic methods of use for the anti-FZD7 antibodies and antibody fragments. In one aspect, anti-FZD7 antibodies and antibody fragments described herein are useful for ameliorating or reducing the symptoms of, or treating, or preventing, diseases and disorders associated with aberrant FZD7, e.g., overexpression, expression in tissues where the gene is not "normally" expressed, etc in a subject or individual.

By "subject" or "individual" is included any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species. However, in certain preferred embodiments, the subject or individual is human, e.g., a subject with cancer or pre-disposed to developing cancer, or a person with a condition caused, at least in part, by WNT signaling via FZD7.

Anti-FZD7 antibodies described herein, or fragments thereof, as well as combinations, can be administered in a therapeutically effective amount to patients in need of treatment of diseases and disorders associated with aberrant FZD7 expression, e.g., cancer, in the form of a pharmaceutical composition as described in greater detail below.

The term "patient" refers to a living organism suffering from or prone to a condition that can be prevented or treated by the treatment regimen the invention, and includes both humans and animals.

In one embodiment of the invention, anti-FZD7 antibodies described herein, or fragments thereof, are useful (either alone or in combination with another agent) for ameliorating or reducing the symptoms of, or treating, or preventing cancer. "Cancer," as used herein, refers broadly to any neoplastic disease (whether invasive or metastatic) characterized by abnormal and uncontrolled cell division causing malignant growth or tumor. The anti-FZD7 antibodies and antigen-binding fragments thereof can be used for ameliorating or reducing the symptoms of, or treating, or preventing solid tumors and non-solid tumors. Preferably, the anti-FZD7 antibodies and antigen-binding fragments thereof can be used for ameliorating or reducing the symptoms of, or treating, or preventing ovarian cancer, breast cancer, renal cancer and/or glioblastoma.

In one embodiment of the invention, the anti-FZD7 antibodies described herein, or antigen-binding fragments thereof, as well as combinations of said antibodies or antibody fragments, are administered to a subject at a concentration of between 0.1 mg/ml and about any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or 200 mg/ml+/−10% error.

In another embodiment of the invention, the anti-FZD7 antibodies and fragments thereof described herein are administered to a subject at a dose of between about 0.01 and 100.0 or 200.0 mg/kg of body weight of the recipient subject. In certain embodiments, depending on the type and severity of the FZD7-related disease, about 1 µg/kg to 50 mg/kg (e.g., 0.1-20 mg/kg) of antibody is an initial candidate dosage for administration to the patient, whether, for example, by one or more separate administrations, or by continuous infusion. In another embodiment, about 1 µs/kg to 15 mg/kg (e.g., 0.1 mg/kg-10 mg/kg) of antibody is an initial candidate dosage for administration to the patient. A typical daily dosage might range from about 1 µg/kg to 100 mg/kg or more, depending on several factors, e.g., the particular mammal being treated, the clinical condition of the individual patient, the cause of the disorder, the site of delivery of the agent, the method of administration, the scheduling of administration, and other factors known to medical practitioners. However, other dosage regimens may be useful.

For example, in addition to the relative dosages (mg/kg) discussed herein, the subject anti-FZD7 antibodies and fragments thereof can be administered to a subject at an absolute dose (mg). Accordingly, in one embodiment of the invention, the anti-FZD7 antibodies and fragments thereof described herein are administered to a subject at a dose of between about 1 microgram and about 100 milligrams regardless of the route of administration.

According to preferred embodiments, the antibody containing medicament or pharmaceutical composition is peripherally administered to a subject via a route selected from one or more of; orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-FZD7 antibodies described herein, or FZD7 binding fragments thereof, as well as combinations of said antibodies or antibody fragments, are administered to a subject in a pharmaceutical formulation. In a preferred embodiment, the subject is a human.

A "pharmaceutical composition" or "medicament" refers to a chemical or biological composition suitable for administration to a subject, preferably a mammal, more preferably a human. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-FZD7 antibodies described herein, or FZD7 binding fragments thereof, as well as combinations of said antibodies or antibody fragments, may be optionally administered in combination with one or more active anti-cancer agents.

Non-limiting, exemplary anti-cancer/chemotherapeutic agents include, but are not limited to, the following: alkylating agents (including, without limitation, nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazinc (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafururacil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-[4-phenyl-1-piperazinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis [(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl) amino]-4-methylphenyl]-(9Cl); cyclin dependent kinase inhibitors which include without limitation olomoucine and its derivatives, purvalanol B, roascovitine indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar®) and its derivatives (e.g., as disclosed generically and specifically in U.S. Pat. No. 5,260, 291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(9Cl), Bisindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase II elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, 19$^{th}$ Ed., Grennaro, A., Ed., 1995, which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Absorption of the injectable compositions can be prolonged by including an agent which delays absorption, for example, monostearate salts and gelatin. Moreover, the alkaline polypeptide can be formulated in a time-release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

The entire disclosure of each document cited (including patents, patent applications, journal articles, abstracts, manuals, books, or other disclosures) in the Background of the Invention, Detailed Description, and Examples is herein incorporated by reference in their entireties.

The present invention has been described in detail. In order to further illustrate the present invention and its intrinsic benefits the following examples discussing experiments conducted by the inventors are provided.

Examples

FZD7 Fabs and Intact Chimeric Antibodies.

Using standard antibody engineering techniques, the amino acid sequences for two FZD7-Fabs, FZD7-Fab1291 and FZD7-Fab1791 (see FIG. 1), were inserted into human antibody frameworks to generate chimeric antibodies, chFZD7-1791 and chFZD7-1291 (see FIG. 2).

Epitope Mapping of FZD7 Fabs and Antibodies.

Human FZD7 and mouse Fzd7 are 96.5% identical in their amino acid sequences (see FIG. 3). The Cysteine-rich domain (CRD, amino acids 46-181), the transmembrane (TM) domain region (amino acids 254-549), and the intracellular domain (amino acids 550-574) are identical, with the exception of residue P (Pro) at position 521 between TM6 and TM7. The only notable regions of divergence between human and mouse Fzd7 are in the amino terminus, which encompasses the signal sequence and is likely cleaved co-translationally, and the membrane proximal region between the CRD and the first TM domain (amino acids 172-205). This 34 amino acid region harbors 9 amino acid differences between human and mouse Fzd7.

FZD7-Fab1291 and FZD7-Fab1791 react with human FZD7, but not with mouse Fzd7 protein (see FIG. 4A). Together with the sequence alignment, this data suggests that the binding domain for these two Fabs resides in the membrane proximal region between amino acids 172-205 (domain marked by a green rectangle in FIG. 4B).

A series of point mutations to substitute amino acids in mouse Fzd7 demonstrates that a single amino acid substitution (Proline at 188 to Leucine, P188L) is sufficient to re-create the FZD7-Fab binding domain in mouse Fzd7 (see FIGS. 4C and D). Therefore, the epitope of the FZD7 antibody encompasses the region that contains residue L188.

FZD7 Fabs Block Wnt3a Signaling and Result in FZD7 Protein Downregulation in Cancer Cell Lines.

Figure 5:
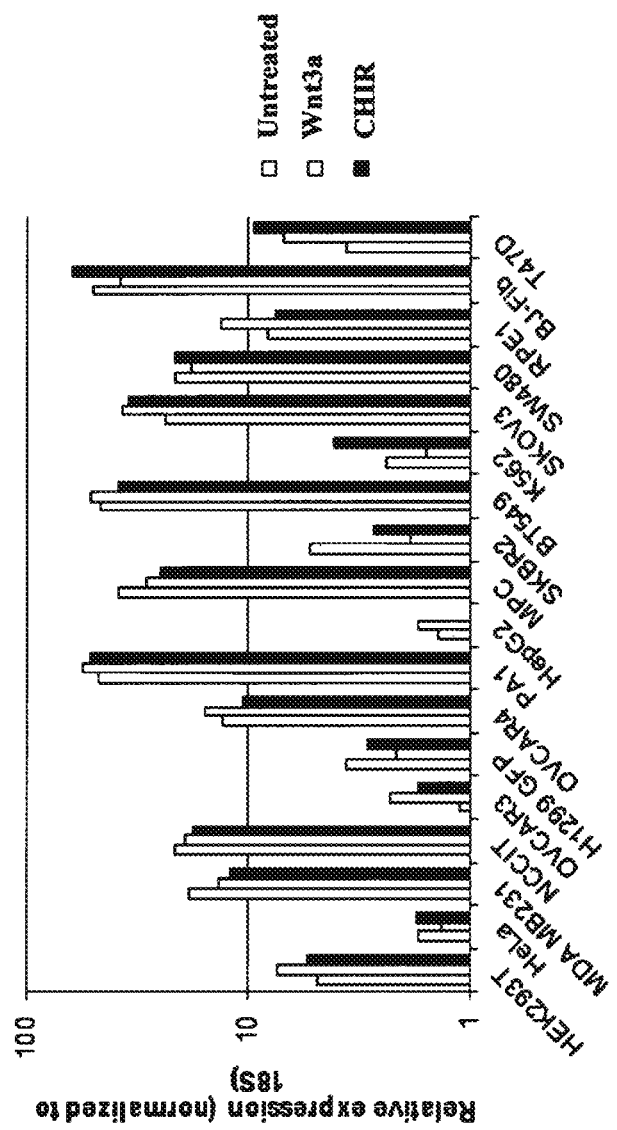
FIG. 5 shows FZD7 expression in different cell lines. Eighteen different cell lines were (i) untreated, (ii) treated with Wnt3a (10 nM), or (iii) treated with CHIR (1 uM) for 24 hours before total RNA was isolated from the cells and qRT-PCR was performed. All values were normalized to the sample with the lowest amount of FZD7 mRNA, i.e., CHIR-treated HepG2 cells. Each of the three bars for each cell line follow the order of (i), (ii), and then (iii) from left to right.

FZD7 mRNA was detected by reverse transcription quantitative PCR (RT-qPCR) in various cell lines (see FIG. 5). Activation of WNT signaling in these cells with either Wnt3a or the GSK3 inhibitor CHIR98014 (CHIR) had minor effects on FZD7 mRNA levels.

As previously described, treatment of human pluripotent stem cells with FZD7-Fab impairs pluripotency (see FIG. 4A in Fernandez et al. 2014), blocks Wnt3a signaling (see FIG. 5A in Fernandez et al. 2014), and leads to downregulation of FZD7 protein (see FIG. 5E in Fernandez et al. 2014).

The effect of FZD7 antibody fragments on OVCAR4 (ovarian carcinoma cell line) and MDA-MB-231 (breast cancer cell line, ATCC # HTB-26) were then tested (FIG. 6). Addition of the FZD7-Fab1791 to MDA-MB-231 cells carrying a WNT responsive reporter, TOP-Flash, led to marked decrease in luciferase reporter activation upon treatment with Wnt3a protein (see FIG. 6A), indicating that the FZD7-Fab blocks Wnt3a signaling in these cells. Treatment of OVCAR-4 cells with Wnt3a, CHIR or FZD7-Fab leads to a decline in FZD7 protein levels (see FIG. 6B), consistent with the observation made in human pluripotent stem cells.

FZD7 Expression is Variable within Cancer Cell Lines.

Figure 7A:
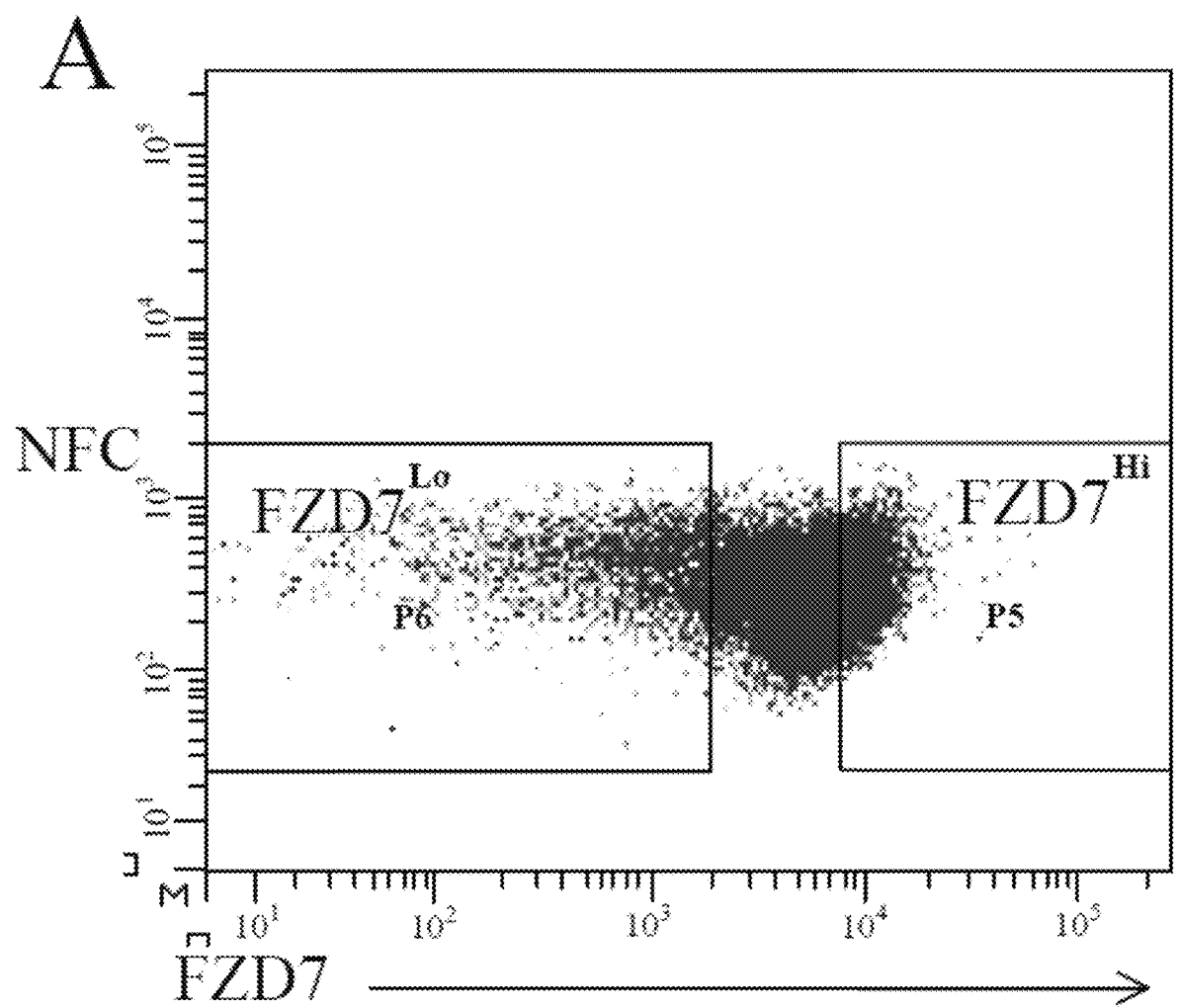
FIGS. 7A and 7B show the characterization of FZD7 expression in an ovarian cancer line, OVCAR4.
Figure 7B:
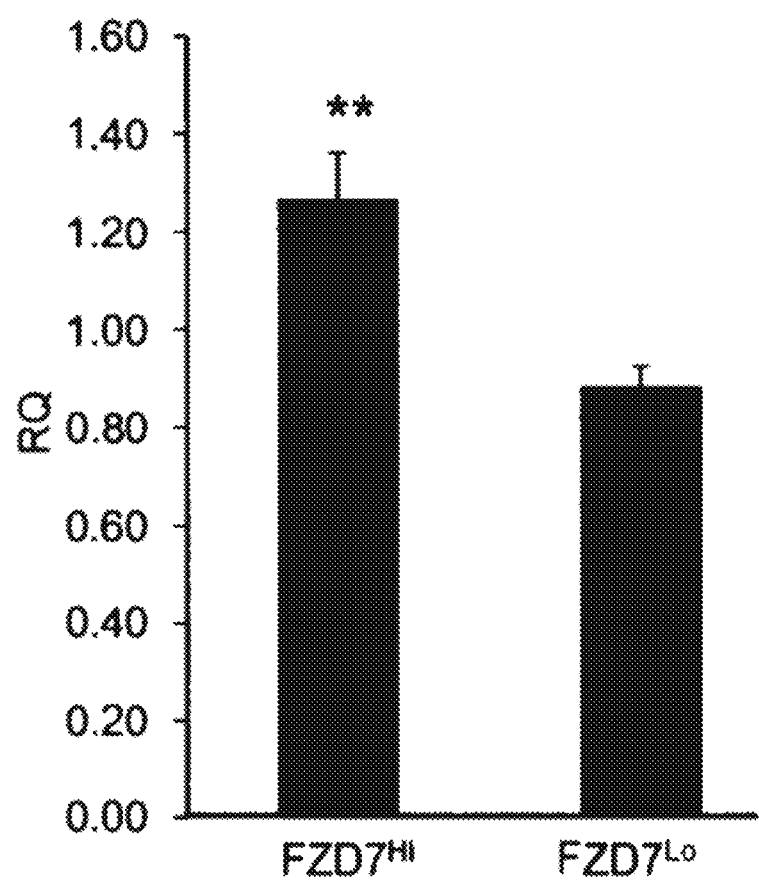
Figure 8A:
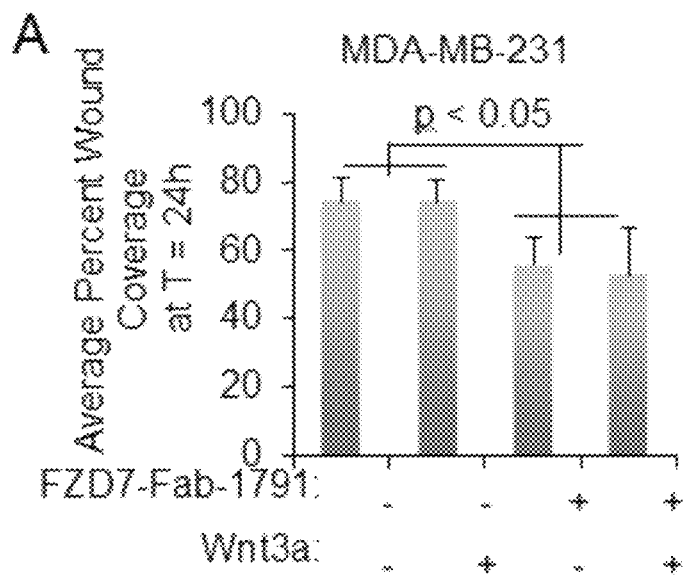
FIGS. 8A and 8B demonstrate that FZD7-Fab-1791 can block migration of cancer cells.
Figure 8B:
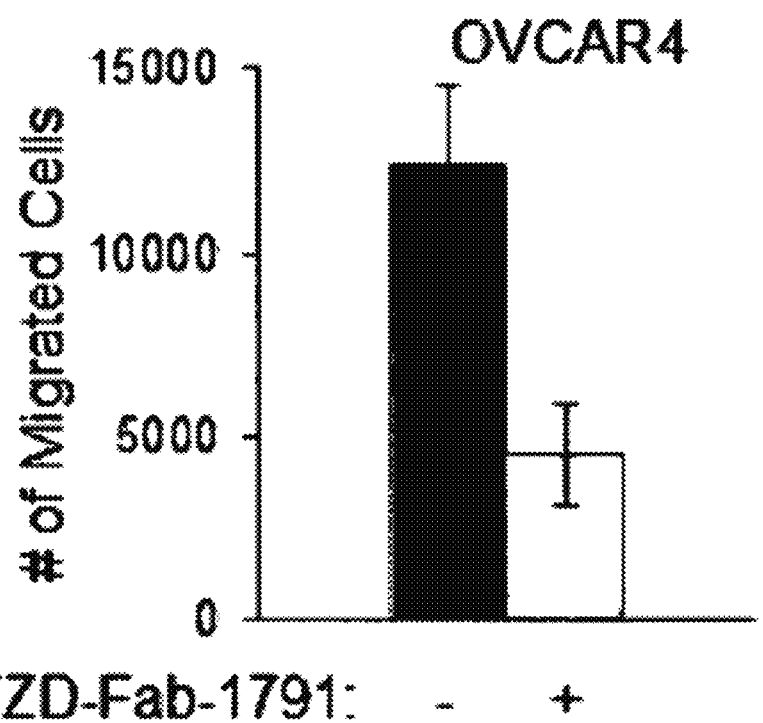
Figure 9:
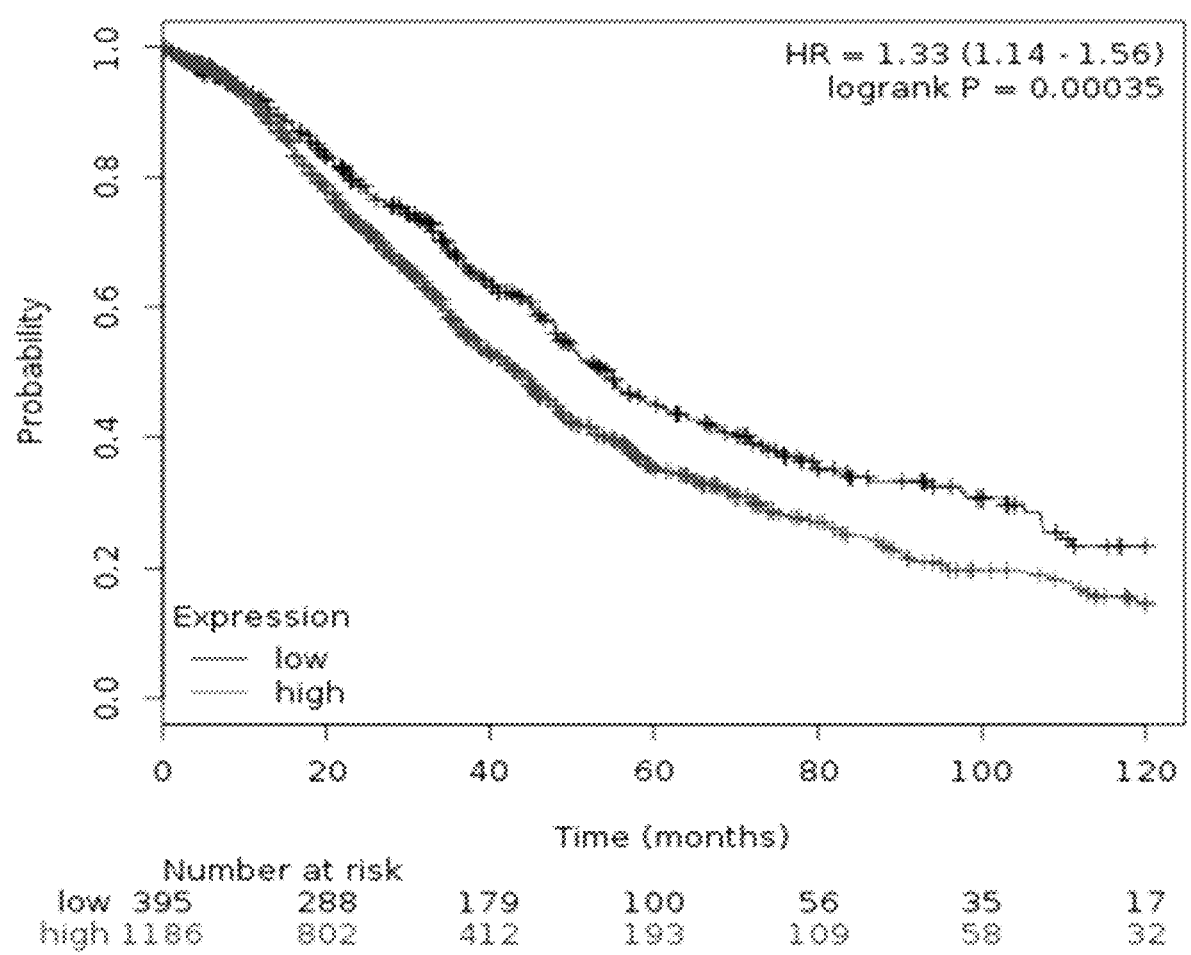
FIG. 9 shows a significant reduction in overall survival of ovarian cancer patients (1581 subjects) with high levels of FZD7 expression.
Figures 11, 11A:
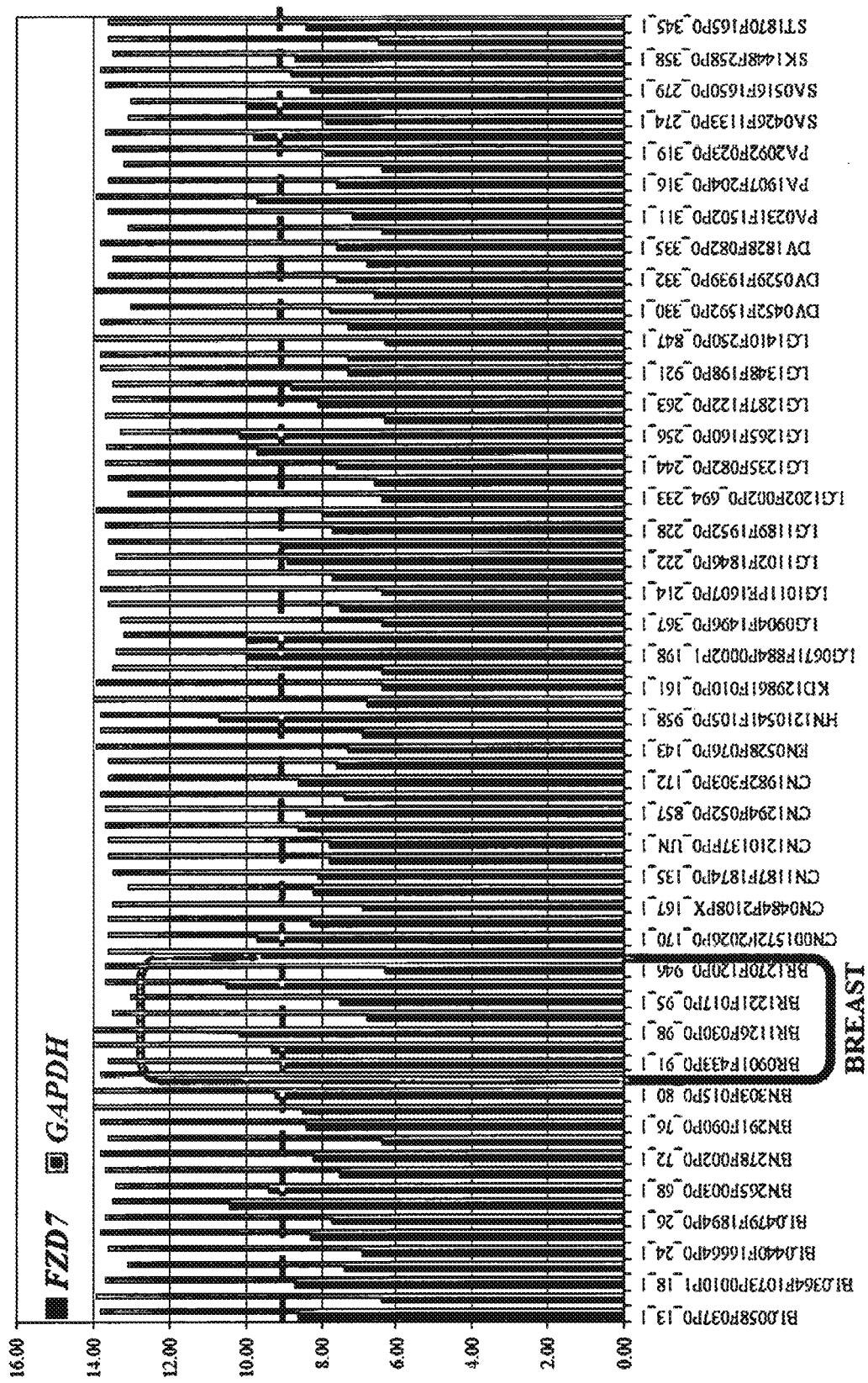
FIGS. 11A and 11B show a correlation between FZD7 expression and cancer. Publically available microarray data from patient derived xenograft (PDX) samples, available from Jackson Laboratory, was downloaded and analyzed for FZD7 expression.
Figure 11B:
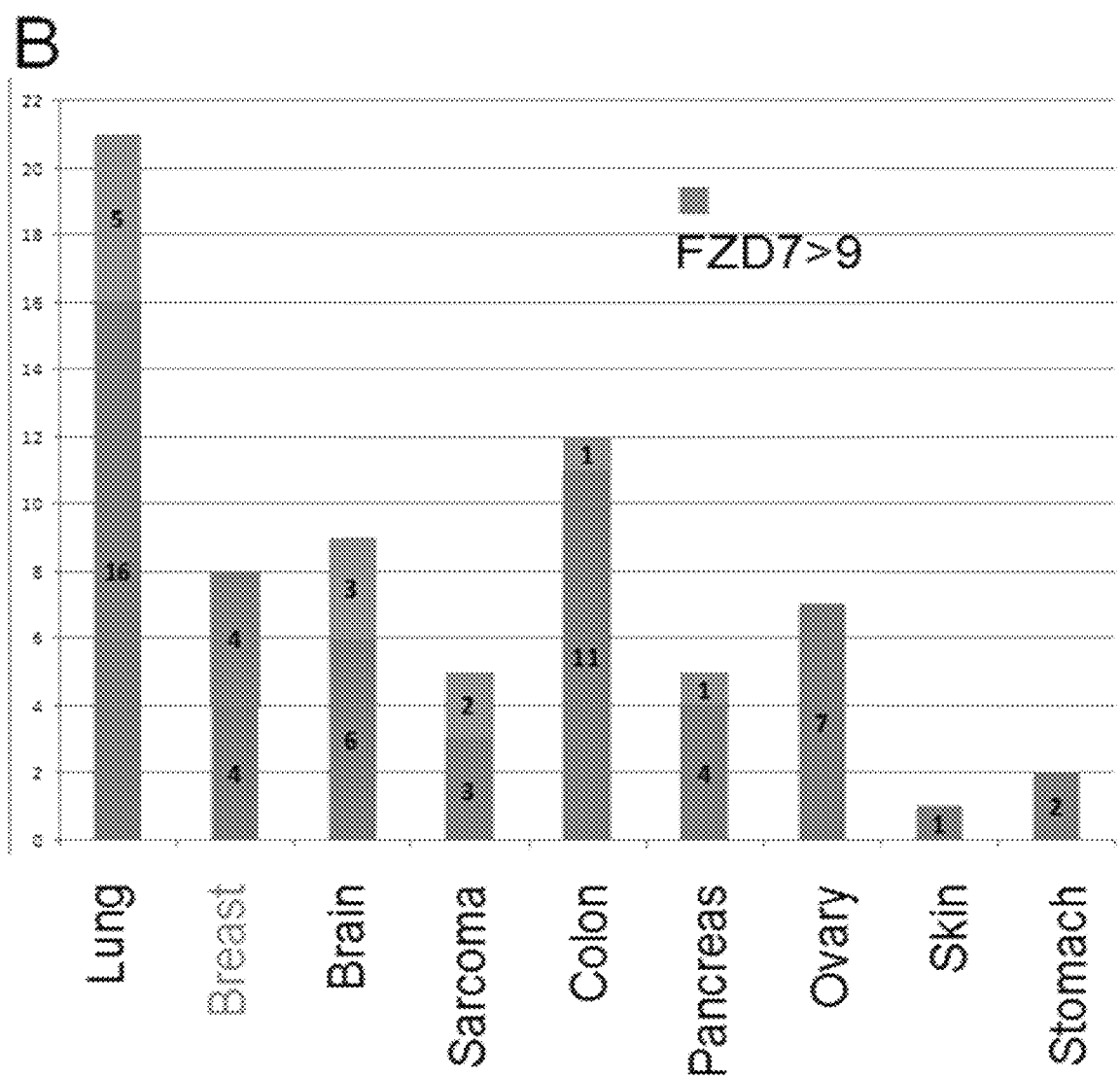

The FZD7-Fabs and antibodies detect FZD7 protein by flow cytometry in human pluripotent stem cells (Fernandez et al. 2014) and in the ovarian carcinoma cell line OVCAR-4 (see FIG. 7A). We used flow cytometry-based cell sorting to isolate OVCAR-4 cells with low and high levels of FZD7 protein on their cell surface ($FZD7^{Lo}$ and $FZD7^{Hi}$, respectively). QPCR of RNA isolated from these two cell populations confirmed that $FZD7^{Hi}$ cells are enriched for FZD7 mRNA relative to $FZD7^{Lo}$ cells (see FIG. 7B).

Generation of a Transgenic Mouse Carrying a "Humanized" Fzd7 Gene.

The CRISPR/Cas9 system will be used to introduce a targeted mutation in the Fzd7 gene, which will result in the replacement of Proline at position 188 of SEQ ID NO: 2 to Leucine. The nuclease Cas9 is guided via RNA to a specific location in the genome and introduces a double stranded break. Parameters for design of optimal guide RNAs are available on line (http://crispr.mit.edu/). Simultaneously, cells will be transduced with a single stranded repair oligo spanning the double-stranded break site. This oligo (50-80 bases in length) is designed to include the desired change, in our case the introduction of a single base change to encode a Leucine rather than a Proline at position 188 of Fzd7. In addition, a silent change will be introduced to create a unique restriction site that will facilitate screening for the presence of the mutation. This method is highly efficient and has been successfully used to generate "knock-in mice" by directly injecting the CRISPR/Cas9 system along with repair oligo into mouse blastocyst (see, e.g., Wang et al., 2013; Yang et al., 2013). Blastocysts will then be transferred into pseudo pregnant mice and live pups will be screened for the presence of the introduced mutation. Targeting efficiencies are often sufficiently high to target both alleles; however, in this case, a single targeted allele would be sufficient.

Once established, the engineered mice will be used to determine potential toxicity associated with the antibodies. Mice carrying the mutated Fzd7 gene will be dosed weekly with antibody at 10 mg/kg. Unless overt toxic effects are observed in the mutant mice (e.g., reduced body size, hair loss, death, etc.), antibody injections will be performed for up to 90 days, at which point animals will be sacrificed and carefully assessed to identify potential adverse effects. Given the observed bone-related adverse effects with the current clinical trial with Vantictumab (OncoMed, see section "Introduction and Review of Relevant Literature"), close attention will be paid to bone mass and density. In addition, since Fzd7 is expressed in the colon crypt (Hughes et al., 2011; Sato et al., 2011), the integrity of the intestinal epithelium will be closely examined. If no effects are observed, dose escalation experiments will be performed.

The engineered mice will also be valuable for studying FZD7 expression domains during development and adult life, which may yield important insights into FZD7 function during development and adult life. Few highly specific antibodies to FZD proteins have been developed, and all of these antibodies are cross-reactive. The subject anti-FZD7 antibodies and antibody fragments, which are only reactive with human FZD7, represent a unique tool to interrogate FZD7 expression and function in the transgenic mouse.

Figure 15:
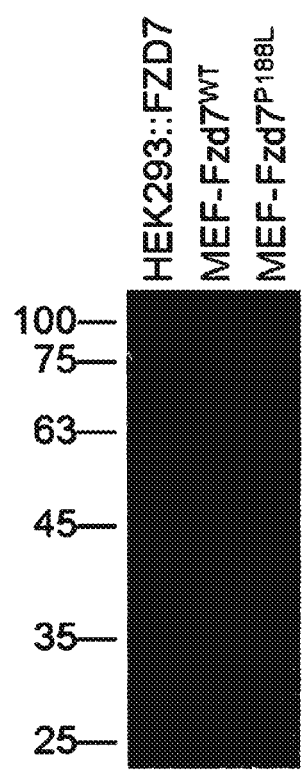
FIG. 15 shows the specificity of the FZD7-specific antibody for mouse Fzd7-P188L. Cell lysates from mouse embryonic fibroblasts (MEF) generated from E13.5 wild-type (MEF-Fzd7WT) and mutant (MEF-Fzd7P188L) embryos were immunoblotted with the FZD7-specific antibody. Only cell lysates from mouse embryos carrying the engineered mutation at position 188 (Proline to Leucine) were reactive with the antibody. HEK293 cells transfected with a human FZD7 expression vector served as positive control.

Generation of Mouse Carrying Mutation P118L in Fzd7 (FIG. 15)

Blastocyst stage mouse embryos were injected with mRNA encoding Cas9, a guide RNA targeting Fzd7 near the codon encoding P188, and a double-stranded DNA repair oligo (sequence provided below), and subsequently transferred into pseudopregnant recipients. The genotypes of F0 pups at the site of the engineered mutation were determined by sequencing of PCR products obtained from genomic DNA isolated from ear punch biopsies. Animals homozygous for the desired mutation were viable and were crossed to maintain a colony of mice carrying the homozygous mutation that produces a Fzd7 protein with a substitution from proline to leucine at position 188.

CRISPR/Cas9 repair oligo:
(SEQ ID NO: 37)
GACGGCTCCGGGGGCGCGGGCGGCAGTCCCACCGCCTACCCTACTGCTCC

CTACCTGCCAGATCTACCTTTCACTGCGATGTCCCCCTCAGATGGCAGAG

GCCGCTTGTCTTTCCCCTTCTCGTGTCCGCGC

PCR primers:
(SEQ ID NO: 38)
TGGGGCAGAACACGTCCG
and
(SEQ ID NO: 39)
GAAGAGCGTCGAGGCGCAGC.

Sequencing primer:
(SEQ ID NO: 40)
GCTCACCTAGGAAGCGGTAG.

Reactivity of FZD7 Antibody with Mouse Fzd7_P188L

E13.5 embryos from breeding mice homozygous for the Fzd7_P188L mutation were dissociated and plated in standard cell culture conditions to establish a mouse embryonic fibroblast (MEF) culture. Cell lysates of passage 2 MEFs were immunoblotted with the FZD7-specific antibody. Only cell lysates from mouse embryos carrying the engineered mutation at position 188 (Proline to Leucine) were reactive with the antibody (FIG. 15). HEK293 cells transfected with a human FZD7 expression vector served as positive control.

Generation of FZD7 Polypeptides Encompassing Leucine 188

DNA oligos encoding the peptide sequence of FZD7 from G168 to S209 (sequences below) were ligated into plasmid pGEX4T3 digested with EcoRI and XhoI. The resulting plasmids were transformed into bacteria, and GST fusion proteins (FIG. 14A and FIG. 14B) were expressed and purified using Glutathione Sepharose beads. Purified GST fusion proteins were immunoblotted with the FZD7-specific antibody.

Oligo sequence to generate peptide with L188:
(SEQ ID NO: 41)
GAATTCCGGCTCCGGGGGCCCAGGCGGCGGCCCCACTGCCTACCCTACCG

CGCCCTACCTGCCGGACCTGCCCTTCACCGCGCTGCCCCCGGGGGCCTCA

GATGGCAGGGGGCGTCCCGCCTTCCCCTTCTCCTCGAG.

Oligo sequence to generate peptide with P188:
(SEQ ID NO: 42)
GAATTCCGGCTCCGGGGGCCCAGGCGGCGGCCCCACTGCCTACCCTACCG

CGCCCTACCTGCCGGACCCGCCCTTCACCGCGCTGCCCCCGGGGGCCTCA

GATGGCAGGGGGCGTCCCGCCTTCCCCTTCTCCTCGAG

Figure 14C:
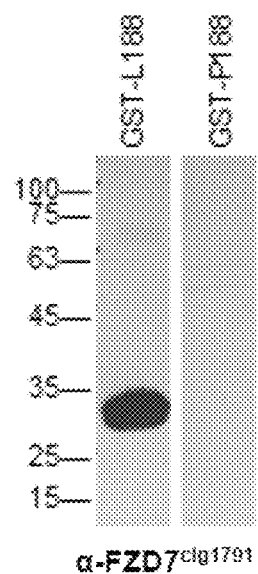
Figure 14D:
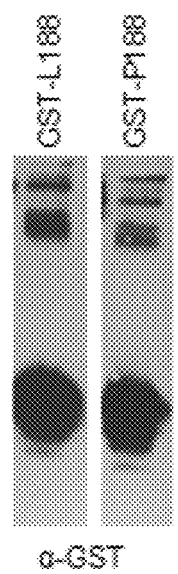

L188 represents the wildtype sequence recognized by the FZD7-specific antibody (FIG. 14C). P188 represents the mutant sequence that is not recognized by the antibody (FIG. 14C). αGST served as a control (FIG. 14D).

Blocking Spheroid Formation of Cell Lines with FZD7 Antibody

Figure 13:
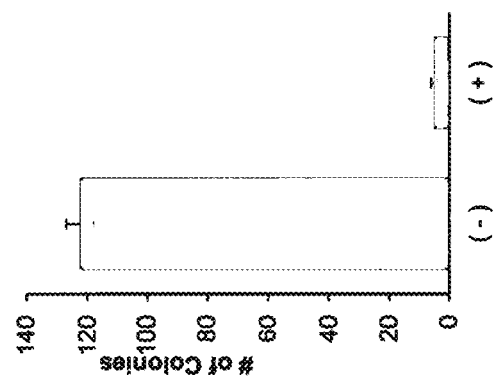
FIG. 13A and FIG. 13B shows a clonogenicity assay of GBM cell line. The GBM line TS528 was seeded at low density in wells of a 24 well plate (600 cells per well). Each well of this 24 well plate contained 1,200 microwells, each 300 µm in diameter and 200 µm in depth. Cells were allowed to grow for 10 days in the absence (FIG. 13A, top panel, "untreated") or presence (FIG. 13A, bottom panel, "+FZD7-Ig") FZD7-specific antibody.
Figure 13B:
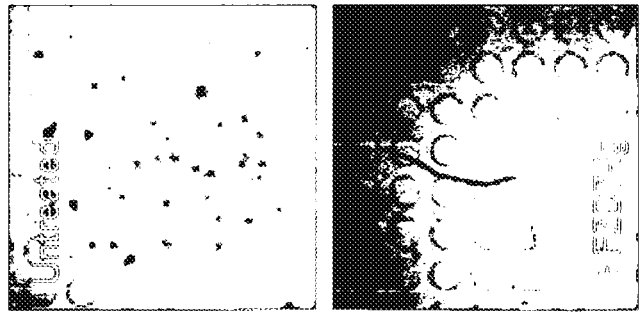

Human cell lines were seeded at a density of 600 cells per well of a 24-well plate. Each well contained 1,200 microwells of 300 μm in diameter and 200 μm in depth. Cells were cultured for 7-10 days in the presence (FIG. 13A, bottom panel, "+FZD7-Ig") or absence (FIG. 13A, top panel, "untreated") of 1-5 ug/mL FZD7-specific antibody. Spheres were quantified by counting under a light microscope. The presence of FZD7-specific antibody was shown to block spheroid formation of human cell lines (FIG. 13B).

REFERENCES

The following references are cited in this patent application. The content of each of these references are incorporated in their entirety herein.

Asad, M., Wong, M. K., Tan, T. Z., Choolani, M., Low, J., Mori, S., Virshup, D., Thiery, J. P., and Huang, R. Y. (2014). FZD7 drives in vitro aggressiveness in Stem-A subtype of ovarian cancer via regulation of non-canonical Wnt/PCP pathway. Cell death & disease 5, e1346. PMCID: PMC4123093

Cancer Genome Atlas, N. (2012). Comprehensive molecular characterization of human colon and rectal cancer. Nature 487, 330-337. PMCID: PMC3401966

Chakrabarti, R., Wei, Y., Hwang, J., Hang, X., Andres Blanco, M., Choudhury, A., Tiede, B., Romano, R. A., DeCoste, C., Mercatali, L., et al. (2014). DeltaNp63 promotes stem cell activity in mammary gland development and basal-like breast cancer by enhancing Fzd7 expression and Wnt signalling. Nature cell biology 16, 1004-1015. PMCID: PMC4183725

Fernandez, A., Huggins, I. J., Perna, L., Brafman, D., Lu, D., Yao, S., Gaasterland, T., Carson, D. A., and Willert, K. (2014). The WNT receptor FZD7 is required for maintenance of the pluripotent state in human embryonic stem cells. Proceedings of the National Academy of Sciences of the United States of America 111, 1409-1414. PMCID: PMC3910637

Gurney, A., Axelrod, F., Bond, C. J., Cain, J., Chartier, C., Donigan, L., Fischer, M., Chaudhari, A., Ji, M., Kapoun, A. M., et al. (2012). Wnt pathway inhibition via the targeting of Frizzled receptors results in decreased growth and tumorigenicity of human tumors. Proceedings of the National Academy of Sciences of the United States of America 109, 11717-11722. PMCID: PMC3406803

Hughes, K. R., Sablitzky, F., and Mahida, Y. R. (2011). Expression profiling of Wnt family of genes in normal and inflammatory bowel disease primary human intestinal myofibroblasts and normal human colonic crypt epithelial cells. Inflammatory bowel diseases 17, 213-220. PMID: 20848536

Kirikoshi, H., Sekihara, H., and Katoh, M. (2001). Up-regulation of Frizzled-7 (FZD7) in human gastric cancer. International journal of oncology 19, 111-115. PMID: 11408930

Nambotin, S. B., Lefrancois, L., Sainsily, X., Berthillon, P., Kim, M., Wands, J. R., Chevallier, M., Jalinot, P., Scoazec, J. Y., Trepo, C., et al. (2011). Pharmacological inhibition of Frizzled-7 displays anti-tumor properties in hepatocellular carcinoma. Journal of hepatology 54, 288-299. PMID: 21055837

Nambotin, S. B., Tomimaru, Y., Merle, P., Wands, J. R., and Kim, M. (2012). Functional consequences of WNT3/Frizzled7-mediated signaling in non-transformed hepatic cells. Oncogenesis 1, e31. PMCID: PMC3503290

Nusse, R. (2008). Wnt signaling and stem cell control. Cell research 18, 523-527. PMID: 18392048

Nusse, R., and Varmus, H. E. (1982). Many tumors induced by the mouse mammary tumor virus contain a provirus integrated in the same region of the host genome. Cell 31, 99-109. PMID: 6297757

Pode-Shakked, N., Harari-Steinberg, O., Haberman-Ziv, Y., Rom-Gross, E., Bahar, S., Omer, D., Metsuyanim, S., Buzhor, E., Jacob-Hirsch, J., Goldstein, R. S., et al. (2011). Resistance or sensitivity of Wilms' tumor to anti-FZD7 antibody highlights the Wnt pathway as a possible therapeutic target. Oncogene 30, 1664-1680. PMID: 21472018

Reya, T., and Clevers, H. (2005). Wnt signalling in stem cells and cancer. Nature 434, 843-850. PMID: 15829953

Reya, T., Duncan, A. W., Ailles, L., Domen, J., Scherer, D. C., Willert, K., Hintz, L., Nusse, R., and Weissman, I. L. (2003). A role for Wnt signalling in self-renewal of haematopoietic stem cells. Nature 423, 409-414. PMID: 12717450

Simmons, G. E., Jr., Pandey, S., Nedeljkovic-Kurepa, A., Saxena, M., Wang, A., and Pruitt, K. (2014). Frizzled 7 expression is positively regulated by SIRT1 and beta-catenin in breast cancer cells. PloS one 9, e98861. PMCID: PMC4045932

Song, J., Gao, L., Yang, G., Tang, S., Xie, H., Wang, Y., Wang, J., Zhang, Y., Jin, J., Gou, Y., et al. (2014). MiR-199a regulates cell proliferation and survival by targeting FZD7. PloS one 9, e110074. PMCID: PMC196968

Takada, R., Satomi, Y., Kurata, T., Ueno, N., Norioka, S., Kondoh, H., Takao, T., and Takada, S. (2006). Monounsaturated fatty acid modification of Wnt protein: its role in Wnt secretion. Developmental cell 11, 791-801. PMID: 17141155

Ueno, K., Hazama, S., Mitomori, S., Nishioka, M., Suehiro, Y., Hirata, H., Oka, M., Imai, K., Dahiya, R., and Hinoda, Y. (2009). Down-regulation of frizzled-7 expression decreases survival, invasion and metastatic capabilities of colon cancer cells. British journal of cancer 101, 1374-1381. PMCID: PMC2768449

Vincan, E., Flanagan, D. J., Pouliot, N., Brabletz, T., and Spaderna, S. (2010). Variable FZD7 expression in colorectal cancers indicates regulation by the tumour microenvironment. Developmental dynamics: an official publication of the American Association of Anatomists 239, 311-317. PMID: 19655379

Wei, W., Chua, M. S., Grepper, S., and So, S. K. (2011). Soluble Frizzled-7 receptor inhibits Wnt signaling and sensitizes hepatocellular carcinoma cells towards doxorubicin. Molecular cancer 10, 16. PMCID: PMC3050858

Willert, K., Brown, J. D., Danenberg, E., Duncan, A. W., Weissman, I. L., Reya, T., Yates, J. R., 3rd, and Nusse, R. (2003). Wnt proteins are lipid-modified and can act as stem cell growth factors. Nature 423, 448-452. PMID: 12717451

Yang, L., Wu, X., Wang, Y., Zhang, K., Wu, J., Yuan, Y. C., Deng, X., Chen, L., Kim, C. C., Lau, S., et al. (2011). FZD7 has a critical role in cell proliferation in triple negative breast cancer. Oncogene 30, 4437-4446. PMID: 21532620

What is claimed is:

1. A monoclonal anti-human FZD7 antibody or antibody fragment that specifically binds to human FZD7, but which does not appreciably bind to other human FZD polypeptides, wherein said FZD7 antibody or antibody fragments thereof comprises:
   (a) a variable light chain comprising a CDR1 sequence comprising SEQ ID NO:6, a CDR2 sequence comprising SEQ ID NO:7, and a CDR3 sequence comprising SEQ ID NO:8; and
   (b) a variable heavy chain comprising a CDR1 sequence comprising SEQ ID NO:9, a CDR2 sequence comprising SEQ ID NO:10, and a CDR3 sequence comprising SEQ ID NO:11.

2. The monoclonal anti-human FZD7 antibody or antibody fragment of claim 1, wherein the FZD7 antibody or antibody fragments thereof binds to SEQ ID NO: 43.

3. The monoclonal anti-human FZD7 antibody or antibody fragment of claim 1, wherein the FZD7 antibody comprises a light chain comprising an amino acid sequence with at least 80% sequence identity to SEQ ID NO: 4 and a heavy chain comprising an amino acid sequence with at least 80% sequence identity to SEQ ID NO: 5.

4. The monoclonal anti-human FZD7 antibody or antibody fragment of claim 1, wherein the FZD7 antibody comprises a light chain comprising an amino acid sequence with at least 80% sequence identity to SEQ ID NO: 20 and a heavy chain comprising an amino acid sequence with at least 80% sequence identity to SEQ ID NO: 21.

5. The monoclonal anti-human FZD7 antibody or antibody fragment of claim 1, wherein the FZD7 antibody or antibody fragments thereof does not appreciably bind to any of FZD1, FZD2, FZD3, FZD4, FZD5, FZD6, FZD8, FZD9 or FZD10.

6. The monoclonal anti-human FZD7 antibody or antibody fragment of claim 1, wherein the binding affinity for human FZD7 is at least 10, 100, or 1000-fold greater than its binding affinity to any other human FZD polypeptide.

7. The monoclonal anti-human FZD7 antibody or antibody fragment of claim 1, wherein the FZD7 antibody or antibody fragments thereof binds to an epitope of human FZD7 comprising a leucine residue at position 188, wherein the leucine residue at position 188 of the human FZD7 corresponds to the leucine residue at position 156 of SEQ ID NO: 43.

8. The monoclonal anti-human FZD7 antibody or antibody fragment of claim 1, wherein the FZD7 antibody or antibody fragments thereof does not bind to a human FZD7 polypeptide comprising a leucine residue at position 188 of human FZD7 for the proline residue at position 188, wherein the leucine residue at position 188 of the human FZD7 corresponds to the leucine residue at position 156 of SEQ ID NO: 43.

9. The monoclonal anti-human FZD7 antibody or antibody fragment of claim 1, wherein the FZD7 antibody or antibody fragment thereof binds to an epitope of mouse Fzd7 polypeptide comprising a proline residue at position 188 of mouse Fzd7 for the leucine residue at position 188, wherein the proline residue at position 188 of the mouse Fzd7 corresponds to the proline residue at position 156 of SEQ ID NO: 44.

10. The monoclonal anti-human FZD7 antibody or antibody fragment of claim 1, wherein the FZD7 antibody or antibody fragments thereof blocks single cell spheroid formation of cancer cells.

11. The monoclonal anti-human FZD7 antibody or antibody fragment of claim 10, wherein the cancer cells are glioblastoma cells.

12. The monoclonal anti-human FZD7 antibody or antibody fragment of claim 1, wherein the FZD7 antibody fragment thereof is selected from scFvs, Fab fragments, Fab' fragments, or F(ab')2 fragments.

13. The monoclonal anti-human FZD7 antibody or antibody fragment of claim 1, wherein the FZD7 antibody or antibody fragments thereof is attached to at least one of an effector moiety, optionally a chemical linker and a cytotoxic agent or payload.

14. The monoclonal anti-human FZD7 antibody or antibody fragment of claim 1, wherein the FZD7 antibody or antibody fragment thereof is directly or indirectly attached to a detectable label or therapeutic agent.

15. The monoclonal anti-human FZD7 antibody or antibody fragment of claim 14, wherein the detectable label comprises one or more of a fluorescent dye, enzyme, substrate, bioluminescent material, radioactive material, chemiluminescent moiety, or mixtures thereof.

16. The monoclonal anti-human FZD7 antibody or antibody fragment of claim 1, wherein the FZD7 antibody or antibody fragment thereof neutralizes or inhibits FZD7 signaling via Wnt3a.

17. The monoclonal anti-human FZD7 antibody or antibody fragment of claim 1, wherein the FZD7 antibody or antibody fragment thereof neutralizes or inhibits FZD7-mediated cell migration.

18. The monoclonal anti-human FZD7 antibody or antibody fragment of claim 1, wherein the FZD7 antibody or antibody fragments thereof neutralizes or inhibits one or more of FZD7-mediated stem cell replication, self-renewal, or proliferation.

* * * * *